(12) United States Patent
Saha

(10) Patent No.: US 6,887,977 B1
(45) Date of Patent: May 3, 2005

(54) METHODS AND MATERIALS RELATING TO CD8-TROPIC HIV-1

(75) Inventor: Kunal Saha, Hillard, OH (US)

(73) Assignee: Children's Hospital, Inc., Columbus, OH (US)

(*) Notice: Subject to any disclaimer, the term of this patent is extended or adjusted under 35 U.S.C. 154(b) by 0 days.

(21) Appl. No.: 10/040,802

(22) Filed: Dec. 28, 2001

Related U.S. Application Data

(60) Provisional application No. 60/258,472, filed on Dec. 28, 2000.

(51) Int. Cl.[7] .............................................. A61K 38/00
(52) U.S. Cl. ....................... 530/324; 530/350; 530/826; 536/23.72
(58) Field of Search ................................ 530/350, 324, 530/826; 424/188.1, 204.1, 208.1; 536/23.72

(56) References Cited

U.S. PATENT DOCUMENTS

2002/0182592 A1 * 12/2002 Petropoulos et al. .......... 435/5

FOREIGN PATENT DOCUMENTS

WO    WO 00/71561    11/2000

OTHER PUBLICATIONS

Cullen, A New Entry Route for HIV, *Nature Medicine*, 7: 20–21 (2001).

Dumonceaux et al., Spontaneous Mutations in the env Gene of the Human Immunodeficiency Virus Type 1 NDK Isolate are Associated with a CD4–Independent Entry Phenotype, *Journal of Virology*, 72: 512–19 (1998).

Flamand et al., Activation of CD8+T Lymphocytes through the T Cell Receptor turns on CD4 Gene Expression: Implications for HIV Pathogenesis, *Proc. Natl. Acad. Sci. USA*, 95: 3111–3116 (1998).

Hoffman et al., HIV Type I Envelope Determinants for use of the CCR2b, CCR3, STRL33, and APJ Coreceptors, *Proc. Natl. Acad. Sci. USA*, 95: 11360–11365 (1998).

Huang et al., Construction and Characterization of a Temperature–Sensitive Human Immunodeficiency Virus Type 1 Reverse Transcriptase Mutant, *Journal of Virology*, 72: 2047–2054 (1998).

Kaneko et al., Human Immunodeficiency Virus Type 2 Envelope Glycoprotein Binds to CD8 as Well as to CD4 Molecules on Human T Cells, *Journal of Virology*, 71: 8918–922 (1997).

Kitchen et al., Costimulation of Naïve CD8+ Lymphocytes Induces CD4 Expression and Allows Human Immunodeficiency Virus Type 1 Infection, *Journal of Virology*, 72: 9054–9060 (1998).

Kolchinsky et al., Adaptation of a CCR5–Using, Primary Human Immunodeficiency Virus Type 1 Isolate for CD4–Independent Replication, *Journal of Virology*, 73: 8120–8126 (1999).

Livingstone et al., Frequent infection of peripheral blood CD8–positive T–lymphocytes with HIV–1, *Lancet*, 348: 649–654 (1996).

Saha et al., Generation of CD4+ and CD8+ T–cell clones from PBLs of HIV–1 infected subjects using herpesvirus saimiri, *Nature Medicine*, 2:1272–1275 (1996).

Saha et al., Endogenous Production of β–Chemokines by CD4+, but Not CD8+, T–Cell Clones Correlates with the Clinical State of Human Immunodeficiency Virus Type 1 (HIV–1)–Infected Individuals and May Be Responsible for Blocking Infection with Non–Syncytium–Inducing HIV–1 In Vitro, *Journal of Virology*, 72: 876–881 (1998).

Saha et al., Isolation of primary HIV–1 that target CD8+T Lymphocytes using CD8 as a receptor, *Nature Medicine*, 7: 65–72 (2001).

Saha et al., Evidence of Productively Infected CD8+T Cells in Patients With AIDS: Implications of HIV–1 Pathogenesis, *Journal of Acquired Immune Deficiency Syndromes*, 26: 199–207 (2001).

Semenzato et al., CD8+T Lymphocytes in the Lung of Acquired Immunodeficiency Syndrome Patients Harbor Human Immunodeficiency Virus Type 1, *Blood*, 85: 2308–2314 (1995).

Shankarappa et al., Consistent Viral Evolutionary Changes Associated with the Progression of Human Immunodeficiency Virus Type1 Infection, *Journal of Virology*, 73: 10489–10502 (1999).

* cited by examiner

*Primary Examiner*—Jeffrey Stucker
(74) *Attorney, Agent, or Firm*—Marshall, Gerstein & Borun LLP

(57) ABSTRACT

The present invention relates to human immunodeficiency viruses 1 (HIV-1) that infect CD8-positive cells using CD8 as a receptor, to detection methods for the viruses and to prophylactic and therapeutic methods for infection by the viruses.

6 Claims, 18 Drawing Sheets

```
ATGAGAGTGAAGGGGATCAGGAGGAATTATCAGCACTGTGTGGAGATGGGGCACCATGCTCCTTGGGATGTTGATGATCTG
TAGTGCTGCAGATCAATTGTGGGTCACAGTCTATTATGGGGTGCCTGTGTGAAGAAGCAACCACCACTCTATTTGTG
CATCAGATGCTAAAGCATATAGTACAGAGTACATAATATTTGGGCCACACATGCCTGTGTACCCACAGACCCCAGCCCA
CAAGAAATAGTGGAAGTAATGTGACAGAAGAGTTCAACATGTGGAAAATAACATGTAGAACAGATGCATGAGGATAT
AATCAGTTTATGGATGAAAGCCTAAAGGCCATGTGTAAATTAACTCCACTCTGTGTTACTCTAAATTGCACTACTGAGT
TGAATCTTCTAAATTGCATTGATAATAGTACTAATGATAAATGTATACCGCCAGATCAAAAGGAGAATGAAAACTGC
TCTTTCAATATCACCGCAGGCATAAGAAATAAGGTGCGGAAAGAATATGCACTTTTATACAAGTGATGTAGCACCAAT
AGATAATGATACTATCAGTTATATAGATTGATAAGTTGTAACACCTCATTACACAGGCCTGTCCAAAGTATCCTTTG
AGCCAATTCCCATACACTATTGTGCCCCGGCTGGTTTGCGATTCTAAAGTGTAAGGATAGGAATTTCAATGGAACAGGA
CTATGTAAAAATGTCAGCACAGTACAATTAGATCTGAAAATTCACGGACAAGGTCTACGTATAGGACCAGGAGAGCATGGTGGTAT
TCTGGCAGAAAAAGAGATAGTAATTAGATCTGAAAATTCACGGACAAGGTCTACGTATAGGACCAGGAGAGCATGGTGGTAT
TAGTACACATTAATTGTACAAGACCTAACAATAATATAAGAAAAGGTTCAACATTAGGACAGTAAAATGGAATAACACTTTAGACA
GCAACAAGAGGAATAATAGGAGAAAAAATGAGACAAACACATTGCCAACATTAGTAGGGGACTAATAATAATTAATCAACTGTTTAATGACTGG
GATAGTTAAAAAATTAGGGAGACAACTTTTAATTGTGGAGGGGAATTTTTACTGTAATACACAACAACTGTTTAATGACTGG
CAGAAATTACAATGCACACTTTAATTGTGGAGGGGAATTTTTACTGTAATACACAACAACTGTTTAATGTACTGG
ATTCGGAATGGTACTGATTGGACTCGAAATGATACTGAAGGATCAGAACATCAGTAAGAACACTCACGCTCCCATGTAG
AATAAAACAAATTATAAACATGTGGCAGAAAGTAGGGAAAGCAATGTATGCCCCTCCCATCAGTGGACAAATTAGCTGTT
CCTCAAATATTACAGGGCTGCTATTAACACACGATGGTGTTGGTCTGTACAGGACGGGAACAACGTGACCTTCAGA
CCGGGAGGAGGAAATATGAGGGACAATTGAGGGACAAGAGAGTGTGCAGAGAAAAAGACAGTGGAATAGCAGTGGAATAGCAGACACAATTATTGTCTGGTATAGTG
AGCACCCACCAAGGCAAGACAATCTCGCTGGCTATGAGGCGCATGGGCGCTATTGAGGCGCAACACATATGTTGCAACTCAGTCTCGGGAATTTGGGGTTGCTCTGGAAAACTCA
CCAGGCAAGAGTCCTGCTGTGCCTTGGAATAGTAGTATTACACAAGCTATATACACCTTAATTGAAGAATCGCAGAACCAGCAAGA
TGGATGAAGTGGAAAAGAGAATTATTGGAATTAGACAAATGGGACAGTTTGTGGAGTTGGTTTAGCATAACAAACTGGCTGTGGT
AAAGAATGAACTAGAAAATATTCATAATGATAGTAGGAGGCTTGATAGTTTAAGAATAGTTTTAGGTGTGTCTTCTATAGTGAATAGA
ATATAAAATATTCATAATGATAGTAGGAGGCTTGATAGTTTAAGAATAGTTTTAGGTGTGTCTTCTATAGTGAATAGA
GTTAGGCAGGGATACTCACCATTGTCGTTTCAGACCCGGCCCCAGCCCAGCCCCGAGGGACCCCAGGAGGTCGACCTGC
AGAAGAAGGTGGAGAGAGAGACAGATCCGGCAGATTAGTGACAGATTCTTAGCACTTATCTGGTCGACCTGC
GGAGCCTGTGCCTCTTCAGCTACCACCGCTTCAGTGGAATCTCCTACAGTACTGGAGTCAGGAACTAAAGATAGTGCTGTTAGCTT
AGGGGGTGGGAAGTCCTCAAGTATTGTTGAAATCTCCTACAGTACTGGAGTCAGGAACTAAAGATAGTGCTGTTAGCTT
GCTTAATACCATAGCAATAGCAGTAGCTGAGGGACAGATAGGGTTATAGAAATAATACAAAGAGCTTGTGAGAGCTATTC
TCCACATACCTAGAAGAATAAGACAGGGCTTTGAAGGGCTTTGCTATAA
```

FIG. 1

```
ATGAGAGTGAAGGGGATCAGGAAGAAGAATTATCAGCACTTGTGGAGATGGGCACCATACTCCTTGGGATGTTGATGATCTG
TAGTGCTGCAGATCAATTGTGGGTCACAGTCTATTATGGGGTGCCTGCTGTGTGGAAAGAAGCAACCACCACTCTATTTGTG
CATCAGATGCTAAAGCATATAGTACAGAGGTACATAATATTTGGGCCACACATGCCTGTGTACCCACAGACCCCAGCCCA
CAAGAAATAGTAATGGAAAATGTGACAGAAGAGTTCAACATGTGGAAAAATAACATGGTAGAACTCTAAATTGCACTACTGAGT
AATCAGTTTATGGGATGAAAGCCTAAAGCATGTGTAAAATTAACACTGTGTTACTCTAAATTGCACTACTGATGAT
TGAATCTTCTAAATTGCATTGATAATAGTACTAGTGGTAATAACACTGCTCTTCAATATCACCGCAGGCATAAGAGATAAGGTGCG
AAATGTATACCGCCAGATCAAAAGGAAAAATGAAAACTGCTCTTCAATATCACCGCAGGCATAAGAGATAAGGTGCG
GAAAGAATATGCACTTTTTATACAAGTGATGTAGCACCAATAGATGATGCTATCAGTTATAGATTGATAAGTTGTA
ACACCTCAATCATTACACAGGCCTGTCCAAAGGTATCCTTTGAGCACAGTACACTATTGTGCCCCGGCTGGTTT
GCGATTCTAAAGTGTAAGGATAGGAATTTCAATGGAACAGGACTATGTAAAATGTCAGCACAGTACAATGTACACATGG
AATTAGGCCAGTAGTATCAACTCAACTGCTGTTAAATGGCAGTCTGCAAAAAAAGAGATAGTAATTAGATCTGAAAAT
TCACGGACAATGCTAAAACCATAATAGTACAGCTGCCTGAAATAGTACACATTAATTGTACAAGACCTAACAATATATA
AGAAAAGGTCTACGTATAGACCAGGGAGACATGTGTATGCAACAAGAGGAATAATAGGAAAATGAGACAAACACA
TTGCAACATTAGTAGAGAAAATAATGAATAACACTTTTAGAACAGATAGTTAAAAAAATTAGGAGACAAATTTGGGACTAATA
ATAATAAAACAATAATATTTACAACACAACTGTTTAATACACGCTCCCCAGAAATTACAATGGTACTGATTGGACTCAAATGATACTGA
TTTTTTACTGTAATACAACACTACTAACGCAAATATCACGCTCCCATGTAGAATAAACAAATTATTACAGGGCTGCTATTAACACATGGTA
AGGATCAGACATCACTACTGCCCCTCCATCAGTGGACAACGTGTTCATCAAATATTCAGGGCTGCTATTAACACACGATGGT
AAGCAATGTATGCCCCTCCATCAGTGGACAACGTGTTCATCAAATATTCAGGGCTGCTATTAACACACGATGGT
GTTGTTGGTCTGTACAGAACGCGAACAACGTGACCTTCAGACCGGAGGAGAAATATGAGGGACAATTGGAGAAGTGA
ATTATATAAATATAAGTAATAAAGTTGAACCAATAGGAATAGCACCCAAGGCAACAGCAATCTGCTGAGGGCTATTGAGGGCA
AAAAGAGCAGGTACAAGCCAGAACAATTATTGTCTGTATAGTGCAACAGCAGAACAGTCCTGGCTGTGCAGGGCTATTGAGGGCA
ACGCTGACGGTACAAGCCAGAACAATTATTGTCTGTATAGTGCAACAGCAGAACAGTCCTGGCTGTGCAGGGCTATTGAGGGGCA
AGCAGCATATGTTGCAACTCACAGTTGGGGCATCAAGCAGCTCCAGGCAAGAGTCCTGGCTGTGCCTTGGAAATAGTAGTTGGAGT
ATCAACAGATCTCTGGGAGACATTTGAAGAATCGCAGAAACTGATAACCAGCAAGAAATGATAATCATAATGATAGTAGGAGGCTTGATA
AATAGATCTCTGGGAGACATTTGAAGAATCGCAGAAACTGATAACCAGCAAGAAATGATAATCATAATGATAGTAGGAGGCTTGATA
CTATATATACACCTTAATTGAAGATATAACAAACTGGCTGTGTATAGAGTTAGGCAGGGATACTCACCATTGTCGTTTCAGACCCG
ACAGTTTGTGGAAATAGTTTTAGTGTGCTTCTATAGTGAATAGAGTTAGGCAGGGATACTCACCATTGTCGTTTCAGACCCG
GGTTTAAATATAGTTGGGCCCCGAGGGGACCGGCAGCCGGGGACCGACAATCTGGGTCGACCTGCGCGAGACGCAGGCAGGCTGCCCTCTTCAGCTCGACGTGCCCTCTTCAGCTCGACGTGCCCTCTTGAAGGGGGACAGGCAGGGGTGGGGAAGTCCTCAAGTATTGTTGAATCTCCT
GATTAGTGATGGATTCTTAGCACTTATCTGGGTCGACCTCGGGACCGACCTCGGGACCGACCTCGGGACCGACCTCGGGACCGACCTCGGGACCGACCTCGGGACCGACCTCGGGACCGACCTCGGGACCGACCTCGGGACCGACCTCGGGAGCTCCT
TTACTCTTGATTGCAGCGAGGATTGTGAACCTCCCTGGGAACCGCAGCAGGGCTCGGGACCGACCTCGGGACCGACCTCGGGACCGACCTCGGGACCGACCTCGGGACCGACCTCGGGAGCTCCT
ACAGTACTGGAGTCAGGAACTAAAGAATAGTGCTGTTAGCTTGCTTAATACCATAGCAATAGCAGTAGCTGAGGGACAG
ATAGGGTTATAGAAATAATACAAAGAGCTTGTAGAGCTATTCTCCACATACCTAGAAGAATAAGACAGGCTTTGAAGG
GCTTTGCTATAA
```

FIG. 2

```
atgagagtgaaggagagaaatatcagcactgtggaatgcgggtgagatggggcaccatgctcctggatgttgatgat
ctgtagtgctacagaaaaattgggtcacagtctattggtgatcctgtgtggaaggaagcaacaccactctattt
gtgcatcagatgctaaagcatatgatacagagagtacatatgtttggccacacatgcctgtgtacccacagaccccaac
ccacaagaagtagtattggtaaatgacagaaaaatttaacatgtggaaaaatgacatggtagaacagatgcatgagga
tataatcagtttatgggatcaaagcctaaagccatgtgtaaaattaaaccccactctgtgttagtttaaagtgcactgatt
tgaagaatgatactaataccaatagtagtcggagaagaatatgcattttttataactgtgataatgtgagataatgtaaaactgctctttcaat
atcagcacaagcataagagagtaaggtgcagaaagaatatgcattttttatactgatataatccaatagataatga
tactaccagctataagtgacaagttgtaacacctcagtcattacacaggcctgtccaaagttctttgagccaattc
ccatacattcttgtgccccgctggtttgccattcaaaatgtaataataagacgttcaatggaacaggaccatgtaca
aatgtcagcacagtacaatgtacacatggaattaggccagtaggtatcaactcaacctaaactcatcgtgagaa
agaagaggtagtaattagatctgtcaatttcacggacaatgtctaaaaccataatagtcagctgaacacatctgtagaaa
ttaatgtacaagaccccaacaacaacaagaaaagaatcgtatccagagagaccagggagagcatttgttacaata
ggaaaaataggaaaatgagacaagcacattgtaacattagtagagcaaaatgaataacacttaaaacagatagctag
caaattaagaagaacaatttggaaatataaaacaaatacttaagcaatcttaacacaactgtttaatagtacttgg
acagttttaatgtgagggggaattttctactgtaattcaacacaactgtttaatagtactgtggttaatgtacttgg
agtactgaaggtgtcaaattaacactgaaggaagtgacacaatcacccctccatgcagaataaaacaaattataaacatgtg
gcagaaagtaggaaaagcaatgtatgcccctccatcagtgagacaaaattgatgttcatcaaatattacaggctgctat
taacaagagatggtggtaatgccaacaatgagtccgagatctcagacctggagggaggagaatatgaggacaattggaga
agtgaattatataaatataagtagtaaaaattgaaccettagagtagcacccaaggcaagagagaggtggtca
gagagaaaaaagagcagtggaataggagctttgttcctggttcctggttgcagccagcaggaagcactatgggcgcagcct
caatgacgctgacggtacaggccagacaattatgtctggtatagtgcagcagcagcaagaatctggctgtgaagatacct
gcgcaacagcatctgttccaactcacagtcgggcatcaagcagctccaggcaagaatctggctgtgaagatacct
aaggaatcaacagctcctgggatttggggttgctctggaaaactcatttgccacactgctgcctgaatgctagtt
ggagtaataaatctctgaacagatttggaatcaacagacctggatgggtttggaagatgtggacagaaatacacaagc
ttaatacactccttaattgaagatcgcaaaaccagcaagaaaagaatgacaagaattattgaattagataaatgggc
aagtttgtggaattggttttaacataacaaattggctgtggtatataaatattcataatgatagtaggaggcttggtag
gtttaagaatagttttgctgtactttctataagtgaatagagttaggcaggataataccacattatccgtttcagacccac
ctcccaacccgaggggaccgacaggcccgacaggcccgaagaataagaggaagaggtggagagagacagagacagatccattcg
attagtgaacggatcctggcacttatctggacgatctgggacgatgcgagcctgcctcttcagctaccaccgcttgagagact
tactcttgattgtaacgagattggaacttcggacgagggcgaggggtggaagccctcaaatattgtggaatctccta
cagtattggagtcaggaactaagaagataatagtgcgttagctgctcaatgccacgcacagctagcaggcaggggacaga
taggttatagaagtagtacaagaggagctgtagagctattcgccacatacctagaaataagacacaggcttgaaagga
ttttgctataa
```

FIG. 3

```
                 1                                                          50
HXB2      MRVK...EKY QHLWRWGWRW GTMLLGMLMI CSATEKLWVT VYYGVPVWKE
WEAU1.6   ----GIRKN- ---:...-K- .IM----I-- ---AEN---- ----------
AD3.V6    ----GIRRN- ---:...-R- -GTM---M-- ---ADQ---- ----------
AD3.V22   ----GIRKN- ---:...-R- -GTI---M-- ---ADQ---- ----------

51                                                         100
HXB2      ATTTLFCASD AKAYDTEVHN VWATHACVPT DPNPQEVVLV NVTENFNMWK
WEAU1.6   ---------- ----D----- -V-------- --N---V-LE ----N-----
AD3.V6    ---------- ----S----- -I-------- --S---I-ME ----E-----
AD3.V22   ---------- ----S----- -I-------- --S---I-ME ----E-----

101                                                        150
                                                          ┌──► V1
HXB2      NDMVEQMHED IISLWDQSLK PCVKLTPLCV SLKCT..... ..........
WEAU1.6   -N-------- -------Q-- ---------- T-N--N.... ......VNV
AD3.V6    -N-------- -------E-- ---------- T-N--TELNL LNCID.....
AD3.V22   -N-------- -------E-- ---------- T-N--TELNL LNCIDNSTSG

151      V1                              ──► V2           200
HXB2      .DLKNDTNTN SSSGRMIM.. EKGEIKNCSF NISTSIRGKV QKEYAFFYKL
WEAU1.6   TNLKNETNT- -SSGGEKM.. EE-EM----- -VTTL--N-R KT---L--KL
AD3.V6    .......... -TNDKCIPPD QK-EM----- -ITAG--N-V RK---L--TS
AD3.V22   NNTDNSTSS- -TDDKCIPPD QK-KM----- -ITAG--D-V RK---L--TS
```

Fig. 4A

```
           201  V2  ↓  .
HXB2       DIIPID..ND TTSYKLTSCN TSVITQACPK VSFEPIPIHY CAPAGFAILK  250
WEAU1.6    -VM---.R- NT--T-IN-K S-T------- ---------- ----------
AD3.V6     -VA---.N- TI--R-IS-N T-I------- ---------- ----------
AD3.V22    -VA---.N- KI--R-IS-N T-I------- ---------- ----------

251
HXB2       CNNKTFNGTG PCTNVSTVQC THGIRPVVST QLLLNGSLAE EEVVIRSVNF  300
WEAU1.6    -NDKK---K- P-K------- ---------- ------E    EDI----E--
AD3.V6     -KDRN---T- L-K------- ---------- ------E    K-I----E--
AD3.V22    -KDRN---T- L-K------- ---------- ------K    K-I----E--

▲V3
           301                                          350
HXB2       TDNAKTIIVQ LNTSVEINCT RPNNNTRKRI RIQRGRSRA. FVTIGK.IGN
WEAU1.6    ---------- -NVSLE---- ----T--KI  TL..---VL  YTTGEI.--D
AD3.V6     ---------- -PEIVH---- ----I---GL RI..----AW WYATRGI--K
AD3.V22    ---------- -PEIVH---- ----I---GL RI..----AW WYATRGI--K

V3
           351 ↰
HXB2       MRQAHCNISR AKWNNTLKQI ASKLREQFG. .NNKTIIFKQ SSGGDFEIVT  400
WEAU1.6    I-RA---L-- TS-----K-- VE--REIKQF .K---V-K-- ---------- --VM
AD3.V6     M-QT----I- VK-----E-- VK--GDKFGT NN-----I-N ---------- --TM
AD3.V22    M-QT----I- EK-----E-- VK--GDKFGT NN-----I-N ---------- --TM
```

Fig. 4B

```
         401                                                          450
HXB2     HSFNCGGEFF YCNSTQLFNS TWFNSTWSTE GSNNTEGSD. ...TITLPCR
WEAU1.6  -S-------- --------S- ---------- --HANGT.WK N.....A-. ..NN------
AD3.V6   -T-------- --------T- ---------- --IRNGTDWT R.ND----S-I TNEN------
AD3.V22  -T-------- --------T- ---------- --IRNGTDWT Q.ND----S-I TNEN------

451                                                         ~500
HXB2     IKQIINMWQK VGKAMYAPPI SGQIRCSSNI TGLLLTHDG. .GNSN.NESE
WEAU1.6  -----R---E ---------- E---R---L- --------- -R--. .-SSEENQTE
AD3.V6   -----M---K ---------- S----S---- --S-S---- ------H--V V-LYTDANNV
AD3.V22  -----M---E ---------- S----S---- --S-S---- ------H--V V-LYTNANNV

HXB2     IFRPGGGDMR DNWRSELYKY.KVVKIEPLGV APTKAKRRVV QREKR
```

Fig. 4C

```
atgagagtgaaggggatcaggaagaattatcagccacttgtggagatgggcaccatgctcctggatattaatgatctg
tagtgctgcaggccaattgtggctcacagtcattatgggtacctgtgtggaaagaagcaaccacactctatttgtg
catcagatgctaaagcatatgatacagaggtacataatgttggccacacatgcctgtaccacagaccccaaccca
caagaagtagtattgggaaatgtgacagagaaaattttaacatatgaaaataacatgtagaacagatgcatgaggatat
aattagtttatggatcaaagcctaaaaccatgtgaaaatacccactctgtactctaaattgcactgatttga
ggaatgctactaataccactagtagtgcgggaaatgatgcggagagagaaataaaaactgtctttcaatatcacc
acaagcataagagatataaatgcagaaagaatatgcactttttataaactgatgtagtaccaatagatactaataatac
taataccagctataggctggtaagttgtaaccactcagtcattacaaatgtaataataagacgttcaaagtgtatcctttgagccaatc
ccatacattattgtgccccggctggtttgcgattctaaaatgtaaaatgtaataaaatgctgttaaatggcagtctagcaga
aatgtcagcacagtacaatgtctgaacaatgtgaacattgcaagtctaatcaactgctgttaaatggcagtctagcaga
agaagagatagtacaagcccaacaacaatacaagaaaagtatacatataggaccagggagccatttatacaacaggagaa
ttaattgtacaagaccaacaacaatacaagaaaagtatacatataggaccagggagccatttatacaacaggagaa
ataaltaggagataagacaagcacattgtaacattgagcaaaatgaatgacacttaagacagatagctaaaca
attaagagaacaatttaaaaataaacaaataatcttttaatcaatcgtaggaggggaacccagaaattgtaacgcacagtt
ttaattgtgagggggaatttttdactgtaaftcagcaacaactgtttaacagtactggaatgatactgaaagtcaaat
aacaactagaagaaaatgaccaacaactcccatgcagaataaacaaatataaacatgtggcaggaagtagagaaa
agcaactgtatgccctcctcctatacagaggacaaattaaatgcatcaaatatcacaggctgtctattaacaagagagatgtg
gtaataacaatactggaccaccgagaccttcagacctgagagagatatgaggagacaattgagacaatgaattgaattatat
aaatataaagtagtaaaaattgaaccattaggaatagcaccactaggaatagcaccactaggaatagcaccactagaaagaagagaggtgcagagagaaaaag
agcagtggaataggagagctgtgttcctggggttctgtggagctgcaacagcaaacaatctgtgagggcattgaggcgcaacagcat
cggtacaagccagctattattgtctggtataggtcaacagcagcccaggcaagagtcctgctgtgaaaaatccagggatcaaca
ctgttgcaactcacagtctggggttgctctggaaatacctcatttgcaccactatggccttggaatactagttggagtaataaat
gctcctggaatttggggttgtctggaaatctgacctgagagagagaaattgacaattacacaggtttaatatacacc
ctctggatacgattgaataacatgacctggatgcagtgggaaagaagaaattattgaattagataatggcaagttgtggaa
ttactttgaagaatgcagaaccaacaagaaagaagaaaaagaataacaagaattattgaattagataatggcaagttgtggaa
ttggtttgacataacaaactggctgtggtataaaatattcataatgataagaggctggtaggtttaagaalag
ttttgctgactttctatagtgaatagagttaggcaggagatactcaccattatcgtttcgaccgcctccagccccg
agggaacccgacagaccgaaggaattcgaagaagaagttgagagaagaagaggagagaggaacagagacagatccggtcgattagtggaatgg
cttcttagcaatcatcgggtcgacctacggagcctgtgctctttcagctaccaccgattgagagacttacttcttgattg
taacgaggattgtgaacttctggaccgacggggggtggaagcctcaaatactggggaalctccacagtattggagt
caggaacataaagaaatagtgcgttagctttgcaatgcaacaagccatagccatagcagctgtcgagggaacagataggtatage
agtgttacaaagagctgtagagcttattctccaataactctaagaataagacagggctttgaaagggcttgaaagggcttgctataa
```

```
                                          V5                                                              gp120 ends ◄─── 535
         481                      ▼                          ▼
HXB2        TGLLLTRDGG NSNN..ESEI .FRPGGGDMR DNWRSELYKY KVVKIEPLGV APTKAKRRVV QREKRAVG.I GALFLGFIGA
92UG046-T8  ---------- ...-NTRQNE A--------- ---------- -----R---L -----E---- E----I-.L --M-------
93UG086-T8  ---I------ D...NNSTNE T--------- ---------- ---------- -----R---- E-----IAG- --V-------
92US077-T8  ---------- ---T-DTNNT --------.- ---------- --------I- ---------- ---------- ----------
93US143-T8  ---------- ---VDE-SNTT-T ---------N ----A----- ---------- ---------- -----M--.- ----------
96USHIPS4-T8 --------- ---I-ETNGT- ------A--- ---------- ---------- ---------- ---------V --M-----S-
96USHIPS9-T8 --------- ...S-TNTT-V .-------N-K ---------- ---------- ---------- ---------V ----------
96USSN20-T8 --I------ K...INSTNE T--------- ---------- ---------- -----H---- E------V-. ----------
AD3.V6      -----H---V VGLYTDANNV T--------N ---------- --I-V--I-I ---------- ---------- --M------T HXB2        AGSTMGAASM TLTVQARQLL SGIVQQQNNL LRAIEAQQHL LQTLVWGIKQ LQARILAVER YLKDQQLLGI WGCSGKLICT
92UG046-T8  ---------M ---------- ---------- ---------- ---------- -----S---- ---------- ----------
93UG086-T8  ---------- ----T----- ------S--- ---------- --K-K----- ---------- ---------- ------RII-
92US077-T8  ---------- ---------- ---------- ---------- ---------- ---------- ---------- ----------
93US143-T8  ---------- ---------I ---------- ------H--- ---------- --V------- ---------- ----------
96USHIPS4-T8 --------- ----V----- ---------- ---------- ---------- --V------- ---------- ----------
96USHIPS9-T8 --------- ----T----- ------S--- ---------- ---------- --V------- ------G--- ----------
96USSN20-T8 ---------- ----AI---- ---------- ------H--- ---------- --V------- --------F- ----------
AD3.V6      ---------- -----A---V ---------- ---------M --K-K----- --V----L-- ------R--- ----------

HXB2        TAVPWNASWS NKSLEQIW.. NHTTWMEWDR EINNYTSLIH SLIEESQNQQ EKNEQELLEL DKWASLWNWF NITNWLWYIK
92UG046-T8  -------S-- -----NE--. GNM------EK --D---E--Y ------T--- -------K-- -Q-------- S--K------
93UG086-T8  --T----S-- -----YSE--. DNM--LQ--K --S---QI-Y D--------- ------D-A- ------N--- D-SK------R
92US077-T8  -------S-- -----DK--. -NM--Q--E- --D-------Y T--------- ---------- ------N--- D--K------
93US143-T8  -------T-- -----DR--. -NM-------E --D---G--Y N--------- ------A--- ---------- D---------
96USHIPS4-T8 ------T-- -----KY--. DNM---Q--K --S---G--Y T--------- ------K--- ---------- D---------
96USHIPS9-T8 ------T-- -----DD--. QNM------E- --D---NV-Y N--------- ------D-A- -----D---- S--S------
96USSN20-T8 -N-----S-- -----TFND-. .NM--LQ--K ------NT-Y R--------- ------D-A- ------S--- DLS------R
AD3.V6      -------S-- --R--GD-EN DNM---K-E- --D---Y-Y T--------- ------L--- ------D--- S---------
```

Figure 6C

```
HXB2          LFIMIVGGLV GLRIVFAVLS IVNRVRQGYS PLSFQTHLPT PRGPDRPEGI EEEGGERDRD RSIRLVNGSL ALIWDDLRSL
92UG046-T8    I--------- I-------- V-------- ---------- ---------L-A ---------- ------QG-G ---T-FS--- -----N----
93UG086-T8    I--------- I-------- -I--VI---- ---------- ---LA-N-G-L----GR- ---------- ------Q--S ---S-F---- ---A-E----
92US077-T8    I--------- -----VI--- -------- ---------- ---R--A Q-- ---------- ---G-G---- T-GP--D-F- --I--V----
93US143-T8    I--------- --------- -------T-- ---------- ---H-A Q-E- ---------- --G------- --GP--D-F- --I--V----
96USHIPS4-T8  I---I----- --------- -------T-- ---------- ------R--- Q ---------- ---G------ --RTS-D-F- ------V---
96USHIPS9-T8  I--------- --------- ----I-T--- ---------- ---RF-A--- ---------- --G-----K- ---GL----FF ------V---
96USSN20-T8   I-----V--- -I-------- --------- ---------- ---LTHH Q-E ---------- --G-----Q- ---V------F ---A------
AD3.V6        I--------- -A-------A ---------I ---------- ---RP-A--- ---------- ---G------ ---G-----D-F- ------V---

HXB2          CLFSYHRLRD LLLIVTRIVE LLG....... RRGWEALKYW WNLLQYWSQE LKNSAVSLLN ATAIAVAEGT DRVIEVVQGA
92UG046-T8    -----RH--- --I--AAK--- -F-....... ---*------ ---------- ---------- ---------- ----------
93UG086-T8    ---------- FI--AA-T--- ---HSSLKGL ---------L ---G---L-G ---I--I--FD TI--VI--GW -----IG-RI
92US077-T8    F--------- --------A- ---....... ---------- ---I-----I ---------- ---------- ----I---ARRT
93US143-T8    -I--L----- ---------- ---....... ---------- ---V------ ---------- ---------- -------IL-R-
96USHIPS4-T8  ---------- ---LA----- ---....... ---------- ---T-R---- ------IN-- ---SI--V-- --------RV
96USHIPS9-T8  ---------- ---AA----- ---....... ---------- -----I---- ---------- ------V--- ---IL--L-R-
96USSN20-T8   ---------- ---AA-T... ---HSSLKGL ---L--G----L ---------- ------IN-D T------ ------IG-RF
AD3.V6        ---------- ---AA----- ---....... ---------- -----V---C ---------- ---TI----- -------II-R-

HXB2          CRAIRHIPRR IRQGLERILL
92UG046-T8    ---------- ----------
93UG086-T8    G---LN---- ----A--A-Q
92US077-T8    F---L----- --------A-
93US143-T8    F---L---T- --------A-
96USHIPS4-T8  ---------- --------A-
96USHIPS9-T8Y ---I------ --------A-
96USSN20-T8   G---LN---- --------A-Q
AD3.V6        ----L----- ----F--A--
```

Figure 6D

92UG046-T8 (SEQ ID NO: 9)

ATGAGAGTGAAGGGGATAGAGAGGAATTATCAGCATTTGTGGGAGAGGAATCAGCACTCGTTGTGGAGATGGGCATCAT
GCTCCTTGGGATGTTAATGATATGTAAAGGAGAGAATTGTGGGTCACAGTTATTATGGGTACCTGTGTGAAAGAAGCAA
CCACTACTCTATTTTGTGCATCAGATGCTAAATCATATGAACCAGAGGCACATAATATCTGGCTACACATGCCTGTGTG
CCAAACAGACCCCAACCCACGAGAATAAAACTGGAAATGTCACAGAAAATGTGAAAATTAACCCCACTCTGTGTCACTT
GCAGATGCATGAGGATGTAATCAGTCTATCGGATCAAGCCTGAAACCTGATAGGGACATAGGAATGAAAAACTGCTCTTC
TACATTGCACTGAATAAGCCCCTAATGCCACTATTAATGCCACTATTAATGCCACTGATAGGGACATAGGAATGTGGTACAAATGATGA
AATGTAACCACAGAAGTAATAAATAGAAGAAGC

93UG086-T8 (SEQ ID NO: 11)

ATGAGAGTGAAGGGGATACAGAGGAACTGTCAAAACTTGTGGAGATGGGGAACTATAATCTTGGTATGATGATAATTTG
TAGTGCTGCAGAAAAATTGTGGGTTACTGTTACTGTTACTATGGGGTACCTGTGTGGAAAGATGCAGAAACCACCTTATTTGTG
CATCAGATGCGAAAGCATAIGATGAAGTGCATAATGTCTGGGCCACACATGCCTGTGTACCTACAGACCCAACCCA
CAAGAAATAAATTTGGAAATGTGACAGAAATTTAACATGTGGAAAAAATAACATGGTAGAGCAGATGCATACAGATAT
AATCAGTCTATGGGACCAAAGCCTAAAGCCATGTGTACAGTTAACCCTCTGTGTTACTTTAGATTGTACTGATGCCA
CAAATGCCACTAATACCACTATCATTAGTGACATGAAAGGAGAAATAAAAAACTGCTCTTCAATATGACCACAGAATTA
AAGGATAAGACACAGAAAGTACGTTCATTTTCTATAAGATGGATATAGTACAAATTAACAACAACAACAGCAA
CAGTAGTCAGTATAGATTAATAAGTTGTAATACCTCAACCATTACACAAGCTGTCAAAGGATATCCTTTGAGCCAATTC
CCATACATTATTGTGCTCCCAGCTGGTTTTGCTCCAAATGAATCAAGCAGTAGTATCAACTACTGTTAAATGCAGTCTAGCAGA
AATGTCAGCACAGTACACATGCACACATGGAATATATCGAAATATCACAGACAATCAAGAAGAGGTATCAACTACTGCAACTTACTGAGCCTGTAAAA
AGAAAAGGTAATGATTAGATCTGAAATATCACAGACAATCAAGAAGAGGTATAGGGCCAGGACGAGCATTCATTGCAAGAGATAGA
TTAATTGTACCAGACCTAACAACATACAAGAAGCACATTGTAACATCAGTAACATCAGTTGCAGAATAACACTTTGCAGAAGTAGCCCAACA
ATAATAGGGGATATAAGACAAGCACATTGTAACATCAGTTAACATCAGTTGCAGAATAACACTTTGCAGAAGTAGCCCAACA
ATTAAGAACACACTTTGAGAACAGAACAATAATCTTTAATCACTCCGCAGGAGGGGACCCAGAAATAACTACACATAGTT
TTAATTGTGGAGGAGAATTTTTCTATTGTGTAGCACACTATAACTCTCCAATGCAGAATAACTCTCCAATGCAGAATAAGGCAGATTATAAGGATGTGGCAGAGAGT
GGGTCAAAATAGCACGGTTCAAATGCCCCTCCCATCCCAGGGGTAATAACTCTCCAATGCAGAATAAGGCAGATTATAAGGATGTGGCAGAGAGT
AGGACAAGCAATGTATGCCCCCTCCCATCCCAGGGGTAATAACTCTCCAATGCAGAATAAGGCAGATTATAAGGATGTGGCAGAGAGT
ATGGGGGGATAATAACAGCACAAATGAACCTAAGATTGAACCACTAGGAGTAGCACCACCAGGAGCAGCAGGCAAAGCAAATGGGCGAGCGTCACTGA
TATAAGTATAAAGTAGTAAGTAGGAATAGCAGGAGCTGTGTTCCTTGGGTTCTTGGGAGCAGCAGGAGCAGCAGGCAAAGCAAATGGGCGAGCGTCACTGA
AAGAGCAATAGCAGGAGTACAGCAGAACCAGAACAGCAGCAGCAGCAGCAGCAGCAGCAAAGCAAATGGGCGAGCGTCACTGA
CGCTGACGGTACAGGTACAGCAGAACCAGCAGCAGCAGCAGCAGCAGCAAAGCAAATGGGCGAGCGTCACTGA
CAGCATCGTTGAAACTCACGGTCTGGGGTTGCTCTGGAAAACTCCGCTCAACACTCCAGGCAACTCATTTGCACCACTACTGTGCCTGCCTGTGGAAGAATACCTAAGGA
TCAACAGCTCCTAGGAATTTGGGGTTGCTCTGGAAAACTCATTTGCACCACTACTGTGCCTGCCTGTGGAAGAATACCTAGTGGAGTA
ATAAATCCTATAGTGAAGATATGGGACAACAGCAGCAGCAGCAGCAGCAGCAGCAGCAAAGCAAATTAGCAATTAGAATTAATACAATAATA
TATGATCTAATTGAAGAATCACAGAACCAGCAGGAAAAGAATGAACAAGACCTATTGGCATTGGCATTGGACAAGTGGGCAAATCT
ATGGAATTGGTTTGACATATCAAAATGGCTGTGGTATATAAGAATATTTATAATGATAGTAGGAGGCTTAATAGGATTAA
GAATAGTTTTGCTGTAATTTCAGTAATAAATAGAGTTAGGCAGGAAGAAGTGGAGAGCAAGACAAGAATCGATTCGCTTAGT
AACCCAGGGGTCTGCGACAGGCCCGAAGAATCGAAGAAGAATCGAAGAAGAAGTGGAGAGCAAGACAAGAATCGATTCGCTTAGT
CAGCGGGTTCTTAGCACTTGCCTCGGAGACTGTGGAACTTCTGGGACACAGCAGTCTCAAGGGGTTGAGACTGGGGGTGGGAAGACTCAAGTAT
TGATTGCCGCGAGGACTGTGAACTCCTGTGTATTGGGGTCAGGAACTAAAATTAGTGCTATTAGTTGTTGATACCATAGCAATAGTAAT
CTGGGAATCTCCTTGTTGTATTGGGGGTCAGGAACTAAAATTAGTGCTATTAGTTGTTGATACCATAGCAATAGTAAT
AGCTGGCTGGACAGATAGGGGTCATAGAAATAGGACAAAGAATTGGTAGAGCTATTCTCAACATACCTAGAAGAATCAGGC
AGGGCGCCGAAAGGGCTTTACAATAA

Fig. 8

92US077-T8 (SEQ ID NO: 13)

ATGAGAGTGAAGGGATCAGGAAGAATTATCAGCACTTGTGGAGATGGAGTACCATGTCTGCTCCTTGGATGTTAATGAT
TTGTAGTGCTACAGAACAATTGTGGGTCACAGTCTATTATGGGTACCTGTTGGAAGAAGCAAACACCACTCTATTT
GTGCATCAGATGCTAAAGCATATGATACAGAGGCACATAATGTTTGGGCCACACATGCCTGTGTACCACAGACCCAAC
CCACAAGAAGTATTGGCAAATGTGACAGAAGATTTTAACATGTGGAAAAATAACATGTAGAACAGATGCATGAGGA
TATAATCAGTTTATGGATCAAAGCCATGTGTAAAATTAACCCCACTCTGTGTTACTTTAAATTGCACTGATG
TAAGGAATGGTACTATTGTGAGGAATAGTACTATTAGGGTCGAGGAAGGATGGAAGGAAGAAATAAAAAACTGCTCTTTC
AATGTCACCACAAGCATGAGAGACAAGTTGCAGAAAGAAGATGCATTTTTTATAAATCGATGTAATACCAATAGGTAA
TGATAATAATACTACCAGCAATAATATCACCTATACCAGCTATAGGTTGAGAAGTTGTAATACCTCAGTCATTA
CACAGGCCTGTCCAAAGATAAACTTTGAGCCAATTCCCATACATTATGTCCCGCTGGGTTGCGATTCTGAAGTGT
AATAATAGGACGTTCGAGGGAAAAGGACCATGTAAAAGATGTCAGCACAGTACAATGTACACAGTGAATTAGGCCAGTAGT
ATCAACTCAACTGCTGTTAAATGGCAGTCTGAACGAAACTGTACAAATCAATTGTACAAGACCCAACAACAATACAAGAAGAATAACT
AAGCCATAATAGTACAGCTGAACGAAACTGTACAAGAGAACATAAGAGCACATTGTAACATTAGTAAGGA
ATGGGACCAGGAAGAGTATTATACAACAGGAGACATAAGAGCACATTGTAACATTAGTAAGGA
AGATTGGAATAACACTCTAAAACAGATAGCTAAAAAATTGTGCACAGTTTAATTGTGGAGGGAATTTTCTACTGTAATACAACAAA
CATCCTCAGGAGGGACCCAGAATGGTAATGCACAGATTTAATGTCACAGTTTAATGCACAGTTTAATGCACTGTAATACAGCCTTTAAGC
CTGTTTAATAGTACTTGGGATGGTAATAAACATGTAAAATATACTGAAGGGTCAAGTAACTAACAATGAAATATCACACTTCA
ATGCAGAATAAACAAATTATAAACATGTGGCAGGAGGAGTAGGAAAAGCAATGTATGCCCCTCCCATCAGAGGACAAATTA
GATGTTCATCAACATTACAGGCTGCTATTAACAACAAGAGATGGTGGTAATACCAACGATACTAACAATACTGAGATCTTC
AGACCTGGAGGAGGAGATATGAGGGACAATTGGAGGAACAATGGAAGTGAATTATATAAAGTAGTAACATATAAAATTGAACCATTAGG
AATAGCACCCACCAAGGCAAGGCAATAGTGGTGCAAAGAGAAAAAAGAGCAATGGAATAGGAGCTCTGTTCCTTGGGT
TCTTGGGAGCAGGAAGCACTATGGGCGCAGGTCAATGAGCGCAGTCAATGACGCTGTTGCAACTCACAGTCTGGGCATCAAGCA
GTGCAACAGCAGAACAATTGTCTGGCTGTGGCTATTGAGGGCTATTGAGGGCTATTGAGGCGCAACACCATCGTTGCAACTCACAGTCTGGGCATCAAGCA
GCTCCAGGCAAGAGTCCTGGCTGTGGAAAAGATACCTAAAGGATCAACAGCTCCTGGGATTTGGGGTTGCTCTGGAAAAC
TCATTTGCACCACTGCTGTGCCTTGGAATGCTAGTTGGAGTAAATACACAAGTCTAATATACACCTTTAATTGAAGAATCGCAGAACCAACAAGAAAA
ATGCAGTGGCAGAAAGAAATTGACAATTAGATAAATGGCAAATTTGTGGAATTGGTTTGACATAACAAAATGGCTGTGGTATA
GAATGAACTAGAGTTACTAGAATTAGATAAATGGCAAATTTGTGGAATTGGTTTGACATAACAAAATGGCTGTGGTATA
TAAAATATTCATAATGATAGTAGGAGGCTTGATAGGTTTAAGAATAGTTTTGTTATACTTTCTATAGTGAATAGAGTT
AGCCAGGGATACTCACCATTATCGTTTCAGACCCGCTCCCAGCCAGGGGACCCAGAGGGGACCCCAGAGGGGAATTATATCGGGCAGGAATGAAGA
AGAAGGTGGAGGGAGAGGCAGAGACACATCCGGGACATTAGTGATGGATTCTTAGCAATTATCTGGGTCGACCTGCGA
GCCTGTCCTCTTCAGTCACCACCGCTTCAGAGAATCTCCTACAGTATTGGATTCAGGAGGATTGGAACTTCTGGGACGCAGG
GGGTGGGAAATCCTCAAGTATTGGTGGGACATTATTGGGACCAGATAGGAGGATTATAGAAGTAGCAAGAAGGAAGGACTTTTTAGAGCTTAGCTTGCT
CAACGCCACAGCCATAGCAGTGAGCTGAGGGGACAGATAGGAGGATTATAGAAGTAGCAAGAAGGACTTTTAGAGCTATTCTCC
ACATACCCTAGAAGAATAAGACAGGGCTTGGAAAGGGCTTTGCTATAA

Fig. 9

93US143-T8 (SEQ ID NO: 15)

atgagagtgaagggatcatgaaGAATTATCAGCACTTTGGAGATGGGCACCATGCTCCTGGGGTTATTGATGATCTG
TAGTGCTGCAGATCAATTGTGGGTCACAGTCTATTATGGAGTACCTGTGTGGAGTAGAAACAACCACCACTCTATTTGTG
CATCAGATGCTAAAGCATATGATAAAGAGGTACATAATGTTTGGCCACACATGCCTGTGTACCCACAGACCCAACCA
CAAGAAATACCATTGTAAATGTAACAGAAAATTTTAACATGTGGAAAATAACATGGTAGATCAAATGCATGAGGATAT
AATCAGTTTATGGGATCAAAGCCATGTGTAAAATTAACCCCACTCTGTGTTACTTTAAATTGCACTGATGATT
TGAGGAATGCTACTAATACCCACTACTAATCCAATAGTAATTGGGAGAAACCAATGGAGAAATGGAGAATAAAAACTGC
TCTTTCAAATCACCTCAAGCATAAGACATAAGAGATAAGGTACAGAAACAATATGCACTTTTTTATAGCCTTGATGTAGTACCAAT
AAAGAATAACAATAATATTAGCAATAAGATTAGATATAGGTTAAGAAGTTGTAACACCTCAGTCATTACACAGGCCTGTC
CAAAGGTAACCTTTGAGCCAATTCCCATACATTATTGTGCCCCGGCTGGTTTTGCGATTCTAAAATGTAATGATAAGAAG
TTCAATGGAACAGGACCATGTACAAATGTCAGCACAGTACAATGTACTCATGGAATTAGGCCAGTAGTATCAACTCAACT
ACTGTTAAATGGCAGTCTAGCAGAAGAAGAGGTAGTAATTCAAGACCCACAACATGCCATGAAATTTCACAGACAATGCTAAAACCATATAG
TACAACTGAAAGACCCTGTAGAAATCAATTGTACAAGACCCAACAGAAATGCATGAAAGGCATACCTATTGGAGTACCA
GGGAGAAAATTCTATGCAAGAAGAACATAACAGGAGATATAAGACAAGCATATTGTAACCTTAGTAGTAGCAAGTGAA
TAACACTTTAAAACAGATAGTTGAAAAATTACATTTTAAAATAACATTACATTTAAATTGGAGGGAATTTTCAAATAACATGTTCTGATCAAAAACTGTTAATAGT
GGGACCCAGAAATTATACTGCACAGTTTTAATTGTGGAGGGAATTTTCTATTGTAATTCAACAAAACTGTTTAATAGT
ACTTGGAATAGTACTACTGAAGGGTTAAATAACACTGGAGAAGAACCCATGCTACCAATCGTACTCCCATGCAGAATAAAGCAAATTAT
AACATGTGGCAGGAAGTAGGAAAAGCAATGTATGCCCCTCCCATCGCAGACCTAATTAGATGTCATCAATATTACAG
GGCTGCTATTAACAAGAGATGGTGGTTGATGAGAACAGCAACAGTAAAAATTGAACCCTTAGGGTAGCACCCAAGGCAAA
AGGGACAATTGGAGAAGTGAATTATATAAATATAAAAGAGCAGTGGGAATAGGAGCTGTGTTCTTGGGTTCTTGGCACAGCAGGAAGCA
GAGAAGAGTGGTGCAGAGAGAAAAAGAGCAGTGGGAATAGGAGCTGTGTTCTTGGGTTCTTGGCAACAGCAGAGCAATTTG
CTATGGGCGCAGCATCAATAACGCTGACGGTACAGGCAGCTCACAGTCTGGGCATCAAGCAGCTCCAGGCAGAGTCCTGGC
CTGAGGGCTATTGAGGCGCAACTAAAGGATCAACAGCTCCTGGGATTTTGGGGTTGCTCTGGAAAACTCATCTGCCACCACTGCTGTGC
TGTGGAAAGATACCTAAAGGATCAACAACTAACCTAACAACAACCACAAACTGGCCAAGGGGAAGAGAAATT
CTTGGAATGCTAGTTGGAGTAATAAATCAACTTAATTGAAGAAGCAATGCAAATGCACAACAACAACTGGCTGTGTATAAAAATATTCATAATGATAG
GACAATTACACAGGCTTAATATACAACTTAATTGAAGAATCGCAAAACCAACAAGAAAAGAATGAACAAGAATTATTAGC
ATTAGATAAATGGCAAGTTTGTTGACATAACAAACTGGCTGTGTATAAAAATATTCATAATGATAG
TAGGAGGCTTGATAGGTTTAAGAATAGTTTTACTGTACTTTCTATAGTGAGTTAGGCAGGGATACTTCACCATTA
TCGTTTCAGACACCACCACCACGTCCTTAGTGGATTCTTAGCAATTATCTGGTCGACTAAATTATCTGGGAAGTGCTATTAACTGCTATTAACTTGCTCAACGCCACAGCCATAGCAGT
AGACAGATCCGGTCCTTAGTGGATTCTTAGCAATTATCTGGTCGACTAAATTATCTGGTCGACTTGGAACGCCACAGCCATAGCAGT
ACCGCTTGAGAGACTTACTCTTGATTGTAACGAGGATTGTGAACTTCTGGGACCGCAGGGGTGGAAGTCCTCAAATAT
TGGTGGAATCTCCTACAGTATTGGAGTCAGGAACTAAAGAATAGTGCTATTAACTTGCTCAACGCCACAGCCATAGCAGT
AGCTGAGGGGACAGATAGGGTTATAGAAAATATTACAAAGAGCTTTTAGAGCTATTCTCCACATACCTACAAGAATAAGAC
AGGGCTTGGAAAGGGCTTTGCTATAA

Fig. 10

96USHIPS4-T8 (SEQ ID NO: 17)

ATGAGAGTGAAGGGGATCAGGAACAATTGGCAGCACTTATGGAGATGGGCACCATGCTCCTTGGAGATGTTGATGATCTG
TAGTGCTACAGAGAACAATTGTGGGTCACAGTCTATTATGGGGTTCCTGTGAGAGAAGCAACAACCACTCTATTCTGTG
CATCAGATTCTAAAGCATATGATACAGAGGCACATAATGTTGGCCACACATGCCTGTGTACCCACAGACCCAACCCA
CAAGAAGTATTATTGGAAAATGTGACAGAAAATTTTAACATGTGGAAAAATGACATGTAGAACAGATGCATGAGGATAT
AATCAGTCTATGGGATCAAAGCCTAAAGCCATGTGTAAACTAACCCACGTTGTGTTACTTTAAGTGCACTGATTATG
AGGGAAATGCTAATAATACCATTGATAATGCCACTAAAAATAGCTGGAAGGAGAAATAAAAAATTGCACTTTCAATGTC
ACCACAGCCATAAGAGATAAGGTGAAGAAACAATATGCACTTTTCATGTCTTGATGTAGTCCCAATAAAAGATGCTAA
GGATAGTAACAGCTATAGGTTGATAAGTTGTAACACCTCAGTTCTAAATGTAACAATAAGACATTCAGTGAAAGGACAA
TTCCCATATATTATTGTGCCCCGGCTGGGTTTGCGATTCTAAAGCCAGTAGCATCAACTGCTGTTAAATGGCAGTCTAGC
AAAAATGTCAGCACAGTACAATAATTAGATCTGACAATTTCACAACAATGCTAAAATCATAATAGTACAGTGAAGAACCTGTAG
AGAAGAAGAGATAATAATTGTACAAGGCCCGGCCAACAATACAAGAAAAAGTATACATATAGGACCAGGGAGAGCATGGTATGCAACAGGA
AATTAATTGTACACAAGAGATATAAGACAAGCACATTGCAACCTTAGTAGTGTAAAATGGAATAACACTTTAAGACAGATAGCTAA
GATATAATAGGAGAATAAGACAAGCACATTGCAACCTTAGTAGTGTAAAATGGAATAACACTTTAAGACAGATAGCTAA
AAAATTAGGAGAACAATTTCAGGATAAAATATAACCTTTAAGCAATCCTCAGGAGGGGACCCAGAATGTAATGCACA
GTTTTAATTGTGGGGGGGAATTTTCTACTGTAATGCAACACAACTGTTTAATAGTAGTACCTGGGATAATGTAAACATGTGGCAGAC
AACAGTACTTGGAATGAAACTGAAAACTGCCCCTCCATTATACCTATCACACTTCCCATGCAGGATAAAACAAATTGTAAACATTGTAAACATGTGGCAGAC
AGTAGGAAGACAATGTATGCCCCTCCCATTAGAGGAGAACTGAGAATCTTGTTCATCAACATAATTACAGGGCTGTCTATTAACAA
GAGATGGTGGTAATATAAATGAGACAAATGGAGTCGAGATCTTTAGACCTGCAGGAGGAGATATGAGGGACAATTGGAGA
AGTGAATTATATAAATATAAAGTAGTAAAATTGAACCATTAGAACCATTAGTAACATAGCACCCAAGGCAAAGAGAGTGGTGCA
GAGAGAAAAAGAGCAGTGGGAGTAGGAGCTATGTTCCTTGGGTCTTCTTGCAACAGCAGAACAATTGCTGAGGGCTATTGAG
CAGTGACGCTGACGGTACAGGCCAGACAATCACAGTCTGGGGCATCAAGCAGCTCCAGGCAAAACTGCTGGCTGTGGAAAGATACCT
GCGCAACATCATCTGTTGCAACTCACAGTCTGGGGGTTGCTCTGGATAAACATGACCTGGATGCAGTGGGATAAAGGAACTACTGAAATTAATCACACAGGC
AGGGGATCAACAGCTCCTGGGAATTTGGGATAAATCACTGAATTGAGGAATCGCAGAACCAGCAAGAACCTGGCTGTGGTATATCAAAACAAGGAACTACTGAATTGGATAAATGGGC
TTAATATACACCTTAATTGAGGAATCGCAGAACCAGCAAGAACCTGGCTGTGGTATATCAAAACAAGGAACTACTGAATTGGATAAATGGGC
AAGTTTGTGGAATAGTTTTACTGTACTTTCTATAGTGAATAGAGTTAGGCAGGGATACTCACCACTATCGTTTCAGACCCGC
GTTTAAGAATAGTTTTACTGTACTTTCTATAGTGAATAGAGTTAGGCAGGGATACTCACCACTATCGTTTCAGACCCGC
CTCCCAACCCAGAGGGACCCGACCAGGAATCGAAGGAATCGAAGGTGGAAGAAGGTGGAAGCCTGTGCCTCTTCAGCTACCACCGCTTGAGACT
ATCAGTGGATGGAGTTCTTAGCGAGGATTCTAGCACTTATCTGGGTCGATCTACGGAGCCTGTGCCTCTTCAGCTACCACCGCTTGAGACT
TACTCTTGATTCTGAGTCAGGAACTAAAGAATAGGTGCTGTTAGCTTGCTTAATTCTATAGCCATAGTCTAGTAGTCTGAGGGAACAGA
CAGTATTGGAGTCAGGAACTAAAGAATAGTTGCTGTTAGCTTGCTTAATTCTATAGCCATAGTCTAGTAGTCTGAGGGAACAGA
TAGGGTTATAGAAGTAGTACAGAGAGTTTGTAGAGCTATCCGCCACTATCCGCCACATACCTAGAAGAATAAGACAGGGCTTGGAAGGG
CTTTGCTATAA

Fig. 11

96USHIPS9-T8 (SEQ IS NO: 19)

atgagagTgaaggagatcatgaaaattatcagcACTGGTGGAGAGGGGCATCATGCTCCTTGGGTTGTTAATGATCTG
TAGTGCTGCTGAACAATTGTGGGTCACAGTCTATTATGGGGTACCCGTGTGGAAGAAGCAACCACTCTATTCTGTG
CATCTGATGCTAAAGCTAAATATGATACAGAGAAACATAATGTTTGGGCCACACATGCCTGTGTACTACAGACCCAACCA
CAAGAAGTAGTAGTATTGACAGAAAATTTAACATGTGAAAAATAACATGGTAGAACAGATGCATGAGGATAT
AATCAGTTTATGGGATCAAAGTCAAAGCCATGTGTAAAACTAACCCCACTCTGTGTCACTTTAAACTGTAGGAACGTTA
CTATTACCAATACTACTACCAATAGTAGTGGCTGGAAACTAATGGAGGAAGAAATAAAAAACTGCTCTTTCAAAATC
ACCACAATACTGAGACATAAGATGCAGGAAGAACATGCACTTTTTATAAATCAGATGTAGTACCACTAGTAATAATAG
TGCAATAGGTAATAATAATGCCAGATATAGGTTGATAAGTTGTAACACCTCAACCATTACACAGGCCTGTCCAAAGTAT
CCTTTGAGCCAATTCCCATACATTATTGTGCCCCGGCTGGTTTTGCGATTCTAAAATGTAGAGATAAGAAGTTCAATGA
ACAGGACCATGTAAAGATGTCAGCACAGTAATAGTAATTTAGATCTGCCAATTTCTCAGACAATGTATCAAAATCATATCAGCTGA
TGGCAGTCTAGCAGAGAAGAAGATATAGTAATTGTACAAGACCCAACAATAATACAAGAAAAGGTATAAATATAGGACCAGAAGAACAGTT
ATAAAACTGTAGTAATTAATTGTACAAGAGATATAAGAACAATGTACAATTGTAACATTGTAAAGGAGAATGTATAACACTTTAAA
TATGCAACAGGAAAAATAATAGGAGATATAAGCACATTGTAACATTGTAACATAGCTAAATAAACATAGCCTTAATAATCCTCAGGAGGGACCCAGAAA
GCAGGTAGTTACAAATTAGGAGAGAACATTTAAGAATAAAACATAGCCTTAATAATCCTCAGGAGGGACCCAGAAA
TTGTAAAGCACACTTTAATTGTGGAGGGGAATTTTTCTACTGTAATTCAACAAAATTGTTTACTAGTAGTACTTGGAACTAT
ACTAATGGTACTTGGAATAGTACTACTGAATCTGAATGATACTGAAATGTTGAATAAAACAATCACACTCCCATGCAGAATAAA
ACAAATTGTAAACATGTGGCAGGAAGTAGGGAAAGCAATGTATGCCCCTCCCATCAGCGGACTTATTACATGTTCATCAA
ATATTACAGGACTACTATTAACAAGAGATGGTGGTAGTAACAGATGGAAATGAACACCACCGAGGTCTTCAGACTGTGGAGGAGGAAAT
ATGAAGGACAATTGGAGAAGTGAATTATATAAATAAAGTAGTAACAATTAGAGTAACCATTAGGAGTAGCACCCACCAAGGC
AAAAAGAGAGTGGTGCAGAGAGAAAAAAGAGCAGGTGGAATAGGAGCAATTATTGTCTGGTTATAGTGCAGCAGACAACAAT
GCACTATGGGCGCAGCGTCACTGAGGCGCAACAGCATCTGTTGCAACAGTCTGTTGCAACTCACAGTTCAGCATCAAGCAGCTCAGCAAGAGTCCT
CTGCTGAGGGCTATTGAGGCGCAACAGCATCTGTTGCAACAGTCTGTTGGGCATCAAGCAGCTCCAGGCAAGAGTCCT
GGCTGTGAAAGATACCTAAAGGATCAACAGCTCCTGGGGATTTGGGGTTGCTCTGGAAACTCATTTGCACCACTACTG
TGCCTTGGAATGCTAGTTGGAGTAATAAATCTCTGGATGATATTTGGCAGAACATGACCTGGATGGAGTGGGAAAAGAGAA
ATTGACAATTACACAAATGTAATATACAATTTAATTGGAAGAATGCAGAATGCAGAACCAGCAAGAATGAACAAGACTTATT
AGCATTGGATAAATGGCAAGTTTGTGGAATTGGTTTAGCATATCAAACTGGCGTGTGTGGTATATAAATATTCATAATGA
TAGTAGGAGGCTTGATAGGTTTAAGAATAATTTTACTGTACTTTCTATAGTGAATGAGTTAGGCAGGATACTCACCA
TTATCGTTTCAGACCGGCTTCCCAGCCCCGAGGGACCCGAGGCCGACCCCGACAGCCCCGAAGGAATCGAAGAAGGAGGTGGAGAGAAAGA
CAGAGACAGATCCGGCTATTAGTGAACGGATCTTTGCACTTATCGGGTGGACCTACGGAGCCTGTCCTCTTCAGCT
ACCACCGCTTGAGAGATCCTGATTGCAGCGAGAATTGTGGAGCTTCGGGACGCAGGGGGTGGGAAATCCTCAAG
TATTGGTGGAATCTCCTGCAGTATTGGAGTCAGGAGAACTAAAGAATAGTGCGTGCTTAATGTCACAGCCATAGC
AGTAGCTGAGGGGACAGATAGGATTCTAGAAGTATTACAAAGAGCTTATAGAGCTATTATTCACATACCTAGAAGAATAA
GACAGGGCTTAGAAAGGGCTTTGCTATAA

Fig. 12

96USSN20 (SEQ ID NO: 21)

ATGAGAGTGAAGGGGACACAGAAGAGTTATCCACTCTTATGAGGTGGGTATAATATTTTGGATAATGTAATTTGTAA
TGCTGAAAATTTGTGGGTCACGGTCTATTATGGGGTACCGTCTGTGGAGAGACGCAGAGACCACCTTATTTTGTCATCAG
ATGCTAAAGCATATGATACAGAAGTACATAATGTTTGGGCTACACATGCCTGTGACCCACAGACCCTAACCCACAAGAA
ATACCTTTGGAAAATGTAACAGAAAATTTTAATATGTGGAAAAATAACATGGTAGAGCAGATGCATGAAGATATAATTGA
TCTATGGGACCAAAGCCAAGCCATGTGTAAAGTTAACCCCTCTGTGTTACTTTAAATTGCCATAACTTCAATAACT
TCAATAGCAGCAATAACAGCACCCTATCAACAACAAAGAAACAGTATGCACTTTTAATAAACTTGATGTAGTACAAATTAATGA
AATCACAACCAGAATTAAGAGGTAAGACAAAGAAACAGTATGCACTTTTAATAAACTTGATGTAGTACAAATTAATGA
TAAGAATAATAGTCATAGTAATAATAGACGGTATATGTTAATACATTGTAATACCTCAACCATTACACAGGCTTGTCAA
AGGTAACCTTTGAGCCAATTCCCATACATTATTGTGCCCCAGCTGGTTTTGCAATTCTAAAATGTAAGGATCAGGAGTTC
AATGGATCAGGACCATGCAACAATGTCAGCACAGTACACATGGAATCAAGCCAGTAGTATCAACTCAGCTGCT
GTTAATGGCAGTCTAGCAGAGAAAATTAATGTACCAGACCTAACAACAATATCACAAAATATCAAAAGGTTGTGTAGGCCAGGGCGA
AGTTCACTGAGCCTGTAACAAATGCCATAATAGGGGATATAAGACAAGCACAGCACATTGAATGTCAGCAGACAAATGAATGACAC
GCAGTCTATGTAACAAATGCCATAATAGGGGATATAAGACAAGCACTTAACAACAACAATAGTCTTACTAAACCTCAGGAGGGATGTGG
TTTAAAGAAGGTAGTTACACATTAACAATTAAGGAAGCACTTAACAACAACAATAGTCTTACTAAACCTCAGGAGGGATGTGG
AAATTACAACACATAGTTTTAACTGTGGAGGAGAATTTTCTATTGCAATACACACAACTGTTAATAGCACTTGGTAT
ATCAATGGCACAACCAACCACACAGGCCATATGACACTGACACTATAACTTCCGATGCAGAATAAGCAAATTGTAAAAC
ATGGCAGAGAGTAGGACAAGCAATGTATGCTCCCATCCCAGGAGTAATAAGGTGTGACTCAAACATTACAGGAATAT
TATTAACAAGAGATGGAGGGAAATTAATAGTAGTACAAATGAGACTTTCAGGCCTGGAGGAGGAGATATGAGGGACAATTGG
AGAAGTGAATTATATAAGTATAAAGTAGTAAAAATTGAACCACTAGGTGTAGCACCCATGCAAAAAGAAGAGTGGT
GGAGAGAGAAAAGAGCAGTTGGAGTAATAGGAGCTGTCTTCCTTGGGTTCTTAGGAGCAGCAGGAAGCACTATGGGCG
CAGCGGCAATAACGCTGACGGTACAGGCCAGACAATTATTGTCTGGTATAGTGCAACAGCAGAGCAAGAGAGTCCTGGCTCTGAGGCT
ATAGAGGCTCAACAGCATCTGTTGAAACTCACGTCTGGGGCATTAAAACAGCTCCAGGCAAGAGTCCATCTCTGGCTCTGAAAG
ATACCTAAGGGATCAACAGCTCCTAGGAATTTGGGGCTGCTCGTTACATATGAATAACAGCTGCACCACTAATGTACCCTGAATT
CTAGTTGGAGTAATAAAACTTTTAATGACATATGAATAACCAGCTGGTTACAATGCACCTGGTATAAAGAATTAACAATTAC
ACAAACCACAATATCGTCTAATTGAAGAATCGCAGAACCAGGAGAAATCGCAGAAAGATTAAGAATTTATTGGCATTGGACAA
GTGGGCAAGTCTGTGAGTTGGTTTTGACCTATCAAATTGGCTATGTATAATAAGAATATTTATAATGTAGTAGGAGGTT
TGATAGCTTTAAGAATAGTTTTTGCTGGTGCTTGCTGCTATAATAAATAGAGTTAGGCAGGGATACTCACCTCTATCATTCCAG
ACCCTTACCCACCACCAGAGGAACCCGACAGGCCCGAAGGAATCGAAGAAGGAGGTGGCGAGCAAGACAGAGACAGGTC
CGTGAGATTAGTGAACGGATTCTTAGCTCTTGCCTGGGACGATCTACGGACGACATCGACCACCGATTGA
GAGACTTACTCTTGATTGCAGCGAGGACTGTGGAACTTCTGGGACACAGCAGTCTCAAGGGACTGGACTGTGGGGA
GCCCTCAAATATCTGTGGAATCTTCTGTCATACTGGGGCAGGAACTCAAGATAGTGCTATTAATCTGCTTGATACAAC
AGCAATAGCAGTAGCTAATTGGACAGACAGAGTTATAGAAGAAATAGGACAAAGATTTGGTAGAGCTATTCTCAATATACCTA
GAAGAATCAGACAGGGCCTCGAAGGGCTTTGCAATAA

Fig. 13

SEQUENCE LISTING

<160> NUMBER OF SEQ ID NOS: 27

<210> SEQ ID NO 1
<211> LENGTH: 2610
<212> TYPE: DNA
<213> ORGANISM: HIV-1

<400> SEQUENCE: 1

```
atgagagtga aggggatcag gaggaattat cagcacttgt ggagatgggg caccatgctc      60
cttgggatgt tgatgatctg tagtgctgca gatcaattgt gggtcacagt ctattatggg     120
gtgcctgtgt ggaaagaagc aaccaccact ctattttgtg catcagatgc taaagcatat     180
agtacagagg tacataatat ttgggccaca catgcctgtg tacccacaga ccccagccca     240
caagaaatag taatggaaaa tgtgacagaa gagttcaaca tgtggaaaaa taacatggta     300
gaacagatgc atgaggatat aatcagttta tgggatgaaa gcctaaagcc atgtgtaaaa     360
ttaactccac tctgtgttac tctaaattgc actactgagt tgaatcttct aaattgcatt     420
gataatagta ctaatgataa atgtataccg ccagatcaaa aaggagaaat gaaaaactgc     480
tctttcaata tcaccgcagg cataagaaat aaggtgcgga aagaatatgc acttttttat     540
acaagtgatg tagcaccaat agataatgat actatcagtt atagattgat aagttgtaac     600
acctcaatca ttacacaggc ctgtccaaag gtatcctttg agccaattcc catacactat     660
tgtgccccgg ctggttttgc gattctaaag tgtaaggata ggaatttcaa tggaacagga     720
ctatgtaaaa atgtcagcac agtacaatgt acacatggaa ttaggccagt agtatcaact     780
caactgctgt taaatggcag tctggcagaa aaagagatag taattagatc tgaaaatttc     840
acggacaatg ctaaaaccat aatagtacag ctgcctgaaa tagtacacat taattgtaca     900
agacctaaca ataatataag aaaaggtcta cgtataggac cagggagagc atggtggtat     960
gcaacaagag gaataatagg aaaaatgaga caaacacatt gcaacattag tagagtaaaa    1020
tggaataaca ctttagaaca gatagttaaa aaattaggag acaaatttgg gactaataat    1080
aataaaacaa taatatttaa tcaatcctca ggaggggacc cagaaattac aatgcacact    1140
tttaattgtg gaggggaatt tttttactgt aatacaacac aactgtttaa tagtacttgg    1200
attcggaatg gtactgattg gactcgaaat gatactgaag gatcagacat cactaacgaa    1260
aatatcacgc tcccatgtag aataaaacaa attataaaca tgtggcagaa agtagggaaa    1320
```

-continued

```
gcaatgtatg cccctcccat cagtggacaa attagctgtt cctcaaatat tacagggctg    1380
ctattaacac acgatggtgt tgttggtctg tacacggacg cgaacaacgt gaccttcaga    1440
ccggggaggag gaaatatgag ggacaattgg agaagtgaat tatataaata taaagtaata    1500
aaagttgaac caataggaat agcacccacc aaggcaaaga gaagagtggt gcagagagaa    1560
aaaagagcag tgggaatagg agctatgttc cttgggttct tgggaacagc aggaagcgct    1620
atgggcgcag cgtcagtgac gctgacggta caagccagac aattattgtc tggtatagtg    1680
caacagcaga acaatctgct gagggctatt gaggcgcaac agcatatgtt gcaactcaca    1740
gtctggggca tcaagcagct ccaggcaaga gtcctggctg tggaaagata cctaagggat    1800
caacagctcc tggaatttg gggttgctct ggaaaactca tttgcaccac tgctgtgcct    1860
tggaatagta gttggagtaa tagatctctg ggagacattt gggaaaatga taacatgacc    1920
tggatgaagt gggaaagaga aattgataat tacacaagct atatatacac cttaattgaa    1980
gaatcgcaga accagcaaga aaagaatgaa ctagaattat tggaattaga caaatgggac    2040
agtttgtgga gttggtttag cataacaaac tggctgtggt atataaaaat attcataatg    2100
atagtaggag gcttgatagg tttaagaata gttttagtg tgctttctat agtgaataga    2160
gttaggcagg gatactcacc attgtcgttt cagacccggc ccccagcccc gaggggaccc    2220
gacaggcccg aaggaatcga agaagaaggt ggagagagag acagagacag atccggcaga    2280
ttagtggatg gattcttagc acttatctgg gtcgacctgc ggagcctgtg cctcttcagc    2340
taccaccgct tgagagactt actcttgatt gcagcgagga ttgtggaact cctgggacgc    2400
agggggtggg aagtcctcaa gtattgttgg aatctcctac agtactggag tcaggaacta    2460
aagaatagtg ctgttagctt gcttaatacc atagcaatag cagtagctga ggggacagat    2520
aggttatag aaataataca aagagcttgt agagctattc tccacatacc tagaagaata    2580
agacagggct tgaaagggc tttgctataa                                      2610
```

<210> SEQ ID NO 2
<211> LENGTH: 477
<212> TYPE: PRT
<213> ORGANISM: HIV-1

<400> SEQUENCE: 2

```
Met Arg Val Lys Gly Ile Arg Arg Asn Tyr Gln His Leu Trp Arg Trp
  1               5                  10                  15
Gly Thr Met Leu Leu Gly Met Leu Met Ile Cys Ser Ala Ala Asp Gln
             20                  25                  30
Leu Trp Val Thr Val Tyr Tyr Gly Val Pro Val Trp Lys Glu Ala Thr
         35                  40                  45
Thr Thr Leu Phe Cys Ala Ser Asp Ala Lys Ala Tyr Ser Thr Glu Val
     50                  55                  60
His Asn Ile Trp Ala Thr His Ala Cys Val Pro Thr Asp Pro Ser Pro
 65                  70                  75                  80
Gln Glu Ile Val Met Glu Asn Val Thr Glu Glu Phe Asn Met Trp Lys
                 85                  90                  95
Asn Asn Met Val Glu Gln Met His Glu Asp Ile Ile Ser Leu Trp Asp
            100                 105                 110
Glu Ser Leu Lys Pro Cys Val Lys Leu Thr Pro Leu Cys Val Thr Leu
        115                 120                 125
Asn Cys Thr Thr Glu Leu Asn Leu Leu Asn Cys Ile Asp Asn Ser Thr
    130                 135                 140
```

```
Asn Asp Lys Cys Ile Pro Pro Asp Gln Lys Gly Glu Met Lys Asn Cys
145                 150                 155                 160

Ser Phe Asn Ile Thr Ala Gly Ile Arg Asn Lys Val Arg Lys Glu Tyr
                165                 170                 175

Ala Leu Phe Tyr Thr Ser Asp Val Ala Pro Ile Asp Asn Asp Thr Ile
            180                 185                 190

Ser Tyr Arg Leu Ile Ser Cys Asn Thr Ser Ile Ile Thr Gln Ala Cys
        195                 200                 205

Pro Lys Val Ser Phe Glu Pro Ile Pro Ile His Tyr Cys Ala Pro Ala
    210                 215                 220

Gly Phe Ala Ile Leu Lys Cys Lys Asp Arg Asn Phe Asn Gly Thr Gly
225                 230                 235                 240

Leu Cys Lys Asn Val Ser Thr Val Gln Cys Thr His Gly Ile Arg Pro
                245                 250                 255

Val Val Ser Thr Gln Leu Leu Leu Asn Gly Ser Leu Ala Glu Lys Glu
            260                 265                 270

Ile Val Ile Arg Ser Glu Asn Phe Thr Asp Asn Ala Lys Thr Ile Ile
        275                 280                 285

Val Gln Leu Pro Glu Ile Val His Ile Asn Cys Thr Arg Pro Asn Asn
    290                 295                 300

Asn Ile Arg Lys Gly Leu Arg Ile Gly Pro Gly Arg Ala Trp Trp Tyr
305                 310                 315                 320

Ala Thr Arg Gly Ile Ile Gly Lys Met Arg Gln Thr His Cys Asn Ile
                325                 330                 335

Ser Arg Val Lys Trp Asn Asn Thr Leu Glu Gln Ile Val Lys Lys Leu
            340                 345                 350

Gly Asp Lys Phe Gly Thr Asn Asn Lys Thr Ile Ile Phe Asn Gln
        355                 360                 365

Ser Ser Gly Gly Asp Pro Glu Ile Thr Met His Thr Phe Asn Cys Gly
    370                 375                 380

Gly Glu Phe Phe Tyr Cys Asn Thr Thr Gln Leu Phe Asn Ser Thr Trp
385                 390                 395                 400

Ile Arg Asn Gly Thr Asp Trp Thr Arg Asn Asp Thr Glu Gly Ser Asp
                405                 410                 415

Ile Thr Asn Glu Asn Ile Thr Leu Pro Cys Arg Ile Lys Gln Ile Ile
            420                 425                 430

Asn Met Trp Gln Lys Val Gly Lys Ala Met Tyr Ala Pro Pro Ile Ser
        435                 440                 445

Gly Gln Ile Ser Cys Ser Ser Asn Ile Thr Gly Leu Leu Leu Thr His
    450                 455                 460

Asp Gly Val Val Gly Leu Tyr Thr Asp Ala Asn Val
465                 470                 475

<210> SEQ ID NO 3
<211> LENGTH: 2652
<212> TYPE: DNA
<213> ORGANISM: HIV-1

<400> SEQUENCE: 3
atgagagtga aggggatcag gaagaattat cagcacttgt ggagatgggg caccatactc      60
cttgggatgt tgatgatctg tagtgctgca gatcaattgt gggtcacagt ctattatggg     120
gtgcctgtgt ggaaagaagc aaccaccact ctattttgtg catcagatgc taaagcatat     180
agtacagagg tacataatat ttgggccaca catgcctgtg tacccacaga ccccagccca     240
```

```
caagaaatag taatggaaaa tgtgacagaa gagttcaaca tgtggaaaaa taacatggta        300
gaacagatgc atgaggatat aatcagttta tgggatgaaa gcctaaagcc atgtgtaaaa        360
ttaactccac tctgtgttac tctaaattgc actactgagt tgaatcttct aaattgcatt        420
gataatagta ctagtggtaa taacactgat aatagcacta gtagtaatag tactgatgat        480
aaatgtatac cgccagatca aaaggaaaa atgaaaaact gctctttcaa tatcaccgca         540
ggcataagag ataaggtgcg gaaagaatat gcactttttt atacaagtga tgtagcacca        600
atagataatg atgctatcag ttatagattg ataagttgta acacctcaat cattacacag        660
gcctgtccaa aggtatcctt tgagccaatt cccatacact attgtgcccc ggctggtttt        720
gcgattctaa agtgtaagga taggaatttc aatggaacag gactatgtaa aaatgtcagc        780
acagtacaat gtacacatgg aattaggcca gtagtatcaa ctcaactgct gttaaatggc        840
agtctggcaa aaaagagat agtaattaga tctgaaaatt tcacggacaa tgctaaaacc         900
ataatagtac agctgcctga aatagtacac attaattgta caagacctaa caataatata        960
agaaaaggtc tacgtatagg accagggaga gcatggtggt atgcaacaag aggaataata       1020
ggaaaaatga cacaaacaca ttgcaacatt agtagagaaa aatggaataa cactttagaa       1080
cagatagtta aaaaattagg agacaaattt gggactaata ataataaaac aataatattt       1140
aatcaatcct caggagggga cccagaaatt acaatgcaca cttttaattg tggaggggaa       1200 ttttttttact gtaatacaac acaactgttt aatagtactt ggattcggaa tggtactgat      1260
tggactcaaa atgatactga aggatcagac atcactaacg aaaatatcac gctcccatgt       1320
agaataaaac aaattataaa catgtggcag gaagtaggga aagcaatgta tgcccctccc       1380
atcagtggac aaattagctg ttcatcaaat attacagggc tgctattaac acacgatggt       1440
gttgttggtc tgtacacgaa cgcgaacaac gtgaccttca gaccgggagg aggaaatatg       1500
agggacaatt ggagaagtga attatataaa tataaagtaa taaagttga accaatagga       1560 atagcaccca ccaaggcaaa gagaagagtg gtgcagagag aaaaaagagc agtgggaata       1620
ggagctatgt tccttgggtt cttgggaaca gcaggaagcg ctatgggcgc agcgtcagtg       1680
acgctgacgg tacaagccag acaattattg tctggtatag tgcaacagca gaacaatctg       1740
ctgagggcta ttgaggcgca acagcatatg ttgcaactca cagtctgggg catcaagcag       1800
ctccaggcaa gagtcctggc tgtggaaaga tacctaaggg atcaacagct cctgggaatt       1860
tggggttgct ctggaaaact catttgcacc actgctgtgc cttggaatag tagttggagt       1920
aatagatctc tgggagacat ttgggaaaat gataacatga cctggatgaa gtgggaaaga       1980
gaaattgata attacacaag ctatatatac accttaattg aagaatcgca gaaccagcaa       2040
gaaaagaatg aactagaatt attggaatta gacaaatggg acagtttgtg gagttggttt       2100
agcataacaa actggctgtg gtatataaaa atattcataa tgatagtagg aggcttgata       2160
ggtttaaaaa tagttttttag tgtgctttct atagtgaata gagttaggca gggatactca       2220
ccattgtcgt tcagacccg gcccccagcc ccgagggac ccgacaggcc cgaaggaatc         2280
gaagaagaag gtggagagag agacagagac agatccggca gattagtgga tggattctta       2340
gcacttatct gggtcgacct gcggagcctg tgcctcttca gctaccaccg cttgagagac       2400
ttactcttga ttgcagcgag gattgtggaa ctcctggacg cagggggtg ggaagtcctc        2460 aagtattgtt ggaatctcct acagtactgg agtcaggaac taagaatag tgctgttagc       2520 ttgcttaata ccatagcaat agcagtagct gaggggacag ataggttat agaaataata      2580
```

```
caaagagctt gtagagctat tctccacata cctagaagaa taagacaggg ctttgaaagg    2640
gctttgctat aa                                                        2652
```

<210> SEQ ID NO 4
<211> LENGTH: 491
<212> TYPE: PRT
<213> ORGANISM: HIV-1

<400> SEQUENCE: 4

```
Met Arg Val Lys Gly Ile Arg Lys Asn Tyr Gln His Leu Trp Arg Trp
1               5                  10                  15
Gly Thr Ile Leu Leu Gly Met Leu Met Ile Cys Ser Ala Ala Asp Gln
            20                  25                  30
Leu Trp Val Thr Val Tyr Tyr Gly Val Pro Val Trp Lys Glu Ala Thr
        35                  40                  45
Thr Thr Leu Phe Cys Ala Ser Asp Ala Lys Ala Tyr Ser Thr Glu Val
    50                  55                  60
His Asn Ile Trp Ala Thr His Ala Cys Val Pro Thr Asp Pro Ser Pro
65                  70                  75                  80
Gln Glu Ile Val Met Glu Asn Val Thr Glu Gly Phe Asn Met Trp Lys
                85                  90                  95
Asn Asn Met Val Glu Gln Met His Glu Asp Ile Ile Ser Leu Trp Asp
            100                 105                 110
Glu Ser Leu Lys Pro Cys Val Lys Leu Thr Pro Leu Cys Val Thr Leu
        115                 120                 125
Asn Cys Thr Thr Glu Leu Asn Leu Leu Asn Cys Ile Asp Asn Ser Thr
    130                 135                 140
Ser Gly Asn Asn Thr Asp Asn Ser Thr Ser Asn Ser Thr Asp Asp
145                 150                 155                 160
Lys Cys Ile Pro Pro Asp Gln Lys Gly Lys Met Lys Asn Cys Ser Phe
                165                 170                 175
Asn Ile Thr Ala Gly Ile Arg Asp Lys Val Arg Lys Glu Tyr Ala Leu
            180                 185                 190
Phe Tyr Thr Ser Asp Val Ala Pro Ile Asp Asn Asp Ala Ile Ser Tyr
        195                 200                 205
Arg Leu Ile Ser Cys Asn Thr Ser Ile Ile Thr Gln Ala Cys Pro Lys
    210                 215                 220
Val Ser Phe Glu Pro Ile Pro Ile His Tyr Cys Ala Pro Ala Gly Phe
225                 230                 235                 240
Ala Ile Leu Lys Cys Lys Asp Arg Asn Phe Asn Gly Thr Gly Leu Cys
                245                 250                 255
Lys Asn Val Ser Thr Val Gln Cys Thr His Gly Ile Arg Pro Val Val
            260                 265                 270
Ser Thr Gln Leu Leu Asn Gly Ser Leu Ala Lys Lys Glu Ile Val
        275                 280                 285
Ile Arg Ser Glu Asn Phe Thr Asp Asn Ala Lys Thr Ile Ile Val Gln
    290                 295                 300
Leu Pro Glu Ile Val His Ile Asn Cys Thr Arg Pro Asn Asn Ile
305                 310                 315                 320
Arg Lys Gly Leu Arg Ile Gly Pro Gly Arg Ala Trp Trp Tyr Ala Thr
                325                 330                 335
Arg Gly Ile Ile Gly Lys Met Arg Gln Thr His Cys Asn Ile Ser Arg
            340                 345                 350
Glu Lys Trp Asn Asn Thr Leu Glu Gln Ile Val Lys Lys Leu Gly Asp
```

```
                355                 360                 365
Lys Phe Gly Thr Asn Asn Lys Thr Ile Ile Phe Asn Gln Ser Ser
        370                 375                 380
Gly Gly Asp Pro Glu Ile Thr Met His Thr Phe Asn Cys Gly Gly Glu
385                 390                 395                 400
Phe Phe Tyr Cys Asn Thr Thr Gln Leu Phe Asn Ser Thr Trp Ile Arg
                405                 410                 415
Asn Gly Thr Asp Trp Thr Gln Asn Asp Thr Glu Gly Ser Asp Ile Thr
            420                 425                 430
Asn Glu Asn Ile Thr Leu Pro Cys Arg Ile Lys Gln Ile Ile Asn Met
            435                 440                 445
Trp Gln Glu Val Gly Lys Ala Met Tyr Ala Pro Pro Ile Ser Gly Gln
        450                 455                 460
Ile Ser Cys Ser Ser Asn Ile Thr Gly Leu Leu Leu Thr His Asp Gly
465                 470                 475                 480
Val Val Gly Leu Tyr Thr Asn Ala Asn Asn Val
                485                 490

<210> SEQ ID NO 5
<211> LENGTH: 2571
<212> TYPE: DNA
<213> ORGANISM: HIV-1

<400> SEQUENCE: 5
atgagagtga aggagaaata tcagcacttg tggagatggg ggtggagatg gggcaccatg      60
ctccttggga tgttgatgat ctgtagtgct acagaaaaat tgtgggtcac agtctattat     120
ggggtacctg tgtggaagga agcaaccacc actctatttt gtgcatcaaa tgctaaagca     180
tataatacag aggtacataa tgtttgggcc acacatgcct gtgtgcccac agaccccaac     240
ccacaagaag tagtattggt aaatgtgaca gaaaatttta acatgtggaa aaatgacatg     300
gtagaataca tgcatgagga tataatcagt ttatgggatc aaagcctaaa gccatgtgta     360
aaattaaccc cactctgtgt tagtttaaag tgcactgatt tgaagaatga tactaatacc     420
aatagtagta gcgggagaat gataatggag aaaggagaga taaaaaactg ctctttcaat     480
atcagcacaa gcataagagg taaggtgcag aaagaatatg catttttta taaacttgat     540
ataataccaa tagataatga tactaccagc tataagttga caagttgtaa caccctcagtc    600
attacacagg cctgtccaaa ggtatccttt gagccaattc ccatacatta ttgtgccccg     660
gctggttttg cgattctaaa atgtaataat aagacgttca atggaacagg accatgtaca     720
aatgtcagca cagtacaatg tacacatgga attaggccag tagtatcaac tcaactgctg     780
ttaaatggca gtctagcaga agaagaggta gtaattagat ctgtcaattt cacggacaat     840
gctaaaacca atatagtaca gctgaacaca tctgtagaaa ttaattgtac aagacccaac     900
aacaatacaa gaaaagaat ccgtatccag agaggaccag ggagagcatt tgttacaata     960
ggaaaaatag gaaatataag acaagcacat tgtaacatta gtagagcaaa atggaataac    1020
actttaaaac agatagctag caaattaaga gaacaatttg gaataataa acaataatc    1080
tttaagcaat cctcaggagg ggacccagaa attgtaacgc acagttttaa ttgtggaggg    1140
gaattttct actgtaattc aacacaactg tataatagta cttggtttaa tagtacttgg    1200
agtactgaag ggtcaaataa cactgaagga agtgacacaa tcaccctccc atgcagaata    1260
aaacaaatta taaacatgtg gcagaaagta ggaaaagcaa tgtatgcccc tcccatcagt    1320
ggacaaatta gatgttcatc aaatattaca gggctgctaa taacaagaga tggtggtaat    1380
```

-continued

```
agcaacaatg agtccgagat cttcagacct ggaggaggag atatgagggg caattggaga   1440
agtgaattat ataaatataa agtagtaaaa attgaaccat taggagtagc acccaccaag   1500
gcaaagagaa gagtggtgca gagagaaaaa agagcagtgg aataggagc tttgttcctt    1560 gggttcttgg gagcagcagg aagcactatg ggcgcggcgt caatgacgct gacggtacag   1620
gccagacaat tattgtctgg tatagtgcag cagcagaaca atttgctgag ggctattgag   1680
gcgcaacagc atctgttgca actcacagtc tggggcatca agcagctcca ggcaagaatc   1740
ctggctgtgg aaagatacct aaaggatcaa cagctcctgg ggatttgggg ttgctctgga   1800
aaactcattt gcaccactgc tgtgccttga atgctagtt ggagtaataa atctctggaa    1860
cagatttgga atcacacgac ctggatggag tgggacagag aaattaacaa ttacacaagc   1920
ttaatacact ccttaattga agaatcgcaa aaccagcaag aaaagaatga acaagaatta   1980
ttggaattag ataatgggc aagtttgtga aattggttta acataacaaa ttggctgtgg    2040
tatataaaat tattcataat aatagtagaa ggcttggtag gtttaagaat agttttgct    2100 gtactttcta tagtaatag agttaggcag ggatattaac cattatcgtt tcagacccac    2160
ctcccaaccc cgaggggacc cgacaggccc gaaggaatag aagaagaagg tggagagaga   2220
gacagagaca gatccattcg attagtgaac ggatccttgg cacttatctg ggacgatctg   2280
cggagcctgt gcctcttcag ccaccaccgc ttgagagact tactcttgat tgtaacgagg   2340
attgtggaac ttctgggacg cagggggtgg aagtcctca aatattggtg aatctccta     2400 cagtattgaa gtcaggaact aaagaatagt gctgttagct tgctcaatgc cacagccata   2460
gcagtagctg aggggacaga tagggttata gaagtagtac aaggagcttg tagagcgatt   2520
cgccacatac ctagaagaat aagacagggc ttggaaagga ttttgctata a            2571
```

<210> SEQ ID NO 6
<211> LENGTH: 491
<212> TYPE: PRT
<213> ORGANISM: HIV-1

<400> SEQUENCE: 6

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160
```

```
Ile Ser Thr Ser Ile Arg Gly Lys Val Gln Lys Glu Tyr Ala Phe Phe
            165                 170                 175
Tyr Lys Leu Asp Ile Ile Pro Ile Asp Asn Asp Thr Thr Ser Tyr Lys
        180                 185                 190
Leu Thr Ser Cys Asn Cys Ala Pro Ala Gly Phe Ala Ile Leu Lys Cys
    195                 200                 205
Asn Asn Lys Thr Phe Asn Gly Thr Gly Pro Cys Thr Asn Val Ser Thr
210                 215                 220
Val Gln Cys Thr His Gly Ile Arg Pro Val Val Ser Thr Gln Leu Leu
225                 230                 235                 240
Leu Asn Gly Ser Leu Ala Glu Glu Val Val Ile Arg Ser Val Asn
            245                 250                 255
Phe Thr Asp Asn Ala Lys Thr Ile Ile Val Gln Leu Asn Thr Ser Val
                260                 265                 270
Glu Ile Asn Cys Thr Arg Pro Asn Asn Asn Thr Arg Lys Arg Ile Arg
            275                 280                 285
Ile Gln Arg Gly Pro Gly Arg Ala Phe Val Thr Ile Gly Lys Ile Gly
        290                 295                 300
Asn Met Arg Gln Ala His Cys Asn Ile Ser Arg Ala Lys Trp Asn Asn
305                 310                 315                 320
Thr Leu Lys Gln Ile Ala Ser Lys Leu Arg Glu Gln Phe Gly Asn Asn
                325                 330                 335
Lys Thr Ile Ile Phe Lys Gln Ser Ser Gly Gly Asp Pro Glu Ile Val
            340                 345                 350
Thr His Ser Phe Asn Cys Gly Gly Glu Phe Phe Tyr Cys Asn Ser Thr
        355                 360                 365
Gln Leu Phe Asn Ser Thr Trp Phe Asn Ser Thr Trp Ser Thr Glu Gly
    370                 375                 380
Ser Asn Asn Thr Glu Gly Ser Asp Thr Ile Thr Leu Pro Cys Arg Ile
385                 390                 395                 400
Lys Gln Ile Ile Asn Met Trp Gln Lys Val Gly Lys Ala Met Tyr Ala
                405                 410                 415
Pro Pro Ile Ser Gly Gln Ile Arg Cys Ser Ser Asn Ile Thr Gly Leu
            420                 425                 430
Leu Leu Thr Arg Asp Gly Gly Asn Ser Asn Asn Glu Ser Glu Ile Phe
        435                 440                 445
Arg Pro Gly Gly Gly Asp Met Arg Asp Asn Trp Arg Ser Glu Leu Tyr
    450                 455                 460
Lys Tyr Lys Val Val Lys Ile Glu Pro Leu Gly Val Ala Pro Thr Lys
465                 470                 475                 480
Ala Lys Arg Arg Val Val Gln Arg Glu Lys Arg
                485                 490

<210> SEQ ID NO 7
<211> LENGTH: 2580
<212> TYPE: DNA
<213> ORGANISM: HIV-1

<400> SEQUENCE: 7
atgagagtga agggatcag gaagaattat cagcacttgt ggaatgggg catcatgctc      60 cttgggatat tgatgatctg tagtgctgca gaaaacttgt gggtcacagt ctattatggg   120
gtacctgtgt ggaaagaagc aaccaccact ctattttgtg catcagatgc taaagcatat   180
gatacagaag tacataatgt ttgggccaca catgcctgtg tacccacaga ccccaaccca   240
```

```
caagaagtag tattggaaaa tgtgacagaa aattttaaca tgtggaaaaa taacatggta      300
gaacagatgc atgaagatat aattagttta tgggatcaaa gcctaaaacc atgtgtaaaa      360
ttaaccccac tctgtgttac tttaaattgc actaatgtga atgtgactaa tttgaagaat      420
gagactaata ccaatagtag tagtggaggg gaaaagatgg aggagggaga atgaaaaac       480 tgctctttca atgtcaccac actcataaga aataagagaa agactgaata tgcacttttt      540
tataaacttg atgtaatgcc aatagatcat gataatacaa gctatacgtt gataaattgt      600
aaatcctcaa ccattacaca ggcctgtcca aggtatcct ttgaaccaat tcccatacat       660
tattgtgccc cggctggttt tgcgattcta agtgtaatg ataagaagtt caatggaaag       720
ggaccctgta aaaatgtcag cacagtacaa tgtacacacg gaattagacc agtagtgtca      780
acccaattgc tgttaaatgg cagtctagca gaagaagaca tagtaattag atctgaaaat      840
ttcacggaca atgctaaaaa cataatagta cagctgaatg tatccataga aattaattgt      900
acaagaccca caacaatac aagaaaaaaa ataactttag gaccagggag agtactttat       960
acaacaggag aaataatagg agatataaga cgagcacatt gtaaccttag tagaacaagt     1020
tggaataaca ctttaaaaca gatagttgaa aaattaagag aaataaaaca atttaagaat     1080
aaaacaatag ttttaaaaca atcctcagga ggggacccag aaattgtaat gcacagtttt     1140
aattgtggag gggaatttttc tactgtaat tcaacacagc tgtttaatag tacttggcat     1200
gctaatggta cttggaagaa tactgaaggg gcagataaca atatcacact cccatgcaga     1260
ataaaacaaa ttataaacag gtggcaggaa gtaggaaaag caatgtatgc cccacccatc     1320
gaaggacaaa ttagatgttt atcaaatatt acaggttac tattaacaag atggtggt       1380 agtagtgaag agaaccagac cgagatcttc agacctggag gaggaaatat gaaggataat     1440
tggagaagtg aattatataa atataaagta gtaaaaattg aaccattagg agtagcaccc     1500
accaaggcaa agagaagagt ggtgcagaga gaaaaaagag cagtgggaat gctaggagct     1560
atgttccttg ggttcttggg agcagcagga agcactatgg gcgcagcgtc aatgacgctg     1620
acggtacagg ccagactatt attgtctggt atagtgcaac agcagaacaa tctgctgagg     1680
gctattgagg cgcaacagca tctgttcgaa ctcacagtct ggggcatcaa acagctccag     1740
gcaagagtcc tggctgtgga agataccta aaggatcagc agctcctggg gatttggggt     1800
tgctctggaa aactcatctg caccactact gtgccttgga atgctagttg gagtaataga     1860
tctcaggatt acatttggaa taacatgacc tggatggagt gggagagaga attaacaat      1920 tacacaggct aatatacaa cttaattgaa gaatcgcaga accaacaaga aaaaaatgag      1980
caagaattat tggaattgga taatgggca agtttgtgga cttggtttga catatcaaac      2040
tggctgtggt atataaaaat cttcataatg atagtaggag gcttgatagg tttaagaata      2100 gttttactg tactttccat agtaaataga gttaggcagg gatactcacc attgtcattt      2160
cagacccacc tcccagcccc gagggggaccc gacaggcccg aaggaatcga agaagaaggt    2220
ggagagagag acagagacag atccggaaga ttagtggatg gattcttaac acttatctgg     2280
gtcgacctac ggagcctgtg cctcttcctc taccaccgct tgatcgactt actcttgatt     2340
gcaaagagga ttgtggaact tctgggacgc aggggtggg aagctctcaa atattgttgg      2400
aatctcctgc agtattggag ccaggaacta agaatagtg ctgttagttt gcttaatgcc      2460
acagctatag cagtagctga ggggacagat agggttatag aaatagtgca agaacttgt      2520 agagctattc tccacatacc tagaagaata agacagggct tagaaagggc tttgctataa     2580
```

<210> SEQ ID NO 8
<211> LENGTH: 467
<212> TYPE: PRT
<213> ORGANISM: HIV-1

<400> SEQUENCE: 8

```
Met Arg Val Lys Gly Ile Arg Lys Asn Tyr Gln His Leu Trp Lys Trp
1               5                   10                  15

Ile Met Leu Leu Gly Ile Leu Met Ile Cys Ser Ala Ala Glu Asn Leu
            20                  25                  30

Trp Val Thr Val Tyr Tyr Gly Val Pro Val Trp Lys Glu Ala Thr Thr
        35                  40                  45

Thr Leu Phe Cys Ala Ser Asp Ala Lys Ala Tyr Asp Thr Glu Val His
    50                  55                  60

Asn Val Trp Ala Thr His Ala Cys Val Pro Thr Asp Pro Asn Pro Gln
65                  70                  75                  80

Glu Val Val Leu Glu Asn Val Thr Glu Asn Phe Asn Met Trp Lys Asn
                85                  90                  95

Asn Met Val Glu Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asn Val Asn Val Thr Asn Leu Lys Asn Glu Thr Asn Thr Asn
    130                 135                 140

Ser Ser Ser Gly Gly Glu Lys Met Glu Glu Gly Glu Met Lys Asn Cys
145                 150                 155                 160

Ser Phe Asn Val Thr Thr Leu Ile Arg Asn Lys Arg Lys Thr Glu Tyr
                165                 170                 175

Ala Leu Phe Tyr Lys Leu Asp Val Met Pro Ile Asp Arg Asp Asn Thr
            180                 185                 190

Ser Tyr Thr Leu Ile Asn Cys Lys Ser Ser Thr Ile Thr Gln Ala Cys
        195                 200                 205

Pro Lys Val Ser Phe Glu Pro Ile Pro Ile His Tyr Cys Ala Pro Ala
    210                 215                 220

Gly Phe Ala Ile Leu Lys Cys Asn Asp Lys Lys Phe Asn Gly Lys Gly
225                 230                 235                 240

Pro Cys Lys Asn Val Ser Thr Val Gln Cys Thr His Gly Ile Arg Pro
                245                 250                 255

Val Val Ser Thr Gln Leu Leu Leu Asn Gly Ser Leu Ala Glu Glu Asp
            260                 265                 270

Ile Val Ile Arg Ser Glu Asn Phe Thr Asp Asn Ala Lys Asn Ile Ile
        275                 280                 285

Val Gln Leu Asn Val Ser Leu Glu Ile Asn Cys Thr Arg Pro Asn Asn
    290                 295                 300

Asn Thr Arg Lys Lys Ile Thr Leu Gly Arg Ser Arg Val Leu Tyr Thr
305                 310                 315                 320

Thr Gly Glu Ile Ile Gly Asp Ile Arg Arg Ala His Cys Asn Leu Ser
                325                 330                 335

Arg Thr Ser Trp Asn Asn Thr Leu Lys Gln Ile Val Glu Lys Leu Arg
            340                 345                 350

Glu Ile Lys Gln Phe Lys Asn Lys Thr Ile Val Phe Lys Gln Ser Ser
        355                 360                 365

Gly Gly Asp Phe Glu Ile Val Met His Ser Phe Asn Cys Gly Gly Glu
    370                 375                 380
```

```
Phe Phe Tyr Cys Asn Ser Thr Gln Leu Phe Asn Ser Thr Trp His Ala
385                 390                 395                 400

Asn Gly Thr Trp Lys Asn Thr Glu Gly Ala Asp Asn Asn Ile Thr Leu
            405                 410                 415

Pro Cys Arg Ile Lys Gln Ile Ile Asn Arg Trp Gln Glu Val Gly Lys
        420                 425                 430

Ala Met Tyr Ala Pro Pro Ile Glu Gly Gln Ile Arg Cys Leu Ser Asn
    435                 440                 445

Ile Thr Gly Leu Leu Leu Thr Arg Asp Gly Gly Ser Ser Glu Glu Asn
    450                 455                 460

Gln Thr Glu
465

<210> SEQ ID NO 9
<211> LENGTH: 2553
<212> TYPE: DNA
<213> ORGANISM: HIV-1

<400> SEQUENCE: 9
atgagagtga aggggataga gaggaattat cagcatttgt gggagaggaa tcagcactcg      60
ttgtggagat ggggcatcat gctccttggg atgttaatga tatgtaaagg agaattgtgg    120
gtcacagttt attatggggt acctgtgtgg aaagaagcaa ccactactct attttgtgca    180
tcagatgcta atcatatga accagaggca cataatatct gggctacaca tgcctgtgtg    240
ccaacagacc ccaacccacg agaaataaaa ctggaaaatg tcacagaaaa ctttaacatg    300
tggaaaaatg acatggtgga gcagatgcat gaggatgtaa tcagtctatg ggatcaaagc    360
ctgaaaccat gtgtaaaatt aaccccactc tgtgtcactt tacattgcac tgaatataag    420
gcccctaatg ccactattaa tgccactgat agggacatag aatgaaaaaa ctgctctttc    480
aatgtaacca cagaagtaat aaataagaag aagcaagaac atgcactttt ttataaactt    540
gatgtggtac aaatggatga atatagtact aataccaact atagattaat aaaattgtaat    600
acctcagtca ttacacaggc gtgtccaaag gtaacctttg agccaattcc catacattat    660
tgtgctccag ctggatttgc gattctaaag tgtaatgata agaagttcaa tgggacgggt    720
ccatgcaaaa acgtcagcac agtgcagtgt acacatggga ttaggccagt agtgtcaacc    780
caactgttgt tgaatggcag tctagcagaa gaagagataa taattagatc tgaaaatctc    840
acaaataatg ctaaaaccat aatagtacag cttaatgagt ctgtaccaat taattgctca    900
aggccctacg aaaataaaag acgacgtaca cctataggac tagggcaagc gtactataca    960
acaaaattaa aggatatat aagaccagca cattgtaata ttagtggagc agaatggaat   1020
aaaactttac aacaggtagc taaaaaatta ggagaccttt tcaaccagac aacaataatt   1080
tttcaaccac actcgggagg ggacccagaa attacaacac acagctttaa ttgtggaggg   1140
gaattttct actgcgatac atcaagactg tttaatagga cttataatac atcaggtagt   1200
acagggtaa ataacagtac aatcaaactc ccatgcagaa taaaacaaat tataaacatg   1260
tggcagggag taggaaaagc aatgtatgcc cctcccattg aaggactaat caatgttca   1320
tcaaacatta caggactatt gttgacaaga gatgggggaa ataatactag cagaatgaa   1380
gccttcaggc ctgagggagg ggatatgaga gacaattgga gaagtgaatt atacaaatat   1440
aaagtagtaa aaattgaacc actaggtcta gcacccactg aggcaaagag aagagtggta   1500
gaaagagaaa aaagagcaat aggactagga gctatgttcc ttgggttctt gggagcagca   1560
ggaagcacga tgggcgcagc gtcaatgacg ctgacggtac aggccagaca gttaatgtct   1620
```

```
ggtatagtgc aacagcaaaa caatttgctg agggctatag aggcgcaaca gcatctgttg   1680
caactcacag tctggggcat taaacagctc caggcaagaa tcctggctgt ggaaagctac   1740
ctaaaggatc aacagctcct aggaatttgg ggttgctctg gaagacacat ttgcaccact   1800
gctgtgccct ggaactctag ctggagtaat aaatctctaa acgagatttg ggtaacatg    1860 acctggatgg agtgggaaaa agaaattgac aattacacag aattaatata cagcttaatt   1920
gaagaatcgc aaacccagca agaaaagaat gaacaagaac tattgaaatt agaccaatgg   1980
gcaagtttgt ggaattggtt tagcataaca aaatggctgt ggtatataaa atattcata    2040 atgatagtag gaggcttgat aggtttaaga atagttttg ctgtgctttc tgtagtaaat    2100
agagttaggc agggatattc acctctgtca tttcagaccc tcctcccagc ccgaggga     2160 cccgacaggc cagaaggaat agaagaagaa ggtggagagc agggcagagg cagatccatt   2220
cgattggtga ccggattctc agcacttatc tgggacgatc taaggaacct gtgcctcttc   2280
agctaccgcc acttgagaga cttaatctta attgcagcga agattgtgga gtttctggga   2340 cgcaggggt gagaagccat caagtacctg tggaacctcc tgcaatattg gattcaggaa    2400
ctaaagaata gtgctattag cttatttgat accacagcaa tagcagtagc tgagggaca   2460 gatagggtca tagagatatt acaaagattt attagagcta ttcttcacat acccagacga   2520
ataagacagg gcttggaaag gctttacta taa                                 2553
```

<210> SEQ ID NO 10
<211> LENGTH: 781
<212> TYPE: PRT
<213> ORGANISM: HIV-1

<400> SEQUENCE: 10

```
Met Arg Val Lys Ile Glu Arg Asn Tyr Gln His Leu Trp Glu Arg Asn
1               5                   10                  15

Gln His Ser Leu Trp Arg Trp Gly Ile Met Leu Leu Gly Met Leu Met
            20                  25                  30

Ile Cys Lys Gly Glu Leu Trp Val Thr Val Tyr Tyr Gly Val Pro Val
        35                  40                  45

Trp Lys Glu Ala Thr Thr Thr Leu Phe Cys Ala Ser Asp Ala Lys Ser
    50                  55                  60

Tyr Glu Pro Glu Ala His Asn Ile Trp Ala Thr His Ala Cys Val Pro
65                  70                  75                  80

Thr Asp Pro Asn Pro Arg Glu Ile Lys Leu Glu Asn Val Thr Glu Asn
                85                  90                  95

Phe Asn Met Trp Lys Asn Asp Met Val Glu Gln Met His Glu Asp Val
            100                 105                 110

Ile Ser Leu Trp Asp Gln Ser Leu Lys Pro Cys Val Lys Leu Thr Pro
        115                 120                 125

Leu Cys Val Thr Leu His Cys Thr Glu Tyr Lys Ala Pro Asn Ala Thr
    130                 135                 140

Ile Asn Ala Thr Asp Arg Asp Ile Gly Met Lys Asn Cys Ser Phe Asn
145                 150                 155                 160

Val Thr Thr Glu Val Ile Asn Lys Lys Gln Glu His Ala Leu Phe
                165                 170                 175

Tyr Lys Leu Asp Val Val Gln Met Asp Asp Asn Ser Thr Asn Thr Asn
            180                 185                 190

Tyr Arg Leu Ile Asn Cys Asn Thr Ser Val Ile Thr Gln Ala Cys Pro
        195                 200                 205
```

-continued

```
Lys Val Thr Phe Glu Pro Ile Pro Ile His Tyr Cys Ala Pro Ala Gly
210                 215                 220
Phe Ala Ile Leu Lys Cys Asn Asp Lys Phe Asn Gly Thr Gly Pro
225                 230                 235                 240
Cys Lys Asn Val Ser Thr Val Gln Cys Thr His Gly Ile Arg Pro Val
                245                 250                 255
Val Ser Thr Gln Leu Leu Leu Asn Gly Ser Leu Ala Glu Glu Glu Ile
                260                 265                 270
Ile Ile Arg Ser Glu Asn Leu Thr Asn Asn Ala Lys Thr Ile Ile Val
        275                 280                 285
Gln Leu Asn Glu Ser Val Pro Ile Asn Cys Ser Arg Pro Tyr Glu Asn
290                 295                 300
Lys Arg Arg Arg Thr Pro Ile Gly Leu Gly Gln Tyr Tyr Thr Thr Lys
305                 310                 315                 320
Leu Lys Gly Tyr Ile Arg Pro Ala His Cys Asn Ile Ser Gly Ala Glu
                325                 330                 335
Trp Asn Lys Thr Leu Gln Gln Val Ala Lys Lys Leu Gly Asp Leu Phe
                340                 345                 350
Asn Gln Thr Thr Ile Ile Phe Gln Pro His Ser Gly Gly Asp Pro Glu
                355                 360                 365
Ile Thr Thr His Ser Phe Asn Cys Gly Gly Glu Phe Phe Tyr Cys Asp
        370                 375                 380
Thr Ser Arg Leu Phe Asn Arg Thr Tyr Ser Thr Ser Gly Ser Thr Gly
385                 390                 395                 400
Val Asn Asn Ser Thr Ile Lys Leu Pro Cys Arg Ile Lys Gln Ile Ile
                405                 410                 415
Asn Met Trp Gln Gly Val Gly Lys Ala Met Tyr Ala Pro Pro Ile Glu
                420                 425                 430
Gly Leu Ile Lys Cys Ser Ser Asn Ile Thr Gly Leu Leu Leu Thr Arg
        435                 440                 445
Asp Gly Gly Asn Asn Thr Arg Gln Asn Glu Ala Phe Arg Pro Gly Gly
450                 455                 460
Gly Asp Met Arg Asp Asn Trp Arg Ser Glu Leu Tyr Lys Tyr Lys Val
465                 470                 475                 480
Val Arg Ile Glu Pro Leu Gly Leu Ala Pro Thr Glu Ala Lys Arg Arg
                485                 490                 495
Val Val Glu Arg Glu Lys Arg Ala Ile Gly Leu Gly Ala Met Phe Leu
                500                 505                 510
Gly Phe Leu Gly Ala Ala Gly Ser Thr Met Gly Ala Ala Ser Met Thr
        515                 520                 525
Leu Thr Val Gln Ala Arg Gln Leu Met Ser Gly Ile Val Gln Gln Gln
530                 535                 540
Asn Asn Leu Leu Arg Ala Ile Glu Ala Gln Gln His Leu Leu Gln Thr
545                 550                 555                 560
Leu Val Trp Gly Ile Lys Gln Leu Gln Ala Arg Ile Leu Ala Val Glu
                565                 570                 575
Ser Tyr Leu Lys Asp Gln Gln Leu Leu Gly Ile Trp Gly Cys Ser Gly
                580                 585                 590
Arg His Ile Cys Thr Thr Ala Val Pro Trp Asn Ser Ser Trp Ser Asn
        595                 600                 605
Lys Ser Leu Asn Glu Ile Trp Gly Asn Met Thr Trp Met Glu Trp Glu
610                 615                 620
```

-continued

```
Lys Glu Ile Asp Asn Tyr Thr Glu Leu Ile Tyr Ser Leu Ile Glu Glu
625                 630                 635                 640

Ser Gln Thr Gln Gln Glu Lys Asn Glu Gln Glu Leu Leu Lys Leu Asp
            645                 650                 655

Gln Trp Ala Ser Leu Trp Asn Trp Phe Ser Ile Thr Lys Trp Leu Trp
        660                 665                 670

Tyr Ile Lys Ile Phe Ile Met Ile Val Gly Gly Leu Ile Gly Leu Arg
    675                 680                 685

Ile Val Phe Ala Val Leu Ser Val Val Asn Arg Val Arg Gln Gly Tyr
690                 695                 700

Ser Pro Leu Ser Phe Gln Thr Leu Leu Pro Ala Pro Arg Gly Pro Asp
705                 710                 715                 720

Arg Pro Glu Gly Ile Glu Glu Gly Gly Glu Gln Gly Arg Gly Arg
            725                 730                 735

Ser Ile Arg Leu Val Thr Gly Phe Ser Ala Leu Ile Trp Asp Asp Leu
        740                 745                 750

Arg Asn Leu Cys Leu Phe Ser Tyr Arg His Leu Arg Asp Leu Ile Leu
    755                 760                 765

Ile Ala Ala Lys Ile Val Glu Phe Leu Gly Arg Arg Gly
770                 775                 780

<210> SEQ ID NO 11
<211> LENGTH: 2586
<212> TYPE: DNA
<213> ORGANISM: HIV-1

<400> SEQUENCE: 11
atgagagtga aggggataca gaggaactgt caaaacttgt ggagatgggg aactataatc      60
ttgggtatga tgataatttg tagtgctgca gaaaaattgt gggttactgt ttactatggg     120
gtacctgtgt ggaaagatgc agaaaccacc ttattttgtg catcagatgc gaaagcatat     180
gatacagaag tgcataatgt ctgggccaca catgcctgtg tacctacaga ccccaaccca     240
caagaaataa atttggaaaa tgtgacagaa aattttaaca tgtggaaaaa taacatggta     300
gagcagatgc atacagatat aatcagtcta tgggaccaaa gcctaaagcc atgtgtacag     360 ttaaccccte tetgtgttac tttagattgt actgatgcca caaatgccac taataccact     420
atcattagtg acatgaaagg agaaataaaa aactgctctt tcaatatgac cacagaatta     480
aaggataaga cacagaaagt acgttcattt ttctataaga tggatatagt acaaattaac     540
aacaacaaca gcaacagcaa cagtagtcag atagattaa taagttgtaa tacctcaacc     600
attacacaag cttgtccaaa ggtatccttt gagccaattc ccatacatta ttgtgctcca     660
gctggttttg cgattctaaa atgcaaggat aaggagttca tggaacagg gccatgcagg     720 aatgtcagca cagtacaatg cacacatgga atcaagccag tagtatcaac tcaactactg     780
ttaaatggca gtctagcaga agaaaaggta atgattagat ctgaaaatat cacagacaat     840
actaaaaaca taatagtgca acttactgag cctgtaaaaa ttaattgtac cagacctaac     900
aacaatacaa gaaagagtat aagtataggg ccaggacgag cattcattgc aagagataga     960
ataatagggg atataagaca agcacattgt aacatcagta gagcagcatg gaataacact    1020
ttgcagaagg tagcccaaca attaagaaca cactttgaga cagaacaat aatctttaat    1080 cactccgcag gaggggaccc agaaataact acacatagtt ttaattgtgg aggagaattt    1140
ttctattgta gcacaacagg cctgtttaat agtacttgga atagcaatgc agcacgcag    1200 gggtcaaata gcacgggttc aaacgacact ataactctcc aatgcagaat aaggcagatt    1260
```

-continued

```
ataaggatgt ggcagagagt aggacaagca atgtatgccc ctcccatccc agggtaata      1320 agatgtgact caaacattac aggactaata ttaacaagag atggggggga taataacagc     1380
acaaatgaga ccttcagacc tggaggagga gatatgaggg acaattggag aagtgaatta     1440
tataagtata aagtagtaaa gattgaacca ctaggagtag cacccaccag ggcaaagaga     1500
agagtggtgg aaagagaaaa aagagcaata gcaggaatag gagctgtgtt ccttgggttc     1560
ttgggagcag caggaagcac aatgggcgca gcgtcactga cgctgacggt acagaccaga     1620
cagctattgt ctggcatagt gcaacagcaa agcaatttgc tgagggctat agaggctcaa     1680
cagcatctgt tgaaactcac ggtctgggc attaaacagc tccaggcacg agtcctggct      1740
gtggagagat acctaaagga tcaacagctc ctaggaattt ggggttgctc tggaaaactc     1800
atttgcacca ctactgtgcc ctggaactct agttggagta ataaatccta tagtgagata     1860
tgggacaaca tgacctggct gcaatgggat aaagaaatta gcaattatac acaaataata     1920
tatgatctaa ttgaagaatc acagaaccag caggaaaaga atgaacaaga cctattggca     1980
ttggacaagt gggcaaatct atggaattgg tttgacatat caaaatggct gtggtatata     2040
agaatattta atgatagtag gaggcttaa ataggattaa aatagttttt tgctgtaatt      2100
tcagtaataa atagagttag gcagggatac tcacctttgt cgttccagac ccttgccccg     2160
aacccagggg gtctcgacag gcccggaaga atcgaagaag aagtggagag caagacaga     2220 agcagatcga ttcgcttagt cagcgggttc ttagcacttg cctggaggga cctgcggagc     2280
ctgtgcctct tcagctacca ccgcttgaga gacttcatct tgattgccgc gaggactgtg     2340
gaacttctgg gacacagcag tctcaagggg ttgagactgg ggtgggaagg actcaagtat     2400
ctggggaatc tcctgttgta ttgggggtcag gaactaaaaa ttagtgctat tagtttgttt     2460
gataccatag caatagtaat agctggctgg acagataggg tcatagaaat aggacaaaga     2520
attggtagag ctattctcaa catacctaga agaatcaggc agggcgccga agggctttta     2580
caataa                                                                2586
```

<210> SEQ ID NO 12
<211> LENGTH: 861
<212> TYPE: PRT
<213> ORGANISM: HIV-1

<400> SEQUENCE: 12

```
Met Arg Val Lys Ile Gln Arg Asn Cys Gln Asn Leu Trp Arg Trp Gly
1               5                   10                  15

Thr Ile Ile Leu Gly Met Met Ile Ile Cys Ser Ala Ala Glu Lys Leu
            20                  25                  30

Trp Val Thr Val Tyr Tyr Gly Val Pro Val Trp Lys Asp Ala Glu Thr
        35                  40                  45

Thr Leu Phe Cys Ala Ser Asp Ala Lys Ala Tyr Asp Thr Glu Val His
    50                  55                  60

Asn Val Trp Ala Thr His Ala Cys Val Pro Thr Asp Pro Asn Pro Gln
65                  70                  75                  80

Glu Ile Asn Leu Glu Asn Val Thr Glu Asn Phe Asn Met Trp Lys Asn
                85                  90                  95

Asn Met Val Glu Gln Met His Thr Asp Ile Ile Ser Leu Trp Asp Gln
            100                 105                 110

Ser Leu Lys Pro Cys Val Gln Leu Thr Pro Leu Cys Val Thr Leu Asp
        115                 120                 125
```

-continued

```
Cys Thr Asp Ala Thr Asn Ala Thr Asn Thr Thr Ile Ile Ser Asp Met
    130                 135                 140
Lys Gly Glu Ile Lys Asn Cys Ser Phe Asn Met Thr Thr Glu Leu Lys
145                 150                 155                 160
Asp Lys Thr Gln Lys Val Arg Ser Phe Tyr Lys Met Asp Ile Val
                165                 170                 175
Gln Ile Asn Asn Asp Asn Asn Ser Asn Ser Asn Ser Ser Gln Tyr Arg
                180                 185                 190
Leu Ile Ser Cys Asn Thr Ser Val Ile Thr Gln Ala Cys Pro Lys Val
            195                 200                 205
Ser Phe Glu Pro Ile Pro Ile His Tyr Cys Ala Pro Ala Gly Phe Ala
    210                 215                 220
Ile Leu Lys Cys Lys Asp Lys Glu Phe Asn Gly Thr Pro Cys Arg
225                 230                 235                 240
Asn Val Ser Thr Val Gln Cys Thr His Gly Ile Lys Pro Val Val Ser
                245                 250                 255
Thr Gln Leu Leu Leu Asn Gly Ser Leu Ala Glu Glu Lys Val Met Ile
                260                 265                 270
Arg Ser Glu Asn Ile Thr Asp Asn Thr Lys Asn Ile Ile Val Gln Leu
            275                 280                 285
Thr Glu Pro Val Lys Ile Asn Cys Thr Arg Pro Asn Asn Asn Thr Arg
    290                 295                 300
Arg Gly Ile Ser Ile Gly Pro Gly Arg Ala Phe Ile Ala Arg Asp Arg
305                 310                 315                 320
Ile Ile Gly Asp Ile Arg Gln Ala His Cys Asn Ile Ser Arg Ala Ala
                325                 330                 335
Trp Asn Asn Thr Leu Gln Lys Val Ala Gln Gln Leu Arg Thr His Phe
            340                 345                 350
Glu Asn Arg Thr Ile Ile Phe Asn His Ser Ala Gly Gly Asp Pro Glu
    355                 360                 365
Ile Thr Thr His Ser Phe Asn Cys Gly Gly Glu Phe Phe Tyr Cys Ser
    370                 375                 380
Thr Thr Gly Leu Phe Asn Ser Thr Trp Ala Ser Asn Ala Ser Thr Gln
385                 390                 395                 400
Gly Ser Asn Ser Thr Gly Ser Asn Asp Thr Ile Thr Leu Gln Cys Arg
                405                 410                 415
Ile Arg Gln Ile Ile Arg Met Trp Gln Arg Val Gly Gln Ala Met Tyr
            420                 425                 430
Ala Pro Pro Ile Pro Gly Val Ile Arg Cys Asp Ser Asn Ile Thr Gly
    435                 440                 445
Leu Ile Leu Thr Arg Asp Gly Gly Asp Asn Asn Ser Thr Asn Glu Thr
450                 455                 460
Phe Arg Pro Gly Gly Gly Asp Met Arg Asp Asn Trp Arg Ser Glu Leu
465                 470                 475                 480
Tyr Lys Tyr Lys Val Val Lys Ile Glu Pro Leu Gly Val Ala Pro Thr
                485                 490                 495
Arg Ala Lys Arg Arg Val Val Glu Arg Glu Lys Arg Ala Ile Ala Gly
            500                 505                 510
Ile Gly Ala Val Phe Leu Gly Phe Leu Gly Ala Ala Gly Ser Thr Met
            515                 520                 525
Gly Ala Ala Ser Leu Thr Leu Thr Val Gln Thr Arg Gln Leu Leu Ser
    530                 535                 540
Gly Ile Val Gln Gln Gln Ser Asn Leu Leu Arg Ala Ile Glu Ala Gln
```

-continued

```
            545                 550                 555                 560
Gln His Leu Leu Lys Thr Leu Val Trp Gly Ile Lys Gln Leu Gln Ala
                565                 570                 575
Arg Val Leu Ala Val Glu Arg Tyr Leu Lys Asp Gln Gln Leu Leu Gly
                580                 585                 590
Ile Trp Gly Cys Ser Gly Lys Leu Ile Cys Thr Thr Val Pro Trp
                595                 600                 605
Asn Ser Ser Trp Ser Asn Lys Ser Tyr Ser Glu Ile Trp Asp Asn Met
        610                 615                 620
Thr Trp Leu Gln Glu Trp Lys Glu Ile Ser Asn Tyr Thr Gln Ile Ile
625                 630                 635                 640
Tyr Asp Leu Ile Glu Glu Ser Gln Asn Gln Gln Glu Lys Asn Glu Gln
                645                 650                 655
Asp Leu Leu Ala Leu Asp Lys Trp Ala Asn Leu Trp Asn Trp Phe Asp
                660                 665                 670
Ile Ser Lys Trp Leu Trp Tyr Ile Arg Ile Phe Ile Met Ile Val Gly
                675                 680                 685
Gly Leu Ile Gly Leu Arg Ile Val Phe Ala Val Ile Ser Val Ile Asn
        690                 695                 700
Arg Val Arg Gln Gly Tyr Ser Pro Leu Ser Phe Gln Thr Leu Ala Pro
705                 710                 715                 720
Asn Pro Gly Gly Leu Asp Arg Pro Gly Arg Ile Glu Glu Gly Gly
                725                 730                 735
Glu Gln Asp Arg Ser Arg Ser Ile Arg Leu Val Ser Gly Phe Leu Ala
                740                 745                 750
Leu Ala Trp Glu Asp Leu Arg Ser Leu Cys Leu Phe Ser Tyr His Arg
                755                 760                 765
Leu Arg Asp Phe Ile Leu Ile Ala Ala Arg Thr Val Glu Leu Leu Gly
        770                 775                 780
His Ser Ser Leu Lys Gly Leu Arg Leu Gly Trp Glu Gly Leu Lys Tyr
785                 790                 795                 800
Leu Gly Asn Leu Leu Tyr Trp Gly Gln Glu Leu Lys Ile Ser Ala
                805                 810                 815
Ile Ser Leu Phe Asp Thr Ile Ala Ile Val Ile Ala Gly Trp Thr Asp
                820                 825                 830
Arg Val Ile Glu Ile Gly Gln Arg Ile Gly Arg Ala Ile Leu Asn Ile
                835                 840                 845
Pro Arg Arg Ile Arg Gln Gly Ala Glu Arg Ala Leu Gln
        850                 855                 860
```

<210> SEQ ID NO 13
<211> LENGTH: 2607
<212> TYPE: DNA
<213> ORGANISM: HIV-1

<400> SEQUENCE: 13

```
atgagagtga agggatcag gaagaattat cagcacttgt ggagatggag taccatgctg      60
ctccttggga tgttaatgat ttgtagtgct acagaacaat gtgggtcac agtctattat     120
ggggtacctg tgtggaaaga agcaaacacc actctatttt gtgcatcaga tgctaaagca     180
tatgatacag aggcacataa tgtttgggcc acacatgcct gtgtacccac agaccccaac     240
ccacaagaaa tagtattggc aaatgtgaca gaagatttta acatgtgaa aaataacatg     300
gtagaacaga tgcatgagga tataatcagt ttatgggatc aaagcctaaa gccatgtgta     360
```

-continued

```
aaattaaccc cactctgtgt tactttaaat tgcactgatg taaggaatgg tactattgtg    420
aggaatagta ctattagggt cgaggaaggg atgaaggaag aaataaaaaa ctgctctttc    480
aatgtcacca caagcatgag agacaagttg cagaaagaag atgcattttt ttataaatct    540
gatgtaatac caataggtaa tgataataat actaatacca gcaataataa tatcacctat    600
accagctata ggttgagaag ttgtaatacc tcagtcatta cacaggcctg tccaaagata    660
aactttgagc caattcccat acattattgt gccccggctg ggtttgcgat tctgaagtgt    720
aataatagga cgttcgaggg aaaaggacca tgtaaaaatg tcagcacagt acaatgtaca    780
catggaatta ggccagtagt atcaactcaa ctgctgttaa atggcagtct agcagaaaaa    840
gatatagtaa ttagatctgc caatttctca gacaatgcta agccataat agtacagctg    900
aacgaaactg tacaaatcaa ttgtacaaga cccaacaaca atacaagaag aagataact    960
atgggaccag aagagtata ttatacaaca ggagacataa taggagacat aagacgagca   1020
cattgtaaca ttagtaagga agattggaat aacactctaa acagatagc taaaaaatta   1080
agagaacaat ttggggataa taaaacaata gcctttaagc catcctcagg aggggaccca   1140
gaaattgtaa tgcacagttt taattgtgga ggggaatttt tctactgtaa tacaacaaaa   1200
ctgtttaata gtacttggga tggtaatagt actcggaata atactgaagg gtcaagtaac   1260
aatgaaata tcacacttca atgcagaata aaacaaatta taaacatgtg gcagggagta   1320
ggaaaagcaa tgtatgcccc tcccatcaga ggacaaatta gatgttcatc aaacattaca   1380
gggctgctat taacaagaga tggtggtaat accaacgata ctaacaatac tgagatcttc   1440
agacctggag gaggagatat gagggacaat tggagaagtg aattatataa atataaagta   1500
gtaaaaattg aaccattagg aatagcaccc accaaggcaa agagaagagt ggtgcaaaga   1560
gaaaaaagag caatgggaat aggagctctg ttccttgggt tcttgggagc agcaggaagc   1620
actatgggcg cagcgtcaat gacgctgacg gtacaggcca gacaactatt gtctggtata   1680
gtgcaacagc agaacaattt gctgagggct attgaggcgc aacaccatct gttgcaactc   1740
acagtctggg gcatcaagca gctccaggca agagtcctgg ctgtggaaag atacctaaag   1800
gatcaacagc tcctggggat ttggggttgc tctggaaaac tcatttgcac cactgctgtg   1860
ccttggaatg ctagttggag taataaatct ctggataaga tttggaataa catgacctgg   1920
atgcagtggg aaagagaaat tgacaattac acaagtctaa tatacacttt aattgaagaa   1980
tcgcagaacc aacaagaaaa gaatgaacta gagttactag aattagataa atgggcaaat   2040
ttgtggaatt ggtttgacat aacaaaatgg ctgtggtata taaaaatatt cataatgata   2100
gtaggaggct tgataggttt aagaatagtt tttgttatac tttctatagt gaatagagtt   2160
aggcagggat actcaccatt atcgtttcag acccgcctcc cagcccagag ggacccgac   2220
aggcccgaag gaatcgaaga agaaggtgga gggagaggca gagacacatc cgggccatta   2280
gtggatggat tcttagcaat tatctgggtc gacctgcgga gcctgttcct cttcagctac   2340
caccgcttga gagacttact cttgattgta gcgaggattg tggaacttct gggacgcagg   2400
gggtgggaaa tcctcaagta ttggtggaat ctcctacagt attggattca ggaactaaag   2460
aatagtgctg ttagcttgct caacgccaca gccatagcag tagctgaggg gacagatagg   2520
attatagaag tagcaagaag gacttttaga gctattctcc acatacctag aagaataaga   2580
cagggcttgg aaagggcttt gctataa                                       2607
```

<210> SEQ ID NO 14
<211> LENGTH: 866

```
<212> TYPE: PRT
<213> ORGANISM: HIV-1

<400> SEQUENCE: 14

Met Arg Val Lys Ile Lys Asn Tyr Gln His Leu Trp Arg Trp Ser Thr
1               5                   10                  15

Met Leu Leu Leu Gly Met Leu Met Ile Cys Ser Ala Thr Glu Gln Leu
            20                  25                  30

Trp Val Thr Val Tyr Tyr Gly Val Pro Val Trp Lys Glu Ala Asn Thr
        35                  40                  45

Thr Leu Phe Cys Ala Ser Asp Ala Lys Ala Tyr Asp Thr Glu Ala His
    50                  55                  60

Asn Val Trp Ala Thr His Ala Cys Val Pro Thr Asp Pro Asn Pro Gln
65                  70                  75                  80

Glu Ile Val Leu Ala Asn Val Thr Glu Asp Phe Asn Met Trp Lys Asn
                85                  90                  95

Asn Met Val Glu Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asp Val Arg Asn Gly Thr Ile Val Arg Asn Ser Thr Ile Arg
    130                 135                 140

Val Glu Glu Gly Met Lys Glu Ile Lys Asn Cys Ser Phe Asn Val
145                 150                 155                 160

Thr Thr Ser Met Gly Asp Lys Leu Gln Lys Glu Asp Ala Phe Phe Tyr
                165                 170                 175

Lys Ser Asp Val Val Gln Met Gly Asp Asn Asn Asn Thr Asn Thr Ser
            180                 185                 190

Asn Asn Asn Ile Thr Tyr Thr Ser Tyr Arg Leu Arg Ser Cys Asn Thr
        195                 200                 205

Ser Val Ile Thr Gln Ala Cys Pro Lys Ile Asn Phe Glu Pro Ile Pro
    210                 215                 220

Ile His Tyr Cys Ala Pro Ala Gly Phe Ala Ile Leu Lys Cys Asn Asn
225                 230                 235                 240

Arg Thr Phe Glu Gly Lys Gly Pro Cys Lys Asn Val Ser Thr Val Gln
                245                 250                 255

Cys Thr His Gly Ile Arg Pro Val Val Ser Thr Gln Leu Leu Leu Asn
            260                 265                 270

Gly Ser Leu Ala Glu Lys Asp Ile Val Ile Arg Ser Ala Asn Phe Ser
        275                 280                 285

Asp Asn Ala Lys Ala Ile Ile Val Gln Leu Asn Glu Thr Val Gln Ile
    290                 295                 300

Asn Cys Thr Arg Pro Asn Asn Asn Thr Arg Arg Ile Thr Met Gly
305                 310                 315                 320

Pro Gly Ala Val Tyr Tyr Thr Thr Gly Asp Ile Ile Gly Asp Ile Arg
                325                 330                 335

Arg Ala His Cys Asn Ile Ser Lys Glu Asp Trp Thr Asn Thr Leu Lys
            340                 345                 350

Gln Ile Ala Lys Lys Leu Arg Glu Gln Phe Gly Asp Asn Lys Thr Ile
        355                 360                 365

Ala Phe Lys Pro Ser Ser Gly Gly Asp Pro Glu Ile Val Met His Ser
    370                 375                 380

Phe Asn Cys Gly Gly Glu Phe Phe Tyr Cys Asn Thr Thr Lys Leu Phe
385                 390                 395                 400
```

-continued

```
Asn Ser Thr Trp Phe Gly Asn Ser Thr Arg Asn Asn Thr Glu Gly Ser
            405                 410                 415
Ser Asn Asn Gly Asn Ile Thr Leu Gln Cys Arg Ile Lys Gln Ile Ile
        420                 425                 430
Asn Met Trp Gln Gly Val Gly Lys Ala Met Tyr Ala Pro Pro Ile Arg
        435                 440                 445
Gly Gln Ile Arg Cys Ser Ser Asn Ile Thr Gly Leu Leu Leu Thr Arg
        450                 455                 460
Asp Gly Gly Asn Thr Asn Asp Thr Asn Asn Thr Glu Ile Phe Arg Pro
465                 470                 475                 480
Gly Gly Gly Asp Met Arg Asp Asn Trp Arg Ser Glu Leu Tyr Lys Tyr
                485                 490                 495
Lys Val Val Lys Ile Glu Pro Leu Gly Ile Ala Pro Thr Lys Ala Lys
                500                 505                 510
Arg Arg Val Val Gln Arg Glu Lys Arg Ala Met Gly Ile Gly Ala Leu
            515                 520                 525
Phe Leu Gly Phe Leu Gly Ala Ala Gly Ser Thr Met Gly Ala Ala Ser
        530                 535                 540
Met Thr Leu Thr Val Gln Ala Arg Gln Leu Leu Ser Gly Ile Val Gln
545                 550                 555                 560
Gln Gln Asn Asn Leu Leu Arg Ala Ile Glu Ala Gln His His Leu Leu
                565                 570                 575
Gln Thr Leu Val Trp Gly Ile Lys Gln Leu Gln Ala Arg Val Leu Ala
            580                 585                 590
Val Glu Arg Tyr Leu Lys Asp Gln Gln Leu Leu Gly Ile Trp Gly Cys
        595                 600                 605
Ser Gly Lys Leu Ile Cys Thr Thr Ala Val Pro Trp Asn Ala Ser Trp
        610                 615                 620
Ser Asn Lys Ser Leu Asp Lys Ile Trp Asn Asn Met Thr Trp Met Gln
625                 630                 635                 640
Trp Glu Arg Glu Ile Asp Asn Tyr Thr Ser Leu Ile Tyr Thr Leu Ile
                645                 650                 655
Glu Glu Ser Gln Asn Gln Gln Glu Lys Asn Glu Leu Glu Leu Leu Glu
                660                 665                 670
Leu Asp Lys Trp Ala Asn Leu Trp Asn Trp Phe Asp Ile Thr Lys Trp
            675                 680                 685
Leu Trp Tyr Ile Lys Ile Phe Ile Met Ile Val Gly Gly Leu Ile Gly
        690                 695                 700
Leu Arg Ile Val Phe Val Ile Leu Ser Ile Val Asn Arg Val Arg Gln
705                 710                 715                 720
Gly Tyr Ser Pro Leu Ser Phe Gln Thr Arg Leu Pro Ala Gln Arg Gly
                725                 730                 735
Pro Asp Arg Pro Glu Gly Ile Glu Glu Glu Gly Gly Arg Gly Arg
                740                 745                 750
Asp Thr Ser Gly Pro Leu Val Asp Gly Phe Leu Ala Ile Ile Trp Val
            755                 760                 765
Asp Leu Arg Ser Leu Phe Leu Phe Ser Tyr His Arg Leu Arg Asp Leu
        770                 775                 780
Leu Leu Ile Ala Thr Arg Ile Val Glu Leu Leu Gly Arg Arg Gly Trp
785                 790                 795                 800
Glu Ile Leu Lys Tyr Trp Trp Asn Leu Leu Gln Tyr Trp Ile Gln Glu
                805                 810                 815
```

-continued

```
Leu Lys Asn Ser Ala Val Ser Leu Leu Asn Ala Thr Ala Ile Ala Val
            820                 825                 830

Ala Glu Gly Thr Asp Arg Ile Ile Glu Val Ala Arg Arg Thr Phe Arg
        835                 840                 845

Ala Ile Leu His Ile Pro Arg Arg Ile Arg Gln Gly Leu Glu Arg Ala
    850                 855                 860

Leu Leu
865
```

<210> SEQ ID NO 15
<211> LENGTH: 2586
<212> TYPE: DNA
<213> ORGANISM: HIV-1

<400> SEQUENCE: 15

| | | | | | |
|---|---|---|---|---|---|
| atgagagtga | agggatcat | gaagaattat | cagcactttt | ggagatgggg | caccatgctc | 60 |
| ctggggttat | tgatgatctg | tagtgctgca | gatcaattgt | gggtcacagt | ctattatgga | 120 |
| gtacctgtgt | ggaaggaaac | aaccaccact | ctattttgtg | catcagatgc | taaagcatat | 180 |
| gataaagagg | tacataatgt | ttgggccaca | catgcctgtg | tacccacaga | ccccaaccca | 240 |
| caagaaatac | cattggtaaa | tgtaacagaa | aattttaaca | tgtggaaaaa | taacatggta | 300 |
| gatcaaatgc | atgaggatat | aatcagttta | tgggatcaaa | gcctaaagcc | atgtgtaaaa | 360 |
| ttaaccccac | tctgtgttac | tttaaattgc | actgatgatt | tgaggaatgc | tactaatacc | 420 |
| actactaata | ccaatagtaa | ttgggagaaa | ccaatggaga | aaggagaaat | aaaaaactgc | 480 |
| tctttcaaaa | tcacctcaag | cataagagat | aaggtacaga | acaatatgc | actttttat | 540 |
| agccttgatg | tagtaccaat | aaagaataac | aataatatta | gcaataagat | tagatatagg | 600 |
| ttaagaagtt | gtaacacctc | agtcattaca | caggcctgtc | caaggtaac | ctttgagcca | 660 |
| attcccatac | attattgtgc | cccggctggt | tttgcgattc | taaatgtaa | tgataagaag | 720 |
| ttcaatggaa | caggaccatg | tacaaatgtc | agcacagtac | aatgtactca | tggaattagg | 780 |
| ccagtagtat | caactcaact | actgttaaat | ggcagtctag | cagaagaaga | ggtagtaatt | 840 |
| agatctgaaa | atttcacaga | caatgctaaa | accataatag | tacaactgaa | agaccctgta | 900 |
| gaaatcaatt | gtacaagacc | caacagaaat | gcatggaaag | catacctat | ggagtacca | 960 |
| gggagaaaat | tctatgcaag | aagaaacata | acaggagata | taagacaagc | atattgtaac | 1020 |
| cttagtatag | caaagtggaa | taacacttta | aaacagatag | ttgaaaaatt | aagattacat | 1080 |
| tttaaaaata | aaacaatagt | ctttaatagt | tcctcagggg | gggacccaga | aattatactg | 1140 |
| cacagtttta | attgtggagg | ggaatttttc | tattgtaatt | caacaaaact | gtttaatagt | 1200 |
| acttggaata | gtactactga | agggttaaat | aacactggaa | agacccaat | cgtactccca | 1260 |
| tgcagaataa | agcaaattat | aaacatgtgg | caggaagtag | gaaaagcaat | gtatgcccct | 1320 |
| cccatcgcag | acctaattag | atgctcatca | aatattacag | ggctgctatt | aacaagagat | 1380 |
| ggtggtgttg | atgagaacag | caacaccacc | gagaccttca | ggcctggagg | aggaaatatg | 1440 |
| agggacaatt | ggagaagtga | attatataaa | tataaagcag | taaaattga | acccttaggg | 1500 |
| gtagcaccca | ccaaggcaaa | gagaagagtg | gtgcagagag | aaaaaagagc | agtgggaata | 1560 |
| ggagctgtgt | tccttgggtt | cttgggagca | gcaggaagca | ctatgggcgc | agcatcaata | 1620 |
| acgctgacgg | tacaggccag | acaattattg | tctggtatag | tgcaacagca | gaacaatttg | 1680 |
| ctgagggcta | ttgaggcgca | acagcatctg | ttgcaactca | cagtctgggg | catcaagcag | 1740 |
| ctccaggcga | gagtcctggc | tgtggaaaga | tacctaaagg | atcaacagct | cctgggattt | 1800 |

-continued

```
tggggttgct ctggaaaact catctgcacc actgctgtgc cttggaatgc tagttggagt    1860
aataaatctc tggataggat ttggaataat atgacctgga tggagtggga aagagaaatt    1920
gacaattaca caggcttaat atacaactta attgaagaat cgcaaaacca acaagaaaag    1980
aatgaacaag aattattagc attagataaa tgggcaagtt tgtggaattg gtttgacata    2040
acaaactggc tgtggtatat aaaaatattc ataatgatag taggaggctt gataggttta    2100
agaatagttt ttactgtact ttctatagtg aatagagtta ggcagggata ctcaccatta    2160
tcgtttcaga cccaccaccc agctcagagg gaacccgaca ggcccgaagg aatcgaagga    2220
gaaggtggag agagagacag agacagatcc ggtcccttag tggatggatt cttagcaatt    2280
atctgggtcg acctgcggag cctgtgcatc ttcctctacc accgcttgag agacttactc    2340
ttgattgtaa cgaggattgt ggaacttctg ggacgcaggg ggtgggaagt cctcaaatat    2400
tggtggaatc tcctacagta ttggagtcag gaactaaaga atagtgctat taacttgctc    2460
aacgccacag ccatagcagt agctgagggg acagataggg ttatagaaat attacaaaga    2520
gcttttagag ctattctcca catacctaca agaataagac agggcttgga aagggctttg    2580
ctataa                                                                2586
```

<210> SEQ ID NO 16
<211> LENGTH: 855
<212> TYPE: PRT
<213> ORGANISM: HIV-1

<400> SEQUENCE: 16

```
Met Arg Val Lys Ile Met Lys Asn Tyr Gln His Phe Trp Arg Trp Gly
 1               5                  10                  15

Thr Met Leu Leu Gly Leu Leu Met Ile Cys Ser Ala Ala Asp Gln Leu
            20                  25                  30

Trp Val Thr Val Tyr Tyr Gly Val Pro Val Trp Lys Glu Thr Thr Thr
        35                  40                  45

Thr Leu Phe Cys Ala Ser Asp Ala Lys Ala Tyr Asp Lys Glu Val His
    50                  55                  60

Asn Val Trp Ala Thr Met Ala Cys Val Pro Thr Phe Pro Asn Pro Gln
65                  70                  75                  80

Ile Val Glu Asn Phe Asn Met Leu Lys Asn Asn Met Val Glu Gln Asp
                85                  90                  95

His Glu Asp Ile Ile Ser Leu Trp Asp Gln Ser Leu Lys Pro Cys Thr
            100                 105                 110

Lys Leu Thr Pro Leu Cys Val Thr Leu Asn Cys Thr Asp Asp Leu Arg
        115                 120                 125

Asn Ala Asn Asn Thr Thr Thr Asn Thr Asn Ser Asn Trp Glu Lys Pro
    130                 135                 140

Met Glu Lys Gly Glu Ile Lys Asn Cys Ser Phe Lys Ile Thr Ser Ser
145                 150                 155                 160

Ile Arg Asp Lys Val Gln Lys Gln Tyr Ala Leu Phe Tyr Ser Leu Asp
                165                 170                 175

Val Val Pro Ile Lys Asn Asn Asn Ile Ser Asn Lys Ile Arg Tyr
            180                 185                 190

Arg Leu Arg Ser Cys Asn Thr Ser Val Ile Thr Gln Ala Cys Pro Lys
        195                 200                 205

Val Thr Phe Glu Pro Ile Pro Ile His Tyr Cys Ala Pro Ala Gly Phe
    210                 215                 220
```

-continued

```
Ala Ile Leu Lys Cys Asn Asp Lys Lys Phe Asn Gly Thr Gly Pro Cys
225                 230                 235                 240
Thr Asn Val Ser Thr Val Gln Cys Thr His Gly Ile Arg Asn Val Val
            245                 250                 255
Ser Thr Gln Leu Leu Asn Gly Ser Leu Ala Glu Glu Val Val
        260                 265                 270
Ile Arg Ser Glu Asn Phe Thr Asp Asn Ala Lys Thr Ile Ile Val Gln
    275                 280                 285
Leu Lys Asp Pro Val Glu Ile Asn Cys Thr Arg Pro Asn Arg Asn Ala
290                 295                 300
Trp Lys Gly Ile Pro Ile Gly Val Pro Gly Arg Lys Phe Tyr Ala Arg
305                 310                 315                 320
Arg Asn Ile Thr Gly Asp Ile Arg Gln Ala Tyr Cys Asn Leu Ser Ile
                325                 330                 335
Ala Lys Trp Thr Asn Thr Leu Lys Gln Ile Val Glu Lys Leu Arg Leu
            340                 345                 350
His Phe Lys Asn Lys Thr Ile Val Phe Lys Ser Ser Gly Gly Asp
        355                 360                 365
Pro Glu Ile Ile Leu His Ser Phe Asn Cys Gly Gly Glu Phe Phe Tyr
    370                 375                 380
Cys Asn Ser Thr Lys Leu Phe Asn Ser Thr Trp Phe Ser Thr Thr Glu
385                 390                 395                 400
Gly Leu Asn Asn Thr Gly Asn Glu Asp Pro Ile Val Leu Pro Cys Arg
                405                 410                 415
Ile Lys Gln Ile Ile Asn Met Trp Gln Glu Val Gly Lys Ala Met Tyr
            420                 425                 430
Ala Pro Pro Ile Ala Asp Leu Ile Arg Cys Ser Ser Asn Ile Thr Gly
        435                 440                 445
Leu Leu Leu Thr Arg Asp Gly Val Asp Glu Asn Ser Asn Thr Thr
    450                 455                 460
Glu Thr Phe Arg Pro Gly Gly Gly Asn Met Arg Asp Asn Trp Arg Ser
465                 470                 475                 480
Glu Leu Tyr Lys Tyr Lys Ala Val Lys Ile Glu Pro Leu Gly Val Ala
                485                 490                 495
Pro Thr Lys Ala Lys Arg Arg Val Val Gln Arg Glu Lys Arg Ala Val
            500                 505                 510
Gly Ile Gly Ala Val Phe Leu Gly Phe Leu Gly Ala Ala Gly Ser Thr
        515                 520                 525
Met Gly Ala Ala Ser Ile Thr Leu Thr Val Gln Ala Arg Gln Leu Leu
    530                 535                 540
Ser Gly Ile Val Gln Gln Asn Asn Leu Leu Arg Ala Ile Glu Ala
545                 550                 555                 560
Gln Gln His Leu Leu Gln Thr Leu Val Trp Gly Ile Lys Gln Leu Gln
                565                 570                 575
Ala Arg Val Leu Ala Val Glu Arg Tyr Leu Lys Asp Gln Gln Leu Leu
            580                 585                 590
Gly Phe Trp Gly Cys Ser Gly Lys Leu Ile Cys Thr Thr Ala Val Pro
        595                 600                 605
Trp Asn Ala Ser Trp Ser Asn Lys Ser Leu Asp Arg Ile Trp Asn Asn
    610                 615                 620
Met Thr Trp Met Glu Trp Glu Arg Glu Ile Asp Asn Tyr Thr Gly Leu
625                 630                 635                 640
Ile Tyr Asn Leu Ile Glu Glu Ser Gln Asn Gln Gln Glu Lys Asn Glu
```

```
                    645                 650                 655
Gln Glu Leu Leu Ala Leu Asp Lys Trp Ala Ser Leu Trp Asn Trp Phe
                660                 665                 670
Asp Ile Thr Asn Trp Leu Trp Tyr Ile Lys Ile Phe Ile Met Ile Val
                675                 680                 685
Gly Gly Leu Ile Gly Leu Arg Ile Val Phe Thr Val Leu Ser Ile Val
                690                 695                 700
Asn Arg Val Arg Gln Gly Tyr Ser Pro Leu Ser Phe Gln Thr His His
705                 710                 715                 720
Pro Ala Gln Arg Glu Pro Asp Arg Pro Glu Gly Ile Glu Gly Glu Gly
                725                 730                 735
Gly Glu Arg Asp Arg Asp Arg Ser Gly Pro Leu Val Asp Gly Phe Leu
                740                 745                 750
Ala Ile Ile Trp Val Asp Leu Arg Ser Leu Cys Ile Phe Leu Tyr His
                755                 760                 765
Arg Leu Arg Asp Leu Leu Leu Ile Val Thr Arg Ile Val Glu Leu Leu
                770                 775                 780
Gly Arg Arg Gly Trp Glu Val Leu Lys Tyr Trp Trp Asn Leu Leu Gln
785                 790                 795                 800
Tyr Trp Ser Gln Glu Leu Lys Asn Ser Ala Ile Asn Leu Leu Asn Ala
                805                 810                 815
Thr Ala Ile Ala Val Ala Glu Gly Thr Asp Arg Val Ile Glu Ile Leu
                820                 825                 830
Gln Arg Ala Phe Arg Ala Ile Leu His Ile Pro Thr Arg Ile Arg Gln
                835                 840                 845
Gly Leu Glu Arg Ala Leu Leu
850                 855

<210> SEQ ID NO 17
<211> LENGTH: 2571
<212> TYPE: DNA
<213> ORGANISM: HIV-1

<400> SEQUENCE: 17
atgagagtga agggqatcaq gaacaattgg cagcacttat ggagatgggg caccatgctc      60
cttgggatgt tgatgatctg tagtgctaca gaacaattgt gggtcacagt ctattatggg     120
gttcctgtgt ggagagaagc aacaaccact ctattctgtg catcagattc taaagcatat     180
gatacagagg cacataatgt ttgggccaca catgcctgtg tacccacaga ccccaaccca     240
caagaagtat tattggaaaa tgtgacagaa aattttaaca tgtggaaaaa tgacatggta     300
gaacagatgc atgaggatat aatcagtcta tgggatcaaa gcctaaagcc atgtgtaaaa     360
ctaaccccac gttgtgttac tttaaagtgc actgattatg agggaaatgc taataatacc     420
attgataatg ccactaaaaa tagctggaaa ggagaaaata aaaattgcac tttcaatgtc     480
accacagcca taagagataa ggtgaagaaa caatatgcac ttttttcatag tcttgatgta     540
gtcccaataa aagatgctaa ggatagtaac agctataggt tgataagttg taacacctca     600
gtcattacac aggcttgtcc aaagacatcc tttgagccaa ttcccatata ttattgtgcc     660
ccggctgggt ttgcgattct aaaatgtaac aataagacat tcagtggaaa aggacaatgt     720
aaaaatgtca gcacagtaca atgtacacat ggaattaggc cagtagcatc aactcaactg     780
ctgttaaatg gcagtctagc agaagaagag ataataatta gatctgacaa tttcacaaac     840
aatgctaaaa tcataatagt acagctgaaa gaacctgtag aaattaattg tacaaggccc     900
```

-continued

```
ggcaacaata caagaaaaag tatacatata ggaccaggga gagcatggta tgcaacagga       960
gatataatag gagatataag acaagcacat tgcaacctta gtagtgtaaa atggaataac      1020
actttaagac agatagctaa aaaattagga gaacaatttc aggataaaaa tataacccttt     1080 aagcaatcct caggagggga cccagaaatt gtaatgcaca gttttaattg tgggggggaa      1140 ttttctact gtaatgcaac acaactgttt aatagtacct gggataatgg tacttggaat       1200
aacagtactt ggaatgaaac tgatactacc actatcacac tcccatgcag gataaaacaa      1260
attgtaaaca tgtggcagac agtaggaaga gcaatgtatg cccctcccat tagaggagaa      1320
attagttgtt catcaaatat tacagggctg ctattaacaa gagatggtgg taatataaat      1380
gagacaaatg ggactgagat ctttagacct gcaggaggag atatgaggga caattggaga     1440
agtgaattat ataaatataa agtagtaaaa attgaaccat taggaatagc acccaccaag     1500
gcaaagagaa gagtggtgca gagagaaaaa agagcagtgg gagtaggagc tatgttcctt     1560
gggttcttgt cagcagcagg aagcactatg gcgcagcgt cagtgacgct gacggtacag      1620
gccagacaat tattgtctgg tatagtgcaa cagcagaaca atttgctgag ggctattgag     1680
gcgcaacatc atctgttgca actcacagtc tggggcatca agcagctcca ggcaagagtc     1740
ctggctgtgg aaagatacct aggggatcaa cagctcctgg ggatttgggg ttgctctgga    1800
aaactcatct gcaccactac tgtgccttgg aatactagtt ggagtaataa atcactgaaa    1860
tacatttggg ataacatgac ctggatgcag tgggataaag aaattagcaa ttacacaggc    1920
ttaatataca ccttaattga ggaatcgcag aaccagcaag aaaagaatga aaaggaacta    1980
ctggaattgg ataaatgggc aagtttgtgg aattggtttg acataacaaa ctggctgtgg    2040
tatataaaaa tattcataat aatagtagga ggcttgatag gtttaagaat agttttttact  2100 gtactttcta tagtgaatag agttaggcag ggatactcac cactatcgtt tcagacccgc   2160
ctcccaaccc agaggggacc cgacaggccc gaaggaatcg aagaagaagg tggagagaga   2220
gacagagaca gatcaagaac atcagtggat ggattcttag cacttatctg ggtcgatcta   2280
cggagcctgt gcctcttcag ctaccaccgc ttgagagact tactcttgat tctagcgagg    2340
attgtggaac ttctgggacg ccggggggtgg gaaaccctca gatattggtg gaatctccta    2400
cagtattgga gtcaggaact aaagaatagt gctgttagct tgcttaattc tatagccata    2460
gtagtagctg agggaacaga taggggttata gaagtagtac agagagtttg tagagctatc    2520
cgccacatac ctagaagaat aagacagggc ttggaaaggg ctttgctata a              2571
```

<210> SEQ ID NO 18
<211> LENGTH: 854
<212> TYPE: PRT
<213> ORGANISM: HIV-1

<400> SEQUENCE: 18

```
Met Arg Val Lys Ile Asn Asn Trp Gln His Leu Trp Arg Trp Gly Thr
1               5                   10                  15

Met Leu Leu Gly Met Leu Met Ile Cys Ser Ala Thr Glu Gln Leu Trp
            20                  25                  30

Val Thr Val Tyr Tyr Gly Val Pro Val Trp Arg Glu Ala Thr Thr Thr
        35                  40                  45

Leu Phe Cys Ala Ser Asp Ser Lys Ala Tyr Asp Thr Glu Ala His Asn
    50                  55                  60

Val Trp Ala Thr His Ala Cys Val Pro Thr Asp Pro Asn Pro Gln Glu
65                  70                  75                  80
```

-continued

```
Val Leu Leu Glu Asn Val Thr Glu Asn Phe Asn Met Trp Lys Asn Asp
                85                  90                  95
Met Val Glu Gln Met His Glu Asp Ile Ile Ser Leu Trp Asp Gln Ser
            100                 105                 110
Leu Lys Pro Cys Val Lys Leu Thr Pro Arg Cys Val Thr Leu Lys Cys
        115                 120                 125
Thr Asp Tyr Glu Gly Asn Ala Asn Asn Thr Ile Asp Asn Ala Thr Lys
    130                 135                 140
Asn Ser Trp Lys Gly Glu Ile Lys Asn Cys Thr Phe Asn Val Thr Thr
145                 150                 155                 160
Ala Ile Arg Asp Lys Val Lys Gln Tyr Ala Leu Phe His Ser Leu
                165                 170                 175
Asp Val Val Pro Ile Lys Asp Ala Lys Asp Ser Asn Ser Tyr Arg Leu
            180                 185                 190
Ile Ser Cys Asn Thr Ser Val Ile Thr Gln Ala Cys Pro Lys Val Ser
        195                 200                 205
Phe Glu Pro Ile Pro Ile His Tyr Cys Ala Pro Ala Gly Phe Ala Ile
    210                 215                 220
Leu Lys Cys Asn Asn Lys Thr Phe Ser Gly Lys Gly Gln Cys Lys Asn
225                 230                 235                 240
Val Ser Thr Val Gln Cys Thr His Gly Ile Arg Pro Val Ala Ser Thr
                245                 250                 255
Gln Leu Leu Leu Asn Gly Ser Leu Ala Glu Lys Asp Ile Ile Ile Arg
            260                 265                 270
Ser Asp Asn Phe Ser Asp Asn Ala Lys Ile Ile Val Gln Leu Lys
        275                 280                 285
Glu Pro Val Glu Ile Asn Cys Thr Arg Pro Gly Asn Asn Thr Arg Lys
    290                 295                 300
Ser Ile His Ile Gly Pro Gly Arg Ala Trp Tyr Ala Thr Gly Asp Ile
305                 310                 315                 320
Ile Gly Asp Ile Arg Gln Ala His Cys Asn Leu Ser Ser Val Lys Trp
                325                 330                 335
Asn Asn Thr Leu Arg Gln Ile Ala Lys Lys Leu Gly Glu Gln Phe Gln
            340                 345                 350
Asp Lys Asn Ile Thr Phe Lys Gln Ser Ser Gly Gly Asp Pro Glu Ile
        355                 360                 365
Val Met His Ser Phe Asn Cys Gly Gly Glu Phe Phe Tyr Cys Asn Ala
    370                 375                 380
Thr Gln Leu Phe Asn Ser Thr Trp Phe Asn Gly Thr Trp Asn Asn Ser
385                 390                 395                 400
Thr Trp Asn Glu Thr Asp Thr Thr Ile Thr Leu Pro Cys Arg Ile
                405                 410                 415
Lys Gln Ile Val Asn Met Trp Gln Thr Val Gly Arg Ala Met Tyr Ala
            420                 425                 430
Pro Pro Ile Arg Gly Glu Ile Ser Cys Ser Ser Asn Ile Thr Gly Leu
        435                 440                 445
Leu Leu Thr Arg Asp Gly Gly Asn Ile Asn Glu Thr Asn Gly Thr Glu
    450                 455                 460
Ile Phe Arg Pro Ala Gly Gly Asp Met Arg Asp Asn Trp Arg Ser Glu
465                 470                 475                 480
Leu Tyr Lys Tyr Lys Val Val Lys Ile Glu Pro Leu Gly Ile Ala Pro
                485                 490                 495
Thr Lys Ala Lys Arg Arg Val Val Gln Arg Glu Lys Arg Ala Val Gly
```

```
                  500             505             510
Val Gly Ala Met Phe Leu Gly Phe Leu Ser Ala Ala Gly Ser Thr Met
            515                 520                 525

Gly Ala Ala Ser Val Thr Leu Thr Val Gln Ala Arg Gln Leu Leu Ser
            530                 535                 540

Gly Ile Val Gln Gln Asn Asn Leu Leu Arg Ala Ile Glu Ala Gln
545                 550                 555                 560

Gln His Leu Leu Gln Thr Leu Val Trp Gly Ile Lys Gln Leu Gln Ala
                565                 570                 575

Arg Val Leu Ala Val Glu Arg Tyr Leu Gly Asp Gln Gln Leu Leu Gly
            580                 585                 590

Ile Trp Gly Cys Ser Gly Lys Leu Ile Cys Thr Thr Val Pro Trp
            595                 600                 605

Asn Thr Ser Trp Ser Asn Lys Ser Leu Lys Tyr Ile Trp Asp Asn Met
            610                 615                 620

Thr Trp Met Gln Trp Asp Lys Glu Ile Ser Asn Tyr Thr Gly Leu Ile
625                 630                 635                 640

Tyr Thr Leu Ile Glu Glu Ser Gln Asn Gln Gln Glu Lys Asn Glu Lys
                645                 650                 655

Glu Leu Leu Glu Leu Asp Lys Trp Ala Ser Leu Trp Asn Trp Phe Asp
            660                 665                 670

Ile Thr Asn Trp Leu Trp Tyr Ile Lys Ile Phe Ile Ile Val Gly
            675                 680                 685

Gly Leu Ile Gly Leu Arg Ile Val Phe Thr Val Leu Ser Ile Val Asn
            690                 695                 700

Arg Val Arg Gln Gly Tyr Ser Pro Leu Ser Phe Gln Thr Arg Leu Pro
705                 710                 715                 720

Thr Gln Arg Gly Pro Asp Arg Pro Glu Gly Ile Glu Glu Gly Gly
                725                 730                 735

Glu Arg Asp Arg Asp Arg Ser Arg Thr Ser Val Asp Gly Phe Leu Ala
            740                 745                 750

Leu Ile Trp Val Asp Leu Arg Ser Leu Cys Leu Phe Ser Tyr His Arg
            755                 760                 765

Leu Arg Asp Leu Leu Leu Ile Leu Ala Arg Ile Val Glu Leu Leu Gly
770                 775                 780

Arg Arg Gly Trp Glu Thr Leu Arg Tyr Trp Trp Asn Leu Leu Gln Tyr
785                 790                 795                 800

Trp Ser Gln Glu Leu Lys Asn Ser Ala Val Ser Leu Leu Asn Ser Ile
                805                 810                 815

Ala Ile Val Val Ala Glu Gly Thr Asp Arg Val Ile Glu Val Val Gln
            820                 825                 830

Arg Val Cys Arg Ala Ile Arg His Ile Pro Arg Arg Ile Arg Gln Gly
            835                 840                 845

Leu Glu Arg Ala Leu Leu
        850

<210> SEQ ID NO 19
<211> LENGTH: 2589
<212> TYPE: DNA
<213> ORGANISM: HIV-1

<400> SEQUENCE: 19
atgagagtga aggagatcat gaaaaattat cagcactggt ggagagggggg catcatgctc      60 cttgggttgt taatgatctg tagtgctgct gaacaattgt gggtcacagt ctattatggg     120
```

```
gtacccgtgt ggaaagaagc aaccaccact ctattctgtg catctgatgc taaagcatat      180
gatacagaga aacataatgt ttgggccaca catgcctgtg tacctacaga ccccaaccca      240
caagaagtag tattggaaaa tgtgacagaa aattttaaca tgtggaaaaa taacatggta      300
gaacagatgc atgaggatat aatcagttta tgggatcaaa gtctaaagcc atgtgtaaaa      360
ctaaccccac tctgtgtcac tttaaactgt aggaacgtta ctattaccaa tactactacc      420
aatagtagtg gctggaaact aatggaggaa ggagaaataa aaaactgctc tttcaaaatc      480 accacaaatac tgagacataa gatgcaggaa gaacatgcac ttttttataa atcagatgta      540
gtaccactag gtaataatag tgcaataggt aataataatg ccagatatag gttgataagt      600
tgtaacacct caaccattac acaggcctgt ccaaaggtat cctttgagcc aattcccata      660
cattattgtg ccccggctgg ttttgcgatt ctaaaatgta gagataagaa gttcaatgga      720
acaggaccat gtaaagatgt cagcacagta caatgtacac atggaattaa gccagtagta      780
tcaactcaac tactgttaaa tggcagtcta gcagaagaag atatagtaat tagatctgcc      840
aatttctcag acaatgctaa aatcataata gtacagctga ataaaactgt agtaattaat      900
tgtacaagac ccaacaataa tacaagaaaa ggtataaata taggaccagg aagaacagtt      960
tatgcaacag gaaaaataat aggagatata agacaagcac attgtaacat tagtaaagga     1020
gaatggtata cactttaaa gcaggtagtt acaaaattag gagaacattt taagaataaa     1080
acaatagcct ttaataaatc ctcaggaggg gacccagaaa ttgtaaagca cacttttaat     1140
tgtggagggg aattttctta ctgtgattca acaaaattgt ttactagtac ttggaactat     1200
actaatggta cttggaatag tactaactgg aatgatactg aaatgttgaa taaaacaatc     1260
acactcccat gcagaataaa acaaattgta aacatgtggc aggaagtagg gaaagcaatg     1320
tatgcccctc ccatcagcgg acttattaca tgttcatcaa atattacagg actactatta     1380
acaagagatg gtggtagtaa cacgaacacc accgaggtct tcagacctgg aggaggaaat     1440
atgaaggaca attggagaag tgaattatat aaatataaag tagtaaaaat tgaaccatta     1500
ggagtagcac ccaccaaggc aaaaagaaga gtggtgcaga gagaaaaaag agcagtggga     1560
ataggagctc tgttccttgg gttcttggga gcagcaggaa gcactatggg cgcagcgtca     1620
ctgacgctga cggtacagac cagacaatta ttgtctggta tagtgcagca gcagaacaat     1680
ctgctgaggg ctattgaggc gcaacagcat ctgttgcaac tcacagtctg ggcatcaag     1740 cagctccagg caagagtcct ggctgtggaa agataccta aggatcaaca gctcctgggg     1800
atttggggtt gctctggaaa actcatttgc accactactg tgccttggaa tgctagttgg     1860
agtaataaat ctctggatga tatttggcag aacatgacct ggatggagtg ggaaagagaa     1920
attgacaatt acacaaatgt aatatacaat ttaattgaag aatcgcagaa ccagcaagaa     1980
aagaatgaac aagacttatt agcattggat aaatgggcaa gtttgtggga ttggtttagc     2040
atatcaaact ggctgtggta tataaaaata ttcataatga tagtaggagg cttgataggt     2100
ttaagaataa tttttactgt actttctata gtgaatagag ttaggcaggg atactcacca     2160
ttatcgtttc agacccgctt cccagccccg aggggacccg acaggcccga aggaatcgaa     2220
gaaggaggtg gagagaaaga cagagacaga tccggctat tagtgaacgg attctttgca     2280
cttatctggg tggacctacg gagcctgtgc ctcttcagct accaccgctt gagagactta     2340
ctcttgattg cagcgagaat tgtggagctt ctgggacgca ggggtggga aatcctcaag     2400 tattggtgga atctcctgca gtattggagt caggaactaa agaatagtgc tgttagcttg     2460
```

-continued

```
cttaatgtca cagccatagc agtagctgag gggacagata ggattctaga agtattacaa    2520
agagcttata gagctattat tcacatacct agaagaataa gacagggctt agaaagggct    2580
ttgctataa                                                           2589
```

<210> SEQ ID NO 20
<211> LENGTH: 862
<212> TYPE: PRT
<213> ORGANISM: HIV-1

<400> SEQUENCE: 20

```
Met Arg Val Lys Glu Ile Met Lys Asn Tyr Gln His Trp Trp Arg Gly
1               5                   10                  15

Gly Ile Met Leu Leu Gly Leu Leu Met Ile Cys Ser Ala Ala Glu Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Lys
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Arg Asn Val Thr Ile Thr Asn Thr Thr Thr Asn Ser Ser Gly
    130                 135                 140

Trp Lys Leu Met Glu Glu Gly Glu Ile Lys Asn Cys Ser Phe Lys Ile
145                 150                 155                 160

Thr Thr Ile Leu Arg His Lys Met Gln Glu His Ala Leu Phe Tyr
                165                 170                 175

Lys Ser Asp Val Val Pro Leu Gly Asn Asn Ser Ala Ile Gly Asn Asn
            180                 185                 190

Asn Ala Arg Tyr Arg Leu Ile Ser Cys Asn Thr Ser Thr Ile Thr Gln
        195                 200                 205

Ala Cys Pro Lys Val Thr Phe Glu Pro Ile Pro Ile His Tyr Cys Ala
    210                 215                 220

Pro Ala Gly Phe Ala Ile Leu Lys Cys Arg Asp Lys Lys Phe Asn Gly
225                 230                 235                 240

Thr Gly Pro Cys Lys Asp Val Ser Thr Val Gln Cys Thr His Gly Ile
                245                 250                 255

Lys Pro Val Val Ser Thr Gln Leu Leu Leu Asn Gly Ser Leu Ala Glu
            260                 265                 270

Glu Asp Ile Val Ile Arg Ser Ala Asn Phe Ser Asp Asn Ala Lys Ile
        275                 280                 285

Ile Ile Val Gln Leu Asn Lys Thr Val Val Ile Asn Cys Thr Arg Pro
    290                 295                 300

Asn Asn Asn Thr Arg Lys Gly Ile Asn Ile Gly Pro Gly Arg Thr Val
305                 310                 315                 320

Tyr Ala Thr Gly Lys Ile Ile Gly Asp Ile Arg Gln Ala His Cys Asn
                325                 330                 335

Ile Ser Lys Gly Glu Trp Tyr Asn Thr Leu Lys Gln Val Val Thr Lys
            340                 345                 350
```

-continued

Leu Gly Glu His Phe Lys Asn Lys Thr Ile Ala Phe Asn Lys Ser Ser
        355                 360                 365

Gly Gly Asp Pro Glu Ile Val Lys His Thr Phe Asn Cys Gly Gly Glu
        370                 375                 380

Phe Phe Tyr Cys Asp Ser Thr Lys Leu Phe Thr Ser Thr Trp Asn Tyr
385                 390                 395                 400

Thr Asn Gly Thr Trp Asn Ser Thr Asn Trp Asn Asp Thr Glu Met Leu
                405                 410                 415

Asn Lys Thr Ile Thr Leu Pro Cys Arg Ile Lys Gln Ile Val Asn Met
            420                 425                 430

Trp Gln Glu Val Gly Lys Ala Met Tyr Ala Pro Pro Ile Ser Gly Leu
        435                 440                 445

Ile Thr Cys Ser Ser Asn Ile Thr Gly Leu Leu Thr Arg Asp Gly
        450                 455                 460

Gly Ser Asn Thr Asn Thr Thr Glu Val Phe Arg Pro Gly Gly Gly Asn
465                 470                 475                 480

Met Lys Asp Asn Trp Arg Ser Glu Leu Tyr Lys Tyr Lys Val Val Lys
                485                 490                 495

Ile Glu Pro Leu Gly Val Ala Pro Thr Lys Ala Lys Arg Arg Val Val
            500                 505                 510

Gln Arg Glu Lys Arg Ala Val Gly Ile Gly Ala Leu Phe Leu Gly Phe
        515                 520                 525

Leu Gly Ala Ala Gly Ser Thr Met Gly Ala Ala Ser Leu Thr Leu Thr
        530                 535                 540

Val Gln Thr Arg Gln Leu Leu Ser Gly Ile Val Gln Gln Gln Asn Asn
545                 550                 555                 560

Leu Leu Arg Ala Ile Glu Ala Gln Gln His Leu Leu Gln Thr Leu Val
                565                 570                 575

Trp Gly Ile Lys Gln Leu Gln Ala Arg Val Leu Ala Val Glu Arg Tyr
            580                 585                 590

Leu Lys Asp Gln Gln Leu Leu Gly Ile Trp Gly Cys Ser Gly Lys Leu
        595                 600                 605

Ile Cys Thr Thr Thr Val Pro Trp Asn Ala Ser Trp Ser Asn Lys Ser
        610                 615                 620

Leu Asp Asp Ile Trp Asn Asn Met Thr Trp Met Glu Trp Glu Arg Glu
625                 630                 635                 640

Ile Asp Asn Tyr Thr Asn Val Ile Tyr Asn Leu Ile Glu Glu Ser Gln
                645                 650                 655

Asn Gln Gln Glu Lys Asn Glu Gln Asp Leu Leu Ala Leu Asp Lys Trp
            660                 665                 670

Ala Ser Leu Trp Asp Trp Phe Ser Ile Ser Asn Trp Leu Trp Tyr Ile
        675                 680                 685

Lys Ile Phe Ile Met Ile Val Gly Gly Leu Ile Gly Leu Arg Ile Ile
        690                 695                 700

Phe Thr Val Leu Ser Ile Val Asn Arg Val Arg Gln Gly Tyr Ser Pro
705                 710                 715                 720

Leu Ser Phe Gln Thr Arg Phe Pro Ala Pro Arg Gly Pro Asp Arg Pro
                725                 730                 735

Glu Gly Ile Glu Glu Gly Gly Glu Lys Asp Arg Asp Arg Ser Gly
            740                 745                 750

Leu Leu Val Asn Gly Phe Phe Ala Leu Ile Trp Val Asp Leu Arg Ser
        755                 760                 765

```
    Leu Cys Leu Phe Ser Tyr His Arg Leu Arg Asp Leu Leu Ile Ala
        770                 775                 780

Ala Arg Ile Val Glu Leu Leu Gly Arg Arg Gly Trp Glu Ile Leu Lys
    785                 790                 795                 800

Tyr Trp Trp Asn Leu Leu Gln Tyr Trp Ser Gln Glu Leu Lys Asn Ser
                    805                 810                 815

Ala Val Ser Leu Leu Asn Val Thr Ala Ile Ala Val Ala Glu Gly Thr
                820                 825                 830

Asp Arg Ile Leu Glu Val Leu Gln Arg Ala Tyr Arg Ala Ile Ile His
                835                 840                 845

Ile Pro Arg Arg Ile Arg Gln Gly Leu Glu Arg Ala Leu Leu
        850                 855                 860

<210> SEQ ID NO 21
<211> LENGTH: 2598
<212> TYPE: DNA
<213> ORGANISM: HIV-1

<400> SEQUENCE: 21
atgagagtga aggggacaca gaagagttat ccactcttat ggaggtgggg tataatattt      60
tggataatgg taatttgtaa tgctgaaaat ttgtgggtca cggtctatta tggggtacct     120
gtgtggagag acgcagagac caccttattt tgtgcatcag atgctaaagc atatgataca     180
gaagtacata atgtttgggc tacacatgcc tgtgtaccca cagaccctaa cccacaagaa     240
ataccttggg aaaatgtaac agaaaatttt aatatgtgga aaataacat ggtagagcag     300
atgcatgaag atataattga tctatgggac caaagcctaa agccatgtgt aaagttaacc     360
cctctctgtg ttactttaaa ttgccataac ttcaataact caatagcag caataacagc     420
accccctatca acaacaccat atataatggc atgcaagggg aaataaaaaa ttgctctttc     480
aatacaacca cagaattaag aggtaagaca agaaaacagt atgcactttt taataaactt     540
gatgtagtac aaattaatga taagaataat agtcatagta ataatagacg gtatatgtta     600
atacattgta atacctcaac cattacacag gcttgtccaa aggtaacctt tgagccaatt     660
cccatacatt attgtgcccc agctggtttt gcaattctaa aatgtaagga tcaggagttc     720
aatggatcag gaccatgcaa caatgtcagc acagtacaat gcacacatgg aatcaagcca     780
gtagtatcaa ctcagctgct gttaaatggc agtctagcag aaagaaaaat aatgattaga     840
tctgaaaata tcacaaacaa tgccaagacc ataatagtac agttcactga gcctgtagaa     900
attaattgta ccagacctaa caacaataca agaaaaaggg taggtgtagg accagggcga     960
gcagtctatg taacaaatgc cataataggg gatataagac aagcacattg taatgtcagc    1020
agagcaaaat ggaatgacac tttaaagaag gtagttacac aattaaggaa gcactttaac    1080
acaacaatag tctttactaa accctcagga ggggatgtgg aaattacaac acatagtttt    1140
aactgtggag gagaattttt ctattgcaat acatcacaac tgtttaatag cacttggtat    1200
atcaatggca caaaccacac agggccatat gacactgaca ctataactct ccgatgcaga    1260
ataaagcaaa ttgtaaaaac atggcagaga gtaggacaag caatgtatgc tcctcccatc    1320
ccaggagtaa taggtgtga ctcaaacatt acaggaatat tattaacaag atggaggg     1380
aaaattaata gtacaaatga ctttcagg cctggaggag gagatatgag ggacaattgg    1440
agaagtgaat tatataagta taaagtagta aaaattgaac cactaggtgt agcacccacc    1500
catgcaaaaa gaagagtggt ggagagagaa aaaagagca ttggagtaat aggagctgtc    1560
ttccttgggt tcttaggagc agcaggaagc actatgggcg cagcggcaat aacgctgacg    1620
```

-continued

```
gtacaggcca gacaattatt gtctggtata gtgcaacagc agagcaatct gctgagggct   1680
atagaggctc aacagcatct gttgaaactc acggtctggg gcattaaaca gctccaggca   1740
agagtcctgg ctctggaaag atacctaagg gatcaacagc tcctaggaat ttggggctgc   1800
tctggaaagc tcatctgcac cactaatgta ccctggaatt ctagttggag taataaaact   1860
tttaatgaca tatggaataa catgacctgg ttacaatggg ataaagaaat taacaattac   1920
acaaacacaa tatatcgtct aattgaagaa tcgcagaacc agcaggaaaa gaatgaacaa   1980
gatttattgg cattggacaa gtgggcaagt ctgtggagtt ggtttgacct atcaaattgg   2040
ctatggtata taagaatatt tataatggta gtaggaggtt tgatagcttt aagaatagtt   2100
tttgctgtgc ttgctataat aaatagagtt aggcagggat actcacctct atcattccag   2160
acccttaccc accaccagag ggaacccgac aggcccgaag gaatcgaaga aggaggtggc   2220
gagcaagaca gagacaggtc cgtgagatta gtgaacggat tcttagctct tgcctgggac   2280
gatctacgga gcctgtgcct cttcagctac caccgattga gagacttact cttgattgca   2340
gcgaggactg tggaacttct gggacacagc agtctcaagg gactgagact ggggtgggga   2400
gccctcaaat atctgtggaa tcttctgtca tactggggcc aggaactaaa gaatagtgct   2460
attaatctgc ttgatacaac agcaatagca gtagctaatt ggacagacag agttatagaa   2520
ataggacaaa gatttggtag agctattctc aatataccta agaatcag acagggcctc   2580 gaaagggctt tgcaataa                                                 2598
```

<210> SEQ ID NO 22
<211> LENGTH: 864
<212> TYPE: PRT
<213> ORGANISM: HIV-1

<400> SEQUENCE: 22

```
Met Arg Val Lys Thr Gln Lys Ser Tyr Pro Leu Leu Trp Arg Trp Gly
 1               5                  10                  15

Ile Ile Phe Trp Ile Met Val Ile Cys Asn Ala Glu Asn Leu Trp Val
            20                  25                  30

Thr Val Tyr Tyr Gly Val Pro Val Trp Arg Asp Ala Glu Thr Thr Leu
        35                  40                  45

Phe Cys Ala Ser Asp Ala Lys Ala Tyr Asp Thr Glu Val His Asn Val
    50                  55                  60

Trp Ala Thr His Ala Cys Val Pro Thr Phe Pro Asn Pro Gln Glu Ile
65                  70                  75                  80

Pro Leu Glu Asn Val Thr Glu Asn Phe Asn Met Trp Lys Asn Asn Met
                85                  90                  95

Val Glu Gln Met His Glu Asp Ile Ile Ser Asp Trp Asp Gln Ser Leu
            100                 105                 110

Lys Pro Cys Val Lys Leu Thr Pro Leu Cys Val Thr Leu Asn Cys Thr
        115                 120                 125

His Asn Phe Asn Asn Phe Asn Ser Ser Asn Ser Thr Pro Ile Asn
    130                 135                 140

Asn Thr Ile Tyr Asn Gly Met Gln Gly Glu Ile Lys Asn Cys Ser Phe
145                 150                 155                 160

Asn Thr Thr Thr Glu Leu Arg Gly Lys Thr Lys Gln Tyr Ala Leu
                165                 170                 175

Phe Asn Lys Leu Asp Val Val Gln Ile Asn Asp Lys Asn Asn Ser His
            180                 185                 190
```

```
Ser Asn Asn Arg Arg Tyr Met Leu Ile His Cys Asn Thr Ser Val Ile
        195                 200                 205

Thr Gln Ala Cys Pro Lys Val Thr Phe Glu Pro Ile Pro Ile Tyr Tyr
    210                 215                 220

Cys Ala Pro Ala Gly Phe Ala Ile Leu Lys Cys Lys Asp Gln Glu Phe
225                 230                 235                 240

Asn Gly Ser Gly Pro Cys Asn Asn Val Ser Thr Val Gln Cys Thr His
                245                 250                 255

Gly Ile Lys Pro Val Val Ser Thr Gln Leu Leu Asn Gly Ser Leu
                260                 265                 270

Ala Glu Arg Lys Ile Met Ile Arg Ser Glu Asn Ile Thr Asn Asn Ala
        275                 280                 285

Lys Thr Ile Ile Val Gln Phe Thr Glu Pro Val Glu Ile Asn Cys Thr
    290                 295                 300

Arg Pro Asn Asn Asn Thr Arg Lys Arg Val Gly Val Gly Pro Gly Arg
305                 310                 315                 320

Ala Val Tyr Val Thr Asn Ala Ile Ile Gly Asp Ile Arg Gln Ala Tyr
                325                 330                 335

His Asn Val Ser Arg Ala Lys Trp Asn Asp Thr Leu Lys Lys Val Val
        340                 345                 350

Thr Gln Leu Arg Lys His Phe Asn Thr Thr Ile Val Phe Thr Lys Pro
    355                 360                 365

Ser Gly Gly Asp Val Glu Ile Thr Thr His Ser Phe Asn Cys Gly Gly
    370                 375                 380

Glu Phe Phe Tyr Cys Asn Thr Ser Gln Leu Phe Asn Ser Thr Trp Ile
385                 390                 395                 400

Ile Asn Gly Thr Asn His Thr Gly Pro Tyr Asp Thr Asp Thr Ile Thr
                405                 410                 415

Leu Arg Cys Arg Ile Lys Gln Ile Val Lys Thr Trp Gln Arg Val Gly
        420                 425                 430

Gln Ala Met Tyr Ala Pro Pro Ile Pro Gly Val Ile Arg Cys Asp Ser
    435                 440                 445

Asn Ile Thr Gly Ile Leu Leu Thr Arg Asp Gly Gly Lys Ile Asn Ser
450                 455                 460

Thr Asn Glu Thr Phe Arg Pro Gly Gly Gly Asp Met Arg Asp Asn Trp
465                 470                 475                 480

Arg Ser Glu Leu Tyr Lys Tyr Lys Val Val Lys Ile Glu Pro Leu Gly
                485                 490                 495

Val Ala Pro Thr His Ala Lys Arg Arg Val Val Glu Arg Glu Lys Arg
        500                 505                 510

Ala Val Gly Val Ile Gly Ala Val Phe Leu Gly Phe Leu Gly Ala Ala
    515                 520                 525

Gly Ser Thr Met Gly Ala Ala Ala Ile Thr Leu Thr Val Gln Ala Arg
530                 535                 540

Gln Leu Leu Ser Gly Ile Val Gln Gln Ser Asn Leu Leu Arg Ala
545                 550                 555                 560

Ile Glu Ala Gln Gln His Leu Leu Lys Thr Leu Val Trp Gly Ile Lys
                565                 570                 575

Gln Leu Gln Ala Arg Val Leu Ala Leu Glu Arg Tyr Leu Arg Asp Gln
        580                 585                 590

Gln Leu Leu Gly Ile Trp Gly Cys Ser Gly Lys Leu Ile Cys Thr Thr
    595                 600                 605

Asn Val Pro Trp Asn Ser Ser Trp Ser Asn Lys Thr Phe Asn Asp Ile
```

```
                610             615             620
Trp Asn Met Thr Trp Leu Gln Trp Asp Lys Glu Ile Asn Asn Tyr Thr
625                 630                 635                 640

Asn Thr Ile Tyr Arg Leu Ile Glu Glu Ser Gln Asn Gln Gln Glu Lys
                645                 650                 655

Asn Glu Gln Asp Leu Leu Ala Leu Asp Lys Trp Ala Ser Leu Trp Ser
            660                 665                 670

Trp Phe Asp Leu Ser Asn Trp Leu Trp Tyr Ile Arg Ile Phe Ile Met
        675                 680                 685

Val Val Gly Gly Leu Ile Ala Leu Arg Ile Val Phe Ala Val Leu Ala
690                 695                 700

Ile Ile Asn Arg Val Arg Gln Gly Tyr Ser Pro Leu Ser Phe Gln Thr
705                 710                 715                 720

Leu Thr His His Gln Arg Glu Pro Asp Arg Pro Glu Gly Ile Glu Glu
                725                 730                 735

Gly Gly Gly Glu Gln Asp Arg Asp Arg Ser Val Arg Leu Val Asn Gly
            740                 745                 750

Phe Leu Ala Leu Ala Trp Asp Asp Leu Arg Ser Leu Cys Leu Phe Ser
        755                 760                 765

Tyr His Arg Leu Arg Asp Leu Leu Leu Ile Ala Ala Arg Thr Val Glu
770                 775                 780

Leu Leu Gly His Ser Ser Leu Lys Gly Leu Arg Leu Gly Trp Gly Ala
785                 790                 795                 800

Leu Lys Tyr Leu Trp Asn Leu Leu Ser Tyr Trp Gly Gln Glu Leu Lys
                805                 810                 815

Asn Ser Ala Ile Asn Leu Leu Asp Thr Thr Ala Ile Ala Val Ala Asn
            820                 825                 830

Trp Thr Asp Arg Val Ile Glu Ile Gly Gln Arg Phe Gly Arg Ala Ile
        835                 840                 845

Leu Asn Ile Pro Arg Arg Ile Arg Gln Gly Leu Glu Arg Ala Leu Gln
850                 855                 860

<210> SEQ ID NO 23
<211> LENGTH: 24
<212> TYPE: DNA
<213> ORGANISM: Primer

<400> SEQUENCE: 23
ctggaagcat ccaggaagtc agcc                                      24

<210> SEQ ID NO 24
<211> LENGTH: 24
<212> TYPE: DNA
<213> ORGANISM: Primer

<400> SEQUENCE: 24
gtccccagcg gaaagtccct tgta                                      24

<210> SEQ ID NO 25
<211> LENGTH: 25
<212> TYPE: DNA
<213> ORGANISM: Primer

<400> SEQUENCE: 25
gagacagtgg caatgagagt gaagg                                     25

<210> SEQ ID NO 26
```

-continued

```
<211> LENGTH: 26
<212> TYPE: DNA
<213> ORGANISM: Primer

<400> SEQUENCE: 26
ctttttgacc acttgccacc catctt                                        26

<210> SEQ ID NO 27
<211> LENGTH: 7
<212> TYPE: PRT
<213> ORGANISM: Peptide

<400> SEQUENCE: 27

His Ser Ser Leu Lys Gly Leu
1               5
```

METHODS AND MATERIALS RELATING TO CD8-TROPIC HIV-1

RELATED APPLICATIONS

The present application claims priority benefit of U.S. Provisional Application No. 60/258,472 filed Dec. 28, 2000 which is herein incorporated by reference in its entirety.

Scientific work relating to the present invention was supported by two grants from the National Institutes of Health AI42715 and AI 44974. The United States government may have certain rights in the invention.

FIELD OF THE INVENTION

The present invention relates to human immunodeficiency viruses 1 (HIV-1) that infect CD8-positive T lymphocytes using CD8 as a receptor, to detection methods for the viruses and to prophylactic and therapeutic methods for infection by the viruses.

BACKGROUND

HIV-1 is considered to be the causative agent of Acquired Immunodeficiency Syndrome (AIDS) in the United States. HIV-1 infection is characterized by an asymptomatic period between infection with the virus and the development of AIDS. The rate of progression to AIDS varies among infected individuals. AIDS involves the infection and eventual depletion of a particular type of cell of the immune system, cells that have a protein named CD4 protein on their surface (CD4-positive cells). Helper T cells and monocytes/macrophages are CD4-positive cells.

The process by which HIV-1 infects human cells involves interaction of proteins on the surface of the virus with proteins on the surface of the cells. The common understanding is that the first step in HIV infection is the binding of HIV-1 glycoprotein (gp) 120 to cellular CD4 protein. The viral gp120 then changes conformation or shape and binds to yet other cell surface proteins, such as CCR5 or CXCR4 proteins, allowing subsequent fusion of the virus with the cell. CD4 has thus been described as the primary receptor for HIV-1 and the other cell surface proteins as coreceptors for HIV-1.

More recently, there have been reports of certain HIV-1 viruses that can infect cells without binding to CD4. In Dumonceaux et al., *J. Virol.*, 72(1): 512–519 (1998), the authors describe an HIV-1 strain that is capable of infecting cells that do not have CD4 on their surface. They observe that the amino acid sequence of the gp120 of that HIV-1 strain had changed in a way that altered the gp120 conformation and enabled it to bind to the coreceptor CXCR4 without first binding to CD4. The HIV-1 strain described in the article is a long-term laboratory culture rather than a primary isolate (a virus sample obtained directly from an infected individual). In Kolchinsky et al., *J. Virol.*, 73(10): 8120–8126 (1999), the authors report adapting a HIV-1 virus to infect canine cells lacking CD4 on their surface. The adapted virus was able to bind CCR5 without first binding CD4. They also attribute this CD4-independent infection to changes in the amino acid sequence and conformation of the gp120 of their virus.

While the foregoing reports involved HIV-1 sequence changes in the laboratory, HIV-1 is known to undergo sequence changes in infected individuals. Termed viral evolution, viral sequence changes are believed to be one of the mechanisms by which HIV-1 evades the human immune response. For example, HIV-1 sequence changes that allow it to utilize different coreceptors and thereby infect different types of cells have been described in Shankarappa et al., *J. Virol.*, 73(12): 10489–10502 (1999) and Hoffman et al., *Proc. Natl. Acad. Sci. USA*, 95:11360–11365 (1998).

Another type of immune system cell, cytotoxic T lymphocytes that express the CD8 protein on their surface (CD8-positive cells), play an important protective role against HIV-1. CD8-positive T cells kill HIV-infected cells and release antiviral factors which are thought to inhibit the replication of HIV-1 and prevent progression to AIDS. Previous studies have demonstrated that HIV-1 can occasionally infect CD8-positive T cells, but infection of the CD8-positive cells was attributed to binding of the virus to CD4 receptors on the cells. See, Flamand et al., *Proc. Natl. Acad. Sci. USA*, 95: 3111–3116 (1998) and Kitchen et al., *J. Virol.*, 72: 9054–9060 (1998). The authors of Kaneko et al., *J. Virol.*, 7(11): 8918–8922 (1997) had previously reported that HIV-2 gp105, but not HIV-1 gp120, can bind to the CD8 protein on human cells. HIV-2 is another human immunodeficiency virus that causes AIDS and is prevalent in developing countries. It is more closely related to simian immunodeficiency virus (SIV) than to HIV-1 but also uses CD4 as its primary receptor for infection. Declines in both the number of CD8-positive T cells and specific anti-HIV cytotoxic activity are associated with the onset of AIDS.

There thus remains a need in art for a more complete understanding of the type of human cells infected by HIV-1 as well as the mechanism by which infection occurs to allow the development of vaccines to prevent, and drugs to treat, HIV-1 infection.

SUMMARY OF THE INVENTION

The present invention provides methods and materials for detecting, preventing and treating HIV-1 infection that relate to the previously unrecognized ability of HIV-1 to infect human CD8-positive cells using CD8 as a receptor. HIV-1 viruses that infect CD8-positive cells using CD8 as a receptor are defined herein as CD8-tropic HIV-1. CD8-tropic HIV-1 may or may not utilize one or more other receptors/coreceptors to infect CD8-positive cells.

The CD8-positive cells infected by CD8-tropic HIV-1 may be CD4-negative or CD4-positive. CD8-tropic HIV-1 that retain the ability to infect CD4-positive, CD8-negative cells are defined herein as dual (CD4/CD8)-tropic HIV-1.

Therefore in one aspect the invention provides CD8-tropic HIV-1. Exemplary CD8-tropic HIV-1 are named AD3.v6 and AD3.v22. AD3.v6 and AD3.v22 are dual tropic viruses which were isolated from a single individual. Additional examples of CD8-tropic viruses are named 92UG046-T8, 93UG086-T8, 92US077-T8, 93US 143-T8, 96USHIPS4-T8, 96USHIPS9-T8 and 96USSN20-T8 which are also dual tropic viruses isolated from seven different individuals. Other CD8-tropic HIV-1 can be isolated from an infected individual as follows. Viruses from a patient (as routinely isolated from viral supernatants or plasma) are first used to infect a purified (CD4-positive cell-depleted) population of CD8-positive cells. The infected population is then further purified by sorting the cells by FACS after labeling with anti-CD8 and anti-CD4 antibodies and selecting CD8-positive, CD4-negative cells. The sorted cells are then confirmed to be CD4-negative by testing for the absence of mRNA for CD4. The sorted cells which are highly purified CD8-positive cells are then cultured for growth by methods standard in the art of CD8-tropic HIV-1.

Also provided by the invention are isolated gp120 polypeptides of CD8-tropic HIV-1. The sequences of illustrative gp120 polypeptides, those of AD3.v6 and AD3.v22, are set out in FIG. 3 (SEQ ID NO: 2 and 4, respectively) and those of 92UG046-T8, 93UG086-T8, 92US077-T8. 93US143-T8, 96USHIPS4-T8, 96USHIPS9-T8 and 96USSN20-T8 are set out in FIG. 6 (SEQ ID NOS: 10, 12, 14, 16, 18, 20 and 22, respectively). The polypeptides may be full length gp120 polypeptides as well as gp120 polypeptide fragments that comprise an antigenic epitope unique to a CD8-tropic HIV-1 or comprise a binding site for CD8 unique to a CD8-tropic HIV-1. These gp120 fragments may result from truncations at the amino terminus (with or without a leader sequence), truncations at the carboxy terminus, and/or deletions internal to the polypeptide. The isolated gp120 polypeptides of the CD8-tropic viruses of the present invention include regions within the polypeptide which are contemplated to confer the ability to utilize CD8 as a receptor. Therefore, fragments which include one or more of these regions are provided by the invention. The CD8-tropic HIV-1 gp120 polypeptides may be a chimeric polypeptide comprising amino acids from a different CD8-tropic HIV-1 or comprising amino acids other than CD8-tropic HIV-1 amino acids. The activity of the viruses comprising gp120 polypeptides of the invention is evaluated by routine screening assays. Examples of screening assays are described herein such as assays detecting viral infection of CD8-positive/CD4-negative cells (e.g., KRCD8) and the ability to form syncitia in CD8-positive/CD4-negative cells.

The invention also provides for CD8-tropic gp120 polypeptides with one or more amino acid substitutions within the V1-V2, C2 and V4 loops. Substitutions within these regions are contemplated to impart CD8-tropism to CD8-tropic viruses. Specifically contemplated are CD8-tropic gp120 polypeptides which have, for example, an isoleucine residue at position 270; a aspartic acid or glutamic acid residue at position 177: a serine residue at position 209; a glutamic acid residue at position 352; and/or a glutamic acid residue at position 442. Also contemplated are CD8-tropic gp41 polypeptides which have, for example, an isoleucine at position 693; a gluatamic acid residue at position 724; an alanine residue at position 779; and/or an insertion of HSSLKGL (SEQ ID NO: 27) within the transmembrane domain.

The invention also provides for CD8-tropic gp120 polypeptides with one or more conservative amino acid substitutions that do not affect the cellular tropism of the virus. Alternatively, the CD8-tropic gp120 polypeptides of the invention are contemplated to have conservative amino acids substitutions which may not confer CD8-tropism but are associated with or enhance CD8-tropism. The term "conservative amino acid substitution" refers to a substitution of a native amino acid residue with a nonnative residue, including naturally occurring and nonnaturally occurring amino acids, such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alanine, as has been previously described for "alanine scanning mutagenesis". Naturally occurring amino acids are characterized based on their side chains as follows: basic: arginine, lysine, histidine; acidic: glutamic acid, aspartic acid; uncharged polar: glutamine, asparagine, serine, threonine, tyrosine; and non-polar: phenylalanine, tryptophan, cysteine, glycine, alanine, valine, proline, methionine, leucine, norleucine, isoleucine General rules for amino acid substitutions are set forth in Table 1 below.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asn |
| Gly | Pro, Ala | Ala |
| His | Asn, Gln, Lys, Arg | Arg |
| Ile | Leu, Val, Met, Ala, Phe, | Leu |
| Leu | Norleucine, Ile, Val, Met, | Leu |
| Lys | Arg, 1,4 Diaminobutyric | Arg |
| Met | Leu, Phe, Ile | Leu |
| Phe | Leu, Val, Ile, Ala, Tyr | Arg |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, | Leu |

The invention provides isolated polynucleotides encoding CD8-tropic HIV-1 gp120 polypeptides of the invention. The polynucleotides may comprise DNA or RNA. The sequences of illustrative gp120 polynucleotides, those of AD3.v6, AD3.v22, 92UG046-T8, 93UG086-T8, 92US077-T8, 93US143-T8, 96USHIPS4-T8, 96USHIPS9-T8 and 96USSN20-T8, respectively, are set out in FIGS. 1, 2 and 7-13 as SEQ ID NOS: 1, 3, 9, 1, 13, 15, 17, 19 and 21. The polynucleotides set out in the figures herein consist of the nucleotide sequence encoding the full length envelope polypeptides (gp120 and gp41). Other CD8-tropic HIV-1 gp120 polynucleotides may be identified and/or isolated by stringent hybridization with AD3.v6 or AD3.v22 polynucleotides or by PCR using primers based on those polynucleotides.

Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65–68° C. or 0.015 M sodium chloride, 0.0015M sodium citrate, and 50% formamide at 42° C. See Sambrook et al., *Molecular Cloning: A Laboratory Manual*, $2^{nd}$ Ed., Cold Spring Harbor Laboratory, (Cold Spring Harbor, N.Y. 1989). More stringent conditions (such as higher temperature, lower ionic strength, higher formamide. or other denaturing agent) may also be used, however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8–7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

Antisense polynucleotides complementary to the polynucleotides encoding the CD8-tropic HIV-1 gp120 polypeptides are also provided.

The invention contemplates that polynucleotides of the invention may be inserted in a vector for amplification or expression. For expression, the polynucleotides are operatively linked to appropriate expression control sequence such as a promoter and polyadenylation signal sequences. Further provided are prokaryotic and eukaryotic cells comprising polynucleotides of the invention. Exemplary prokaryotic hosts include bacteria such as *E. coli, Bacillus, Streptomyces, Pseudomonas, Salmonella* and *Serratia*. Eukaryotic host cell lines may be mammalian cells, such as Chinese hamster ovary cells (CHO), human embryonic kidney cells (HEK), 293 or 293T cells, 3T3 cells, mouse neuroblastoma N2A cells, HeLa cells, mouse L-929 cells, BHK or HaK hamster cell lines; insect cell lines such as SF-5 or Hi-5, or yeast cells such as *Saccharomyces, Pichia, Candida, Hansenula,* and *Torulopsis*.

The term isolated is used herein to refer to a substance removed from, and essentially free of, the other components of the environment in which it naturally exists. For example, a polypeptide is separated from other cellular proteins or a DNA is separated from other DNA flanking it in a genome in which it naturally occurs.

The invention provides antibodies which bind to antigenic epitopes unique to (i.e., are specific for) a CD8-tropic HIV-1. Also provided are antibodies which bind to antigenic epitopes common among multiple CD8-tropic HIV-1 but unique with respect to any other antigenic epitopes. The antibodies may be polyclonal antibodies, monoclonal antibodies, antibody fragments which retain their ability to bind their unique epitope (for example, Fv, Fab and F(ab)2 fragments), single chain antibodies and human or humanized antibodies. Antibodies may be generated by techniques standard in the art.

The invention contemplates methods of eliciting an immune response to a CD8-tropic HIV-1 in an individual wherein the antibodies elicited block binding of CD8-tropic HIV-1 to CD8. In one embodiment, the methods comprise a step of administering an immunogenic dose of a composition comprising a CD8-tropic HIV-1 gp120 polypeptide of the invention. In another embodiment, the methods comprise administering an immunogenic dose of a composition comprising a cell expressing a CD8-tropic HIV-1 gp120 polypeptide of the invention. In yet another embodiment, the methods comprise administering an immunogenic dose of a composition comprising a polynucleotide encoding a CD8-tropic HIV-1 gp120 polypeptide of the invention. The polynucleotide may be a naked polynucleotide not associated with any other nucleic acid or may be in a vector such as a plasmid or viral vector (e.g., adeno-associated virus vector or adenovirus vector). Administration of the compositions may be by routes standard in the art, for example, parenteral, intravenous, oral, buccal. nasal, pulmonary, rectal, or vaginal. The methods may be used in combination in a single individual. The methods may be used prior or subsequent to infection of an individual with HIV-1.

The invention correspondingly provides compositions suitable for eliciting an immune response to CD8-tropic HIV-1, wherein the antibodies elicited block binding of CD8-tropic HIV-1 to CD8. The compositions comprise CD8-tropic HIV-1 gp120 polypeptides of the invention, cells expressing the polypeptide, or polynucleotides encoding the polypeptides. The compositions may also comprise other ingredients such as carriers and adjuvants. An immunogenic dose of a composition of the invention is one that generates, after administration, a detectable humoral and/or cellular immune response in comparison to the immune response detectable before administration or in comparison to a standard immune response before adminstration. The invention contemplates that the immune response resulting from the methods may be protective and/or therapeutic.

Also provided by the invention are methods for detecting CD8-tropic HIV-1. In one embodiment, the methods comprise detecting CD8-tropic HIV-1 gp120 polynucleotide of the invention in a sample using primers or probes that specifically bind to the polynucleotide. Detection of the polynucleotide may be accomplished by numerous techniques routine in the art involving, for example, hybridization and PCR. In another embodiment, the methods comprise detecting CD8-tropic HIV-1 gp120 polypeptide of the invention in a sample using antibodies of the invention. Detection of the polypeptide may also be accomplished by numerous techniques routine in the art such as by ELISA or Western blotting.

The invention includes methods of blocking binding of CD8-tropic HIV-1 to CD8-positive cells in an individual in need thereof. The methods comprise administering antibodies or polypeptides of the invention that block binding of CD8-tropic HIV-1 to CD8. Alternatively, administration of one or more small molecules that block binding of CD8-tropic HIV-1 to CD8 is contemplated. As still another embodiment, the methods comprise administration of anti-CD8 antibodies. In vitro assays may be used to demonstrate the ability of an antibody, polypeptide or small molecule of the invention to block binding of CD8-tropic HIV-1 to CD8.

Pharmaceutical compositions comprising antibodies of the invention, polypeptides of the invention and/or small molecules of the invention that block binding of CD8-tropic HIV-1 to CD8 are provided. The pharmaceutical compositions may consist of one of the foregoing active ingredients alone, may comprise combinations of the foregoing active ingredients or may comprise additional active ingredients used to treat HIV-1 infection, for example, anti-CD8 antibodies, IL-2, protease inhibitors, reverse transcriptase inhibitors, interferons, AZT and cytokines The pharmaceutical compositions may comprise one or more additional ingredients such as pharmaceutically effective carriers. Dosage and frequency of the adminstration of the pharmaceutical compositions are determined by standard techniques and depend. for example, on the weight and age of the individual, the route of administration, and the severity of symptoms. Administration of the pharmaceutical compositions may be by routes standard in the art, for example, parenteral, intravenous, oral, buccal, nasal, pulmonary, rectal, or vaginal.

BRIEF DESCRIPTION OF THE DRAWING

Numerous other aspects and advantages of the present invention will be apparent upon consideration of the following detailed description thereof, reference being made to the drawing wherein:

FIG. 1 is a DNA sequence encoding the gp120 envelope polypeptide of AD3.v6 (SEQ ID NO: 1);

FIG. 2 is a DNA sequence encoding the gp120 envelope polypeptide of AD3.v22 (SEQ ID NO: 3);

FIG. 3 is a DNA sequence encoding the gp120 envelope polypeptide of HXB2 (SEQ ID NO: 5);

FIG. 4A-4C is an alignment of the gp120 envelope polypeptide sequences of AD3.v6 (SEQ ID NO: 2) and AD3.v22 (SEQ ID NO: 4) with the gp120 envelope polypeptide sequences of HXB2 (SEQ ID NO: 6), a prototype CD4-tropic HIV-1 virus, and of WEAU1.6 (SEQ ID NO: 8), the closest matched isolate;

FIG. 5 is a DNA sequence encoding the gp120 envelope polypeptide of WEAU1.6 (SEQ ID NO: 7), FIG. 6A-6D sets out the envelope polypeptide sequences of 92UG046-T8 (SEQ ID NO: 10), 93UG086-T8 (SEQ ID NO: 12), 92US077-T8 (SEQ ID NO: 14), 93US143-T8 (SEQ ID NO: 16), 96USHIPS4-T8 (SEQ ID NO: 18, 96USHIPS9-T8(SEQ ID NO: 20), 96USSN20-T8 (SEQ ID NO: 22), HXB2 (SEQ ID NO: 6; a prototype CD4-tropic HIV-1 virus) and AD3.v6 (SEQ ID NO: 2); wherein the sequences displayed consist of the full length envelope polypeptides (gp120 and gp41) and the residue where the gp120 polypeptide ends is clearly indicated in the figure;

FIG. 7 is a DNA sequence encoding the gp120 envelope polypeptide of 92UG046-T8 (SEQ ID NO: 9);

FIG. 8 is a DNA sequence encoding the gp120 envelope polypeptide of 93UG086-T8 (SEQ ID NO: 11);

FIG. 9 is a DNA sequence encoding the gp120 envelope polypeptide of 92US077-T8 (SEQ ID NO: 13);

FIG. 10 is a DNA sequence encoding the gp120 envelope polypeptide of 93US143-T8 (SEQ ID NO: 15);

FIG. 11 is a DNA sequence encoding the gp120 envelope polypeptide of 96USHIPS4-T8 (SEQ ID NO: 17);

FIG. 12 is a DNA sequence encoding the gp120 envelope polypeptide of 96USHIPS9-T8 (SEQ ID NO: 19); and FIG. 13 is a DNA sequence encoding the gp120 envelope polypeptide of 96USSN20-T8 (SEQ ID NO: 21).

DETAILED DESCRIPTION OF THE DRAWING

The present invention is illustrated by the following examples relating to CD8-tropic HIV-1. Example 1 describes experiments demonstrating the ability of HIV-1 viruses AD3.v6 and AD3.v22 to infect CD8-positive peripheral blood lymphocytes. In Examples 2 and 3, respectively, AD3.v6 and AD3.v22 are shown to use CD8 receptors to infect a CD8-positive, CD4-negative T cell line and to infect CD8-transfected HeLa and COS cell lines. Example 4 describes the ability of anti-CD8 antibodies to inhibit replication of AD3.v6 and Ad3.v22 in primary CD8-positive cells. An analysis of the sequences of the AD3.v6 and AD3.v22 gp120 envelope sequences is presented in Example 5. Examples 6–10 describe the isolation and characterization of additional CD8-tropic quasispecies from various patients. Finally, implications of the CD8-tropism of viruses of the invention are discussed in Example 11.

EXAMPLE 1

HIV-1 viruses AD3.v6 and AD3.v22 were isolated from a single patient and were demonstrated to infect CD8-positive peripheral blood lymphocytes (PBL).

In one type of experiment, PHA-activated total PBL and purified populations of CD4-positive or CD8-positive cells from normal donors were used to compare the replication kinetics of AD3.v6 and AD3.v22 viruses.

Two million PHA-activated (1 $\mu$g/ml) PBL or purified CD4-positive and CD8-positive cells were infected with the HIV-1 isolates for 2 hours at 37° C. using 0.05 pg of p24 per cell. Cells were washed, adjusted to $10^6$ cells/ml and cultured in complete RPMI 1640 medium supplemented with human recombinant IL-2 (50 units/ml) (Life Technologies, Grand Island, N.Y.). Culture supernatants were harvested at regular intervals and stocked at −80° C. until assayed for p24 antigen using a kit (Coulter, Hialeah, Fla.). Phenotyping was performed by FACS at regular intervals using directly labeled anti-CD4 (clone RPA-T4, Zymed Laboratories, San Francisco, Calif.), anti-CD8 (Sigma Chemicals, St. Louis, Mo.) or indirectly labeled anti-CCR5 2D7, Pharmacia International, San Diego, Calif.) and anti-CXCR4 (12G5, J. Hoxie, AIDS Research and Reference Reagent Program) antibodies with appropriate isotype and cell controls.

AD3.v6 and AD3.v22 efficiently replicated in PBL and purified CD4-positive cells. Surprisingly, in repeated experiments, these viruses were also able to replicate in CD8-positive cells at a level that matched the level in PBL and purified CD4-positive cells indicating that CD8-positive lymphocytes are targets for these viruses. CD4-tropic HIV-1/IIIB (AIDS Research and Reagent Program, NIH) was used as a control and primarily replicated in PBL and CD4-positive cells but not in CD8-positive cells.

Several lines of evidence suggest that CD4 played no role in production of AD3.v6 and AD3.v22 by the purified CD8-positive population of cells. First, the phenotypes of purified cells were measured all through the experiments. Only a small number of cells in the CD8-positive population were CD4-positive before infection (0 day), at the time of peak virus production (18 day) or at any point of time in between. Second, compared to purified CD8-positive cells, PBL contained a much larger number of CD4-positive cells. Had CD4-positive cells been the only targets for these viruses, virus production would have been higher in PBL compared to CD8-positive cells. Third, although these viruses were able to replicate in CD4-positive cells, virus production in CD8-positive cells was comparable to that in CD4-positive cells indicating that CD8-positive cells are an equally good target for AD3.v6 and AD3.v22 as CD4-positive cells.

Further evidence that contaminating CD4-positive cells did not produce viruses in purified CD8-positive cells comes from triple-color FACS analyses. Triple-color FACS analyses were performed using a kit from Coulter by fixing the cells first, followed by staining with FITC-p24, CD8-PE and CD4-PC5. At 8 days post infection (8 dpi) when for the first time virus-expressing cells could be detected, most (72.1%) virus-expressing cells were CD8-positive/CD4-negative. The number of CD8-positive/CD4-negative cells expressing HIV-1 increased with progression of infection, and around the time of peak virus production (19 dpi) all HIV-expressing cells were CD8-positive/CD4-negative. Also, in a control experiment where both CD4-positive and CD8-positive cells were removed from PBL and residual (non-CD4/CD8) cells were infected with AD3.v6 or AD3.v22, little or no virus production was detected indicating that any CD8-negative/CD4-negative cells contaminating the CD8-positive population were not be the targets for these viruses Interestingly, expression of CD8 was down-modulated after infection of CD8-positive cells with AD3.v6 or AD3.v22. CD4 was also down-modulated after infection of CD4-positive cells with these viruses suggesting maintenance of CD4-tropism.

In another type of experiment, purified CD8-positive cells were sorted shortly after infection with AD3.v6 or AD3.v22 and these stringently selected CD8-positive cells were tested for expression of CD4 and HIV-1 by RT-PCR to rule out the possibility that the CD8-positive cells were expressing too low a level of CD4 to be detected by FACS.

Briefly, purified CD8-positive cells were FACS sorted after staining with CD8-PE and CD4-PC5 antibodies using a gate to isolate CD8-positive/CD4-negative and CD8-negative/CD4-negative populations. Sorted cells were washed several times and either tested immediately for expression of CD4, CD8 or HIV-1 mRNA by RT-PCR. Total RNA was extracted using Rneasy Mini Kit (Qiagen, Valencia, Calif.). DNA-free RNA was reverse transcribed using Qiagen Omniscript RT system and tested for expression of CD4, CD8, or HIV-1 using specific primers.

Figure 6B:
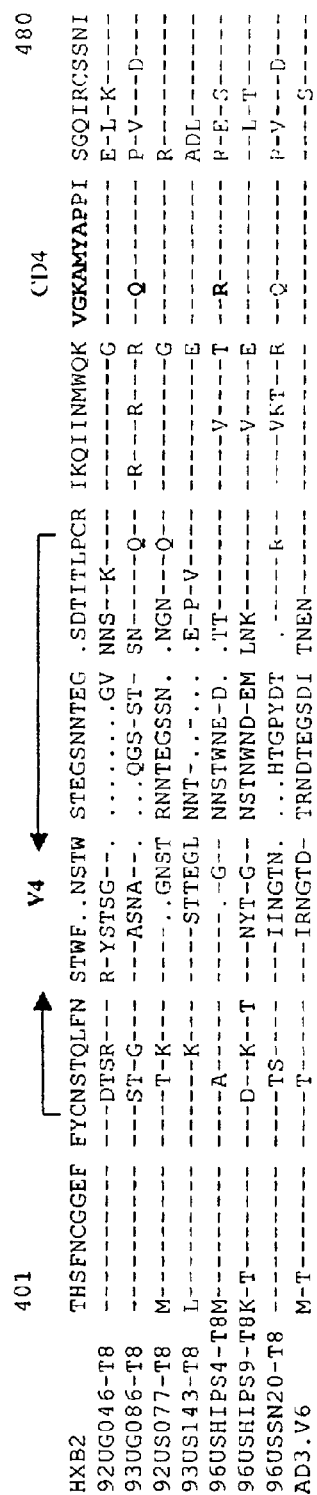

AD3.v6- and AD3.v22-infected and sorted CD8-positive cells expressed CD8 as well as HIV-1 (gag) but no CD4, while uninfected CD8-positive cells expressed CD8 but no CD4 or HIV-1. Similarly sorted CD8-positive cells after infection with CD4-tropic (JR-FL) viruses did not express HIV-1 or CD4. Thus, it is clear that sorted CD8-positive cells were free from CD4-positive cell contamination.

Taken together, these results demonstrate that AD3.v6 and AD3.v22 are able to target CD8-positive/CD4-negative cells and that CD4 played no role in infection of the cells.

EXAMPLE 2

The foregoing experiments with primary CD8-positive cells strongly support that CD8-positive cells are targets for AD3.v6 and AD3.v22. However, since primary cells contain a mixture of different cell types as discussed above, to further establish CD8-tropism of these viruses, additional experiments were performed using a CD8-positive, CD4-negative T-cell line, KRCD8, described in Saha et al., *J. Virol.* 72:876–881 (1998).

KRCD8 were infected as described in Example 1 with AD3.v6, AD3.v22 and HIV-1/IIIB and p24 production was measured at regular intervals. AD3.v6 and AD3.v22, but not HIV-1/IIIB, were able to infect KRCD8 cells. No expression of CD4 was detected in KRCD8 cells whether uninfected or after infection, even by sensitive RT-PCR. These results demonstrate that KRCD8 cells were infected by AD3.v6 and AD3.v22 through a CD4-independent mechanism.

As recent reports of CD4-independent infection with HIV (see articles discussed in the Background) have implicated CCR5 or CXCR4 as the alternative pathway to infection using CD4, the KRCD8 cells were also examined for expression of those coreceptors. Uninfected KRCD8 cells did not express CCR5 or CXCR4 nor did infected KRCD8 cells, indicating that infection of KRCD8 cells was independent of CCR5 or CXCR4.

These studies thus confirm that AD3.v6 and AD3.v22 infect CD8-positive cells in a CD4-independent manner.

Since KRCD8 cells were susceptible to AD3.v6 and AD3.v22, it was investigated whether these viruses used CD8 receptors to infect these lymphoid cells. AD3.v6, AD3.v22 or HIV-1/IIIB viruses were used to infect KRCD8 cells or MT-2 cells (control) in the presence of anti-CD8 (C1) (clone SPV-T8, Zymed Laboratories, San Francisco, Calif.), -CD4 (clone RPA-T4, Zymed Laboratories) or isotype control antibodies. While isotype control or anti-CD4 antibodies had no effect on infection by AD3.v6 or AD3.v22, anti-CD8 antibodies (C1) blocked entry of these viruses into KRCD8 cells. However, anti-CD8 antibodies were not able to prevent infection of CD4-positive MT-2 cells by AD3.v6, AD3.v22 or HIV-1/IIIB viruses. In contrast, anti-CD4 antibodies blocked infection of MT-2 cells by AD3.v6, AD3.v22 and HIV-1/III viruses.

Taken together, these results confirm that AD3.v6 and AD3.v22 use CD8 receptors for infection of CD8-positive cells. The results also demonstrate that these viruses used CD4 receptors to infect CD4-positive cells.

EXAMPLE 3

The ability of AD3.v6 and AD3.v22 to infect cell lines transfected to express CD8 was examined.

First, HeLa T8+ cells, a CD8-transfected tumor cell line that does not express CD4 were examined. HeLa T8+, HeLa T4+ (susceptible to CD4-tropic HIV-1) or parental HeLa cells were infected with AD3.v6, AD3.v22 or HIV-1/III.

Infections of HeLa T8+, HeLa T4+ or parental HeLa cells were performed either by co-culturing cells with infected PBL or with cell-free viruses in the presence of polybrene (2 $\mu$g/ml). After overnight co-culture or infection for 4 hours with cell-free viruses, cells were thoroughly washed, trypsinized and re-plated with fresh medium. Every 5–7 days intervals. cells were trypsinized and re-plated. Culture supernatants were harvested at regular intervals and assayed for p24. For non-productive infections, infection was detected at routine intervals by PCR.

Viral replication was observed between 7–15 days after infection with AD3.v6 and AD3.v22, but not with HIV-1/III. However, all three viruses were able to infect HeLa T4+, but not parental HeLa cells. Like KRCD8 cells, infection of HeLa T8+ cells with AD3.v6 and AD3.v22 was independent of CD4 expression as monitored through RT-PCR. Expression of CD8 was also down-modulated in HeLa T8+ cells after infection with AD3.v6 and AD3.v22 further indicating the role of CD8 as a receptor for those viruses.

The HeLa T8+ cells were also infected with AD3.v6, AD3.v22 or HIV-1/III in the presence of anti-CD8 (C1), anti-CD4 or isotype control antibodies described above. AD3.v6 and AD3.v22 were able to infect HeLa T8+ and HeLa T4+ cells, but not HeLa cells and viral entry into HeLa T8+ cells was blocked with anti-CD8, but not with isotype control or anti-CD4-antibodies. In contrast, viral entry into HeLa T4+ cells was prevented by anti-CD4 antibodies, but not with isotype control or anti-CD8 antibodies. As expected, HIV-1/III viruses were only able to infect HeLa T4+, but not HeLa T8+ or HeLa cells.

Next, to further test the role of CD8 as a receptor for AD3.v6 and AD3.v22, a monkey kidney cell line (COS-T8) that constitutively expressed high levels of human CD8 was generated.

To generate human CD8-expressing COS cells, T8pMV7 vector (AIDS Research & Reagent Program) expressing CD8 was used to transfect COS-7L cells (GIBCO-BRL). Lipofectamine 2000 (GIBCO-BRL), a lipid transfecting reagent was used for transfection according to the manufacturer's instruction. Twenty-four hours post-transfection, cells were re-plated at 1:20 dilution and after another 24 h, cells were put in selection medium. Individual clones were isolated and screened by FACS to select clones expressing CD8.

Like HeLa T8+ cells, AD3.v6 and AD3.v22 viruses were able to infect COS-T8, but not parental COS cells while HIV-1/III viruses failed to infect either of these cell lines. No CD4 expression was detected in COS-T8 cells before or after infection.

These results establish that AD3.v6 and AD3.v22 are able to infect both types of transfected cells using CD8 as a receptor.

EXAMPLE 4

The ability of anti-CD8 antibodies to inhibit replication of AD3.v6 and AD3.v22 in primary CD8-positive cells was tested.

For inhibition of viral replication, specific monoclonal antibodies or isotype control antibodies (5 $\mu$g/ml) were added to purified CD8-positive cells for 30 minutes at room temperature prior to infection. After infection for one hour, cells were washed and re-suspended in culture medium with AD3.v6 or AD3.v22 virus to which respective monoclonal antibodies were added. Culture supernatants were harvested at regular intervals and assayed for p24. Half of the medium was replaced twice every week with fresh medium containing respective antibodies except in some experiments where antibodies were stopped after two weeks.

Replication of AD3.v6 and AD3.v22 viruses was significantly inhibited by anti-CD8 (C1) antibodies, but not by isotype control antibodies. Anti-CD8 antibodies had little effect on replication of these as well as HIV-1/III viruses in CD4-positive cells. As discussed above, AD3.v6 and AD3.v22 have maintained an unchanged ability to use CD4 receptors and should be considered dual (CD4/CD8)-tropic. Since CD4 is co-expressed in some CD8-positive cells, it is conceivable that these viruses may use CD8 as well as CD4 receptors to infect double-positive cells.

EXAMPLE 5

Cellular tropism of HIV-1 is primarily determined by viral envelope polypeptides, in particular gp120. In order to further characterize CD8-tropic HIV-1, DNA encoding gp120 envelopes of AD3.v6 and AD3.v22 was sequenced. Full length envelope coding regions were amplified by nested PCR from genomic DNA using outer (5'-CTGGAAGCATCCAGGAAGTCAGCC-3; SEQ ID NO: 23 and 5'-GTCCCCAGCGGAAAGTCCCTTGTA-3'; SEQ ID NO: 24) and inner (5'-GAGACAGTGGCAATG-AGAGTGAAGG-3'; SEQ ID NO: 25 and 5'-CTTTTTGACCACTTGCCACCCATCTT-3'; SEQ ID NO: 26) primers. Amplified PCR fragment (2.6 kb) was purified and sequenced from both DNA strands by cycle sequencing on an ABI 377 DNA Sequences. Sequence assembly and comparisons were performed with Lasergene (DnaStar, Madison, Wis.) as well as with NCBI Blast Server. The DNA sequence encoding AD3.v6 gp120 envelope polypeptide is set out in FIG. 1, while the DNA sequence of AD3.v22 gp120 is set out in FIG. 2.

An alignment of the protein sequences encoded by the DNAs with the gp120 amino acid sequence of HXB2, a prototype CD4-tropic isolate, and the closest published gp120 amino acid sequence. WEAU1.6, is presented in FIG. 4. In the figure, dashes signify 100% identity among sequences and dots signify the absence/deletion of a base. FIG. 4 display the gp120 polypeptide and clearly the location of the V1, V2, V3, V4 and V5 loops.

Extensive differences exist throughout AD3.v6 and AD3.v22 gp120 when compared with HXB2 and with WEAU1.6. The changes were most extensive in variable (V) loops and a striking feature of these changes was an extended V1-V2 loop. Extensive differences were also present in the important V3 loop when compared to its closest match. In contrast, only a single point change was observed in the entire gp41 between AD3.v6 and AD3.v22 viruses (not shown). Interestingly, the CD4 binding region and other residues that are known to be important for CD4-tropism remained unchanged.

Although no sequence has been definitely been correlated with a specific HIV-1 phenotype, critical residues in gp120 have been identified that are important for cellular tropism through CCR5 or CXCR4 rather than CD4. For example, it has been recently demonstrated that with an IGX motif at positions 348–350 in FIG. 4 in the V3 loop and with a basic residue at position 331, viruses are incapable of using CCR5. These residues (boxed) were identical among AD3.v6, AD3.v22 and HXB2 viruses which cannot use CCR5, suggesting that AD3.v6 and AD3.v22 viruses probably do not use CCR5 co-receptors. Also, CD4-independent infection by viruses using CCR5 has been correlated with specific gp120 changes (italics) resulting in loss of N-linked glycosylation sites at distinct regions. Although extensive changes in V1-V2 loop of AD3.v6 and AD3.v22 viruses were observed, these viruses maintained these specific glycosylation sites (marked with ● in FIG. 4). CD4-independent entry through enhanced use of CXCR4 has also been correlated with seven specific mutations (bold). A specific T to S substitution, not present in either AD3.v6 or AD3.v22, was necessary for CD4-independent infection.

Thus, although AD3.v6 and AD3.v22 viruses use CXCR4 coreceptors for infection of CD4-positive cells (data not shown), CXCR4 and CCR5 apparently are not necessary for infection through CD8 receptors.

EXAMPLE 6

To identify additional CD8-tropic HIV-1, viral stocks from twelve patients were used to test for the presence of CD8-tropic virus. It is contemplated that CD8-tropic HIV quasispecies may be present in a patient at any given time after infection. Although these CD8-tropic viruses exist in an infected patient, these viruses probably are at least initially, outnumbered by the more common CD4-tropic viruses.

Therefore, in order to isolate CD8-tropic viruses from the quasispecies, CD8-tropic virus may be enriched from the original viral stocks. In Example 1, the CD8-tropic HIV-1 viruses AD3.v6 and AD3.v22 were isolated from Herpes virus saimirir (HVS)-transformed CD8-positive T cell clones from a single patient. The additional CD8-tropic HIV-1 viruses described herein (92UG046-T8, 93UG086-T8, 92US077-T8, 93US143-T8, 96USHIPS4-T8, 96USHIPS9-T8 and 96USSN20-T8) were isolated without using HVS by carefully avoiding CD4-tropic contaminants. These procedures eliminated the remote possibility of HVS influencing HIV-tropism.

Twelve primary HIV-1 isolates of different clades (obtained through AIDS Res. & Ref. Program, NIH) were randomly selected. The viruses were originally isolated from different HIV-1-infected patients in North America, Africa and Asia (Table 2). As listed by the AIDS Res. & Ref. Program, these viruses contained CCR5-, CXCR4- or dual (CXCR4/CCR5)-tropic isolates of different clades. In Table 2 these receptors are denoted as R5 (CCR5), X4 (CXCR4) or R5X4 (CXCR4/CCR5).

The approach used to isolate CD8-tropic HIV-1 viruses from infected CD8-positive cells was previously described in Saha et al. *Nature Medicine,* 7: 65–72 (2001). First, purified (CD4-depleted) CD8-positive cells from normal donors were infected with viral stocks from different patients. Three to five days after infection, infected CD8-positive cells were further sorted from contaminant CD4-positive cells by FACS analysis using antibodies against different T cell surface markers including CD4 and CD8, and a very conservative gate to select unadulterated CD8-positive/CD4-negative populations. This analysis reduced the chance of including CD4-tropic isolates that may have been carried through contaminating CD4-positive cells or through the infection of double-positive (CD8-positive/CD4-positive) cells. Finally, CD8-tropic viruses were grown from infected CD8-positive cells by co-culture with CD4-negative depleted cells from normal donors using 0.05 pg of p24/cell.

The resulting infected and sorted CD8-positive cells were tested for the presence of CD4 mRNA and HIV-1 by RT-PCR and PCR. The cells which expressed any CD4 mRNA were discarded from further experiments to avoid any possibility for inclusion of CD4-tropic contaminants. Finally, CD8-tropic viruses were isolated by co-culturing infected (HIV-1 DNA-positive) CD8-positive cells with purified CD8-positive cells from normal donors.

All sorted CD8-positive cells were free from CD4 contamination. At the time of sorting, little or no virus production was detected with most of the infected CD8-positive cell cultures ruling out the possibility of virus-induced down-modulation of CD4 molecules. HIV-1 DNA (gag) was detected in CD8-positive cells from seven out of the twelve patients indicating the possible presence of CD8-tropic isolates in these individuals (Table 2).

TABLE 2

| Patient | Clade | Country | Sex/Age | Disease | CD4-tropism (co-receptor) | HIV-DNA in CD8+ cells |
|---|---|---|---|---|---|---|
| 92UG046 | D | Uganda | M/25 | Asymptomatic | SI, X4 | + |
| 93UG086 | D | Uganda | | | SI, R5X4 | 8 |
| 92US077 | B | USA | Infant | | R5X4 | + |
| 93US143 | B | USA | Infant | | SI, R5X4 | + |
| 96USHiPS4 | B | USA | F/teen-age | AIDS | R5X4 | + |
| 96USHiPS9 | B | USA | | AIDS | R5X4 | + |
| 96USSN20 | A | USA/Senegal | M | AIDS | R2B,3,4,5,X4 | + |
| 92UG001 | D | Uganda | M/26 | Asymptomatic | R5X4 | − |
| 92US727 | B | USA | | | R5 | − |
| 91US056 | B | USA | Infant | | R5 | − |
| 93US151 | B | USA | Infant | | R5X4 | − |
| CMU08 | E | Thailand | | | X4 | − |

Viruses from all twelve patients replicated, albeit at different levels, in CD4-positive cells. HIV-1 viruses from the patients that did not infect CD8-positive cells (e.g. 92UG001, 92US727, 91US056) replicated to a much higher level in CD4-positive cells compared to some of the viruses that were able to infect CD8-positive cells. This suggests that infection of CD8-positive cells is not due to the presence of contaminating CD4-tropic isolates.

Virus production was detected, albeit at lower levels when compared to CD4-positive cells, from CD8-positive cells infected with viruses from five out of the seven patients which tested positive for HIV-1 DNA in CD8-positive cells. The reason for the lack of virus production by CD8-positive cells in spite of being positive for HIV-1 DNA from two patients (96UG046 and 96USHPS9) is not clear. It is possible that viruses from these two patients replicated poorly in CD8-positive cells. However, as described later (see Example 7), viruses from these two patients did replicated in co-culture with CD8-positive cells. These results indicate the presence of CD8-tropic viruses in some of the patients that induced infection in CD8-positive cells, albeit at lower levels compared to CD4-positive cells.

EXAMPLE 7

The foregoing experiments demonstrate the existence of CD8-tropic viruses in various HIV-1 patients. The following studies were carried out to further characterize and substantiate the CD8-tropism of viruses 92UG046-T8, 93UG086-T8, 92US077-T8, 93US143-T8, 96USHIPS4-T8, 96USHIPS9-T8 and 96USSN20-T8. For growth of HIV-1 virus in vitro, short-term co-culture with the target cells from normal donors was necessary. In order to grow CD8-tropic viruses, infected CD8-positive cells from all patients (PCR-positive or -negative for HIV-1 DNA) were co-cultured with purified CD8-positive or CD4-positive cells from normal donors.

As summarized in Table 3 below, production was readily detected when viruses 92UG046-T8, 93UG086-T8, 92US077-T8, 93US143-T8, 96USHIPS4-T8, 96USHIPS9-T8 and 96USSN20-T8 were co-cultured with CD4-positive or CD8-positive cells. With most of the isolates, the levels of virus production were higher in the presence of CD4-positive cells when compared to CD8-positive cells suggesting that like the CD8-tropic viruses AD3.v6 and AD3.v22 (Example 1), the CD8-tropic viruses 92UG046-T8, 93UG086-T8, 92US077-T8, 93US143-T8, 96USHIPS4-T8, 96USHIPS9-T8 and 96USSN20-T8 are also dual (CD4/CD8)-tropic and probably replicate more efficiently in CD4-positive cells.

TABLE 3

| HIV-l/T8 Viruses | RT × 1000 (cpm/ml) | Viral load* (copies/ml) × $10^5$ | $TCID_{50}$/0.2 ml$^\dagger$ |
|---|---|---|---|
| Co-Cultured with CD8-Positive Cells | | | |
| 1. 92UG046-T8 | 27 | <50 | $10^8$ |
| 2. 93UG086-T8 | 454 | 52.1 | >$10^7$ |
| 3. 92US077-T8 | 632 | >37500 | $10^{6.85}$ |
| 4. 93US143-T8 | 551 | 7229.25 | $10^{8.3}$ |
| 5. 96USHIPS4-T8 | 1780 | 2604 | $10^7$ |
| 6. 96USHIPS9-T8 | 72 | <50 | $10^{6.5}$ |
| 7. 96USSN20-T8 | 2722 | 5.3 | $10^{6.5}$ |
| 8. AD3.v6 | 3914 | 4870.3 | $10^{5.75}$ |
| Co-Cultured with CD4-Positive Cells | | | |
| 1. 92UG046-T8 | 45 | <50 | $10^{6.9}$ |
| 2. 93UG086-T8 | 2420 | 176.8 | >$10^7$ |
| 3. 92US077-T8 | 246 | 946.6 | $10^7$ |
| 4. 93US143-T8 | 678 | 29250 | >$10^7$ |
| 5. 96USHIPS4-T8 | 3097 | 1298 | >$10^7$ |
| 6. 96USHIPS9-T8 | 624 | 5092.2 | $10^7$ |
| 7. 96USSN20-T8 | 2466 | 6.4 | >$10^7$ |
| 8. AD3.v6 | ND¶ | 1764.5 | ND |

*Viral load was detected using AMPLICOR kit.
$^\dagger TCID_{50}$ was measured with MT-2 cells.
¶ND stand for not done

EXAMPLE 8

The CD8-tropic viruses 92UG046-T8, 93UG086-T8, 92US077-T8, 93US 143-T8, 96USHIPS4-T8, 96USHIPS9-T8 and 96USSN20-T8 were able to infect the CD8-positive/CD4-negative cell line, KRCD8 as shown by experiments carried out as described in Example 2. In the experiments, all of the CD8-tropic viruses had the ability to infect KRCD8 cells as indicated by the presence of viral DNA soon after infection and by induction of HIV-specific transcripts. Virus from patients that did not exhibit CD8-tropism 92UG046-T8, 93UG086-T8, 92US077-T8, 93US143-T8, 96USHIPS4-T8, 96USHIPS9-T8 and 96USSN20-T8 were unable to replicate in KRCD8 cells.

Infection of KRCD8 cells by the CD8-tropic viruses was also confirmed by detection of viral particles using electron microscopy and by the ability of KRCD8 cell-produced viruses to transactivate β-galactosidase expression under the control of the HIV-LTR promoter. The transactivation assays were carried out using MAGI cells as described in Huang et al. *J. Virol.* 72: -2047–2054, (1998).

Finally, experiments testing the ability of anti-CD4 antibodies to block infection of KRCD8 cells by CD8-tropic viruses 92UG046-T8, 93UG086-T8, 92US077-T8, 93US 143-T8, 96USHIPS4-T8, 96USHIPS9-T8 and 96USSN20-T8 were carried out as described in Example 3. Infection of KRCD8 cells by the CD8-tropic viruses could not be blocked by the addition of anti-CD4 antibodies that were able to block infection of CD4-positive cells by CD4-tropic HIV-1.

Together, these data establish that the CD8-tropic viruses 92UG046-T8, 93UG086-T8, 92US077-T8, 93US143-T8, 96USHIPS4-T8, 96USHIPS9-T8 and 96USSN20-T8 are able to infect CD8-positive cells independent of CD4 as are AD3.v6 and AD3.v22.

EXAMPLE 9

In another experiment, the ability of the CD8-tropic viruses to induce syncitia in CD8-positive cells was investigated. CD4-tropic viruses are classified as SI or NSI based on their ability to induce or not to induce syncitia in CD4-positive cells, respectively. Induction of syncitia in CD4-positive cells by CD4-tropic viruses is generally mediated through the use of CXCR4 co-receptors. All CD8-tropic viruses in this study were also of SI phenotype in primary CD4-positve cells (Table 4) as well as in MT-2 (CD4-positive) cells.

TABLE 4

| HIV-l/T8 Viruses | Syncitia KDC8 cells | Syncitia MT2 cells | Syncitia (co-culture with CD8-Positive Cells) | Syncitia (co-culture with CD4-Positive Cells) |
|---|---|---|---|---|
| 1. 92UG046-T8 | + | + | + | + |
| 2. 93UG086-T8 | − | + | − | + |
| 3. 92US077-T8 | − | + | − | + |
| 4. 93US143-T8 | + | + | + | + |
| 5. 96USHIPS4-T8 | − | + | − | + |
| 6. 96USHIPS9-T8 | + | + | + | + |
| 7. 96USSN20-T8 | − | + | − | + |
| 8. AD3.v6 | − | + | − | + |

CD8-tropic viruses from three patients (92UG046-T8, 93US143-T8 and 96USHIPS9-T8) were also able to induce syncitia in primary CD8-positive cells (Table 4). These three CD8-tropic viruses also induced striking syncitia 2–5 days after infection in KRCD8 cells. Induction of syncitia in CD8-positive cells by the three CD8-tropic viruses was quickly followed by extensive cell death. As shown above, although CD8-tropic viruses 93UG086-T8, 92US077-T8, 96USHIPS4-T8, and 96USSN20-T8 from the other five patients were able to infect KRCD8 cells, none of the viruses were able to immediately induce syncitia in the KRCD8 cells.

Taken together, these results demonstrate that CD8-tropic viruses may also be of SI or NSI phenotypes in CD8-positive cells

EXAMPLE 10

The DNA sequences of the envelope proteins of the CD8-tropic viruses 92UG046-T8, 93UG086-T8, 92US077-T8, 93US143-T8, 96USHIPS4-T8, 96USHIPS9-T8 and 96USSN20-T8 were determined and the sequences are set out as SEQ ID NOS: 10, 12, 14, 16, 18, 20 and 22.

The full length envelope coding regions of the CD8-tropic viruses were amplified by nested PCR from infected CD8-positive cells and the amplified PCR fragments were sequenced from both DNA strands using a panel of primers (SEQ ID NOS: 16–19) by cycle sequencing on an ABI 377 DNA sequencer as previously described in Example 5. Envelope sequences from CD4-positive cells infected with the bulk viral stocks from these patients were also examined and compared to the CD8-tropic envelope viral sequences. Other envelope sequences from HIV-1 viruses isolated from these patients are available in the Los Alamos HIV database from previous studies and were compared with the isolated CD8-tropic sequences of the invention. Sequence assembly and comparisons were performed with Lasergene (DnaStar, Madison, Wis.) as well as with NCBI Blast server. The envelope sequences of the CD8-tropic viruses have been submitted to Genbank (accession numbers AF 391548–391553).

A comparison of the envelope sequences from a representative CD8-tropic virus 92UG046T8 with the previously published sequences (obtained from infected CD4-positive cells) is shown in FIG. 6. In the figure, dashes signify 100% identity among sequences and dots signify the absence/deletion of a base. FIG. 6 displays the full length envelope polypeptide sequence (gp120 and gp41). Locations of the V1, V2, V3, V4 and V5 loops are clearly identified in FIG. 6 along with the location of where the gp120 polypeptide ends. Several amino acid changes were observed between the envelopes of isolated CD8-tropic viruses when compared to the sequences in the Los Alamos database. These changes were scattered in the important V1-V2, C2 and V4 loops. Other CD8-tropic viruses also had diverse changes in the variable as well as transmembrane regions. The CD8-tropic AD3.v6 and AD3.v232 identified in Example 1, also had interesting changes in the V1, V2 and C2 regions.

Sequence analysis (VESPA) identified particular changes which are associated with CD8-tropism. The VESPA analysis was carried out with a threshold at 80% to compare the frequencies of residues at a specific site as compared to a background set (Los Alamos HIV database). The sites associated with CD8-tropism are contemplated to be those at which the frequency in the query set is greater than the frequency in the background set. These changes are summarized in below in Table 5.

TABLE 5

| Position | Protein Domain | Query residue | Frequency* | Background residue | Frequency |
|---|---|---|---|---|---|
| 270 | C2 | I | 80% | V | 85.1% |
| 693 | gp41 | I | 100%* | V | 58.8% |
| 724 | gp41 | Q | 80% | P | 63.8% |
| 779 | gp41 | A | 80% | T | 58.5% |
| 177 | V2 | D/E | 88.3%* | Q | 60% |
| 185 | V2 | D/E | 83%* | K/R | 40% |
| 187a | V2 | gap | 81.9%* | N | 40% |
| 187b | V2 | gap | 81.9%* | N | 60% |
| 187c | V2 | gap | 81.9%* | N | 60% |
| 209 | C2 | S | 98.9%* | T | 40% |
| 352 | C3 | Q | 89.4%* | H | 60% |
| 400a | V4 | gap | 98.9%* | D/E | 40% |
| 442 | C4 | Q | 81.9%* | L | 40% |
| 662 | gp41 | D/E | 85.1%* | A | 60% |

*Significant Frequency

No sequence change was observed among the CD8-tropic viruses in their CD4-binding region (bold in FIG. 6) or other residues known to be important for CD4-tropism indicating that mutations in the CD8-tropic strains are probably not just random events.

Additional sequence analysis revealed the CD8-tropic envelope sequence from the 92UG046-T8 isolate a stop codon within the transmembrane domain which resulted in a truncated gp41 proteins with a cytoplasmic tail about 70 amino acids shorter than the CD4-tropic envelope protein from the same patient. In addition, the CD8-tropic env sequence from the 93UG086-T8 and 96USSN20-T8 viruses both have a seven amino acid insert (HSSLKGL; SEQ ID NO: 27) towards the end of the transmembrane domain.

EXAMPLE 11

The foregoing examples demonstrate for the first time that HIV-1 can mutate to a form that can infect CD8-positive cells using CD8 as a primary receptor. These data are significant because despite a strong CD8-positive cell-mediated immune response after primary HIV infection, the host immune defense eventually fails leading to the development of AIDS. Although several hypotheses including anergy, apoptosis and antigenic stimulation have been put forward, the exact reason for ultimate failure of CD8-positive cells had been unclear. The existence of CD8-tropic HIV-1 can explain the failure of CD8-positive cells in AIDS patients. With increasing selective pressure from a declining pool of CD4-positive cells as infection progresses. HIV-1 evolves to be able to infect CD8-positive cells. Productive infection of immune-competent CD8-positive cells with CD8-tropic HIV-1 results in functional defects in these cells or kills these cells leading to a quantitative failure of the immune system and progression to AIDS. Blocking infection of CD8-positive cells by CD8-tropic HIV-1 is thus indicated as a vaccination strategy against, and as a therapy for, HIV-1 infection.

While the present invention has been described in terms of preferred embodiments, it is understood that variations and improvements will occur to those skilled in the art. Therefore, only such limitations as appear in the claims should be placed on the invention.

What is claimed is:

1. An isolated gp20 polypeptide comprising the amino acid sequence of SEQ ID NO: 10 or a fragment of the amino acid sequence of SEQ ID NO: 10 wherein the fragment binds to a CD8 protein.

2. An isolated HIV-1 gp120 polypeptide comprising an amino acid sequence encoded by a nucleotide sequence that hybridizes to the complement of the nucleotide sequence of SEQ ID NO: 9 under the following hybridization wash conditions: 0.015 M sodium chloride, 0.0015 M sodium citrate at 65–68° C., and wherein the polypeptide binds to a CD8 protein.

3. The polypeptide of claim 2, wherein the polypeptide comprises an amino acid encoded by the nucleotide sequence of SEQ ID NO: 9.

4. An isolated HIV-1 gp120 polypeptide comprising an amino acid sequence of SEQ ID NO: 10 having at least one conservative substitution, wherein the polypeptide binds to CD8 protein.

5. An immunogenic composition comprising a polypeptide of any one of claim 1, 2, 3 or 4.

6. A pharmaceutical composition comprising polypeptide of any one of claim 1, 2, 3 or 4.

* * * * *